(12) United States Patent
Dangond et al.

(10) Patent No.: US 10,849,919 B2
(45) Date of Patent: Dec. 1, 2020

(54) CLADRIBINE REGIMEN FOR TREATING PROGRESSIVE FORMS OF MULTIPLE SCLEROSIS

(71) Applicant: Merck Patent GmbH, Darmstadt (DE)

(72) Inventors: Fernando Dangond, Weston, MA (US); Matthias Dotzauer, Erzhausen (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 16/199,119

(22) Filed: Nov. 23, 2018

(65) Prior Publication Data

US 2019/0167707 A1    Jun. 6, 2019

Related U.S. Application Data

(60) Provisional application No. 62/590,442, filed on Nov. 24, 2017.

(51) Int. Cl.
| | | |
|---|---|---|
| *A61P 37/02* | (2006.01) |
| *A61K 31/7076* | (2006.01) |
| *A61K 9/20* | (2006.01) |
| *A61P 25/00* | (2006.01) |
| *A61K 38/21* | (2006.01) |

(52) U.S. Cl.
CPC ............ *A61K 31/7076* (2013.01); *A61K 9/20* (2013.01); *A61K 9/205* (2013.01); *A61K 9/2013* (2013.01); *A61K 9/2018* (2013.01); *A61K 38/215* (2013.01); *A61P 25/00* (2018.01); *A61P 37/02* (2018.01)

(58) Field of Classification Search
None
See application file for complete search history.

(56) References Cited

U.S. PATENT DOCUMENTS

| | | | |
|---|---|---|---|
| 5,208,327 A | 5/1993 | Chen | |
| 5,506,214 A | 4/1996 | Beutler | |
| 6,194,395 B1 | 2/2001 | Schultz et al. | |
| 8,377,903 B2* | 2/2013 | De Luca | A61K 38/215 514/46 |
| 2010/0203017 A1* | 8/2010 | De Luca | A61K 38/21 424/85.6 |
| 2017/0057983 A1* | 3/2017 | Wiles | C07F 9/6561 |

FOREIGN PATENT DOCUMENTS

| | | |
|---|---|---|
| EP | 0 173 059 | 3/1986 |
| EP | 0 626 853 | 4/2000 |
| WO | 96/19229 | 6/1996 |
| WO | 96/19230 | 6/1996 |
| WO | 00/64918 | 11/2000 |
| WO | 2004/028462 | 4/2004 |
| WO | 2004/087100 | 10/2004 |
| WO | 2004/087101 | 10/2004 |
| WO | 2006/067141 | 6/2006 |

OTHER PUBLICATIONS

Giovannoni et al., Safety and efficacy of cladribine tablets in patients with relapsing-remitting multiple sclerosis: Results from the randomized extension trial of the CLARITY study, 2018, Multiple Sclerosis Journal 24(12):1594-1604 (Year: 2018).*
Beutler et al., Acta Haematol; 1994, 91:10-15.
Beutler et al., Proc. Natl. Acad. Sci.; 1996, 93:1716-1720.
Beutler et al., Seminars in Hematology; 1996, 33(1):45-52.
Evans et al., Annals of Neurology, 1997; 41(1):125-132.
Giovannoni et al., The New England Journal of Medicine; 2010, 362(5):416-426.
Grieb et al., Archivum Immunologiae et Therapiae Experimentalis; 1995, 43:323-327.
Janiec et al., Clinical Research, Med Sci Monit; 2001, 7(1):93-98.
Kazimierczuk et al., J. Am. Chem. Soc.; 1984, 106:6379-6382.
Kurtzke, John F., Neurology; 1983, 33:1444-1452.
Lassmann et al., Trends in Molecular Medicine; 2001, 7(3):115-121.
Lublin et al., Neurology; 1996, 46:907-911.
Lucchinetti et al., Current Opinion in Neurology; 2001, 14:259-269.
Mattson, David H., Expert Rev. Neurotherapeutics; 2002, 2(3):319-327.
McDonald et al., Ann Neurol; 2001, 50:121-127.
Miller et al., Neurology; 1996, 47(4):S217.
Noseworthy et al., The New England Journal of Medicine, 2000; 343(13):938-952.
Poser et al., Annals of Neurology; 1983, 13(3):227-231.
Rice et al., Neurology; 2000, 54:1145-1155.
Romine et al., Proceedings of the Association of American Physicians; 1999, 111(1):35-44.
Schumacher et al., Annals New York Academy of Sciences; 1965, 122:552-568.
Selby et al., The Canadian Journal of Neurological Sciences; 1998, 25(4):295-299.
Sipe et al., Neurology, 1984; 34:1368-1372.
Sipe et al., The Lancet; 1994, 344:9-13.
Stelmasiak et al., Laboratory Investigations, Med Sci Monit; 1998, 4(1):4-8.
"Types of Multiple Sclerosis," https://mymsaa.org/ms-information/overview/types/, Feb. 26, 2020, 5 pages.

* cited by examiner

*Primary Examiner* — John D Ulm
(74) *Attorney, Agent, or Firm* — Grüneberg and Myers PLLC

(57) ABSTRACT

Specific oral dosings, specific oral dosage forms, and/or specific oral dose regimens including Cladribine can be effective for the treatment of progressive forms of Multiple Sclerosis, especially Primary Progressive Multiple Sclerosis and/or Secondary Progressive Multiple Sclerosis. Methods of treatment can be based on specific oral dosings, specific oral dosage forms, and/or specific oral dose regimens including Cladribine.

34 Claims, 4 Drawing Sheets

CLADRIBINE REGIMEN FOR TREATING PROGRESSIVE FORMS OF MULTIPLE SCLEROSIS

CROSS-REFERENCE TO RELATED APPLICATIONS

This application claims the benefit of U.S. Provisional Application No. 62/590,442, filed on Nov. 24, 2018, the entirety of which is incorporated herein by reference.

BACKGROUND OF THE INVENTION

Field of the Invention

The present invention relates to the use of specific oral dosings, specific oral dosage forms and/or specific oral dose regimens comprising Cladribine for the treatment of progressive forms of Multiple Sclerosis, especially Primary Progressive Multiple Sclerosis and/or Secondary Progressive Multiple Sclerosis.

Description of the Related Art

Multiple sclerosis (MS) is the most known chronic inflammatory demyelinating disease of the central nervous system in humans. The onset of the disease typically occurs during ages 20 to 40. Women are affected approximately twice as often as men.

Over time, MS may result in the accumulation of various neurological disabilities. Clinical disability in MS is presumed to be a result of repeated inflammatory injury with subsequent loss of myelin and axons, leading to tissue atrophy.

MS is often manifested in physical symptoms (relapses and disability progression), Central Nervous System (CNS) inflammation, brain atrophy and cognitive impairment. Presenting symptoms include focal sensory deficits, focal weakness, visual problems, imbalance and fatigue. Sexual impairment and sphincter dysfunction may occur. Approximately half of the patients with MS may experience cognitive impairment or depression.

MS is often considered to be a multi-phasic disease and periods of clinical quiescence (remissions) occur between exacerbations. Remissions vary in length and may last several years but are infrequently permanent.

Four courses of the disease are generally differentiated: relapsing-remitting (RR), secondary progressive (SP), primary progressive (PP) and progressive relapsing (PR) multiple sclerosis.

More than 80% of patients with MS will initially display a RR course with clinical exacerbation of neurological symptoms, followed by a recovery that may or may not be complete (Lublin and Reingold, *Neurology*, 1996, 46:907-911).

During RRMS, accumulation of disability results from incomplete recovery from relapses. Approximately, half of the patients with RRMS switch to a progressive course, called SPMS, 10 years after the diseased onset. During the SP phase, worsening of disability results from the accumulation of residual symptoms after exacerbation but also from insidious progression between exacerbations (Lublin and Reingold above). 10% of MS patients have PPMS which is characterized by insidious progression of the symptoms from the disease onset. Less than 5% of patients have PRMS and are often considered to have the same prognosis as PPMS. It is suggested that distinct pathogenic mechanisms may be involved in different patient sub-groups and have wide-ranging implications for disease classification (Lassmann et al., 2001, *Trends Mol. Med.*, 7, 115-121; Lucchinetti et al., *Curr. Opin. Neurol.*, 2001, 14, 259-269).

MS onset is defined by the occurrence of the first neurological symptoms of CNS dysfunction. Advances in cerebrospinal fluid (CSF) analysis and magnetic resonance imaging (MRI) have simplified the diagnostic process and facilitated early diagnostic (Noseworlhy et al., *The New England Journal of Medicine*, 2000, 343, 13, 938-952). The International Panel on the Diagnosis of MS issued revised criteria facilitating the diagnosis of MS and including MRI together with clinical and para-clinical diagnostic methods (Mc Donald et al., 2001, *Ann. Neurol.*, 50:121-127).

Current medications for MS which are disease modifying treatments, i.e. modifying the course of MS, modulate or suppress the immune system. There have been several FDA approved immunomodulating agents for RRMS in the past, including the following: three beta interferons (Betaseron®, Berlex; Avonex®, Biogen; Rebif®, Serono) and Glatimarer Acetate (Copaxone®, Amgen). There is also one FDA approved immunosuppressing drug for worsening MS, Mitoxantrone (Novantrone®, Amgen). Several other immunosuppressive agents are used, although not FDA approved. However, meanwhile the arsenal of the so-called Disease Modifying Drugs (DMDs) or Disease Modifying Therapeutics/Therapies (DMTs) comprises the following:

Interferon beta-1a, Beta interferon-1a (e.g. Avonex®, Rebif®),
Interferon beta-1b, Beta interferon-1b (e.g. Betaferon®, Extavia®),
Peginterferon beta 1a (e.g. Plegridy®),
Alemtuzumab (e.g. Lemtrada®),
Daclizumab (e.g. Zinbryta®),
Dimethyl fumarate (e.g. Tecfidera®),
Fingolimod (e.g. Gilenya®),
Glatiramer acetate (e.g. Copaxone®),
Natalizumab (e.g. Tysabri®), and
Teriflunomide (e.g. Aubagio®).

The newest addition to this class of therapeutics is Cladribine Tablets (Mavenclad®), approved by the EMA in August 2017 for the treatment of Relapsing Remitting Multiple Sclerosis in patients with high disease activity.

However, all those therapeutics are only approved by the health authorities (such as FDA, EMA) for the treatment of Relapsing Remitting Multiple Sclerosis (RRMS), however none of them is approved for progressive forms of Multiple Sclerosis, including, but not limited to Primary Progressive Multiple Sclerosis (PPMS) and Secondary Progressive Multiple Sclerosis (SPMS).

In fact, there is to date only one therapeutic approved for the treatment of PPMS, Ocrelizumab (Ocrevus®), but it has gained so far moderate interest and success in this indication, at best. Other Clinical Studies in PPMS, e.g. the PROMISE Study (employing glatiramer acetate as the study drug), the OLYMPUS study (employing rituximab as the study drug), and the INFORMS Study (employing fingolimod as the study drug) did not reach meaningful clinical endpoints. However, minor clinical activity was seen in a subset of patients identified as Early Secondary Progressive Multiple Sclerosis patients.

Interestingly, this so-called Early Secondary Progressive Multiple Sclerosis (ESPMS) is some form of Multiple Sclerosis that marks some kind of transition state between the relapsing remitting forms of MS and the progressive forms of MS. This form combines the very different aspects and also very different mechanisms of both the pure relapsing remitting forms and the progressive forms of MS.

As a result, without wishing to be bound by theory, it is believed that the minor efficacy or minor clinical effects seen in all the above mentioned PPMS trials with DMDs other than Ocrelizumab, i.e. DMDs originally approved for RRMS, is just based on a simple mechanism:
all patients that experienced said minor or moderate efficacy of the DMDs approved for RRMS where actually patients in the transition state between relapsing remitting forms of MS and progressive forms of MS, including ESPMS, in which the RRMS aspects and mechanisms exclusively where (partly) treated, not having any effect or efficacy against the progressive aspects and mechanisms of the SPMS or PPMS and their contribution to the overall state of the patient. Accordingly, the very unsatisfying results of the above discussed trials employing RRMS approved DMDs clearly show that the mechanism underlying the relapsing remitting forms on one hand and the progressive forms on the other hand are very different and were not accessible by those RRMS approved DMDs.

Based on the above, there is clearly a high unmet medical need for therapeutics that are effective in the field of progressive forms of MS.

Based on new and surprisingly advantageous clinical results discussed herein in detail, without wishing to be bound by theory, it is believed that specific oral dosings, specific oral dosage forms and/or specific oral dose regimens described herein comprising the active ingredient Cladribine, newly approved for the treatment of RRMS in patients with high disease activity, are also effective in the treatment of progressive forms of MS, clearly beyond the treatment of ESPMS, and especially effective for the treatment of PPMS and/or SPMS, both with Cladribine as a single agent and in combination with other DMDs.

To go into more detail, the results from the ONWARD Study, which contained both RRMS and SPMS patients, surprisingly show that Cladribine-treated RRMS patients (i.e. patients that received oral Cladribine according to the now approved RRMS label for Cladribine) were 50% less likely to have a qualifying relapse than those treated with placebo, whereas Cladribine-treated SPMS patients (i.e. SPMS patients that likewise received oral Cladribine according to the now approved RRMS label for Cladribine) were 89% less likely to have a qualifying relapse than those treated with placebo. This significant difference in efficacy as shown by the instant clinical data is a to date unexpected advantage for the SPMS patients treated with Cladribine and clearly shows the clinical efficacy and potential of Cladribine in the treatment of progressive forms of MS, including both SPMS and PPMS, which appears to be clearly independent from the co-medication administered to all patients, including the patients that received placebo instead of Cladribine. Remarkably, oral Cladribine appears to be able to strongly downregulate the targets and mechanisms of the severely different inflammatory processes that are characteristic for progressive forms of MS, preferably including both SPMS and PPMS. Due to oral Cladribine's unique properties, including, but not limited to, a short half-life combined with a prolonged pharmacodynamic (PD) and a uniquely specific effect on a variety of specific immune cells, most notably a reversible reduction in T-cell and B-cell counts with previously unknown selectivity, oral Cladribine for use according to the instant invention it is believed to become a breakthrough therapeutic in the treatment of one or more progressive forms of MS, including but not limited PPMS and/or SPMS, preferably PPMS.

Cladribine, a synthetic chlorinated purine analogue 2-chloro-2'deoxyadenosine (2-CdA) (Beutler, 1992), has been suggested to be useful in the treatment of MS (EP 626853B1 and U.S. Pat. No. 5,506,214).

Several clinical studies with Cladribine in patients with multiple sclerosis have investigated the use of i.v. and s.c. Cladribine in MS.

Two double-blind, placebo-controlled Phase II studies were conducted respectively in the treatment of Chronic Progressive MS (Selby et al., 1998, *Can. J. Neurol. Sci.*, 25:295-299) and Relapsing-Remitting MS respectively (Romine et al., 1999, *Proceedings of the Association of American Physicians*, 111, 1, 35-44).

In the first trial, the Cladribine dose used was 0.1 mg/kg/day for 7 days by continuous i.v. infusion. The treatment for repeated for 4 consecutive months.

In the second clinical trial, the Cladribine dose used was 0.07 mg/kg/day for 5 days by subcutaneous injection. The treatment was repeated for 6 consecutive months.

In addition, placebo-controlled Phase III study was conducted in patients with primary progressive (PP) or secondary progressive (SP) multiple sclerosis (Rice at al., 2000, *Neurology*, 54, 5, 1145-1155). In this study, both patient groups received Cladribine by subcutaneous injection at a dose of 0.07 mg/kg/day. The treatment was repeated for either 2 months or 6 months.

The Phase II clinical studies provided evidence for the positive effects of Cladribine in patients with MS in terms of Kutzke Extended Disability Status Scale (EDSS), Scripps Neurologic rating Scale (SNRS) scores and Magnetic Resonance Imaging (MRI) findings (Beutler et al., 1996 *Proc. Nat. Acad. Sci. USA*, 93, 1716-1720; Romine et al., 1999 above). Phase III study results were positive on the significant reduction of MRI-measured brain lesions (Rice at al., 2000, above).

Some adverse effects (AEs), such as increased incidence of infections related to compromised immune function or myelosuppression, were observed with the highest doses (Selby et al., 1998, above; Beutler et al., 1994, *Acta hematol.*, 91:10-15). Due to the narrow margin of safety between the efficacy dose and the dose of occurrence of AEs, to date, all clinical trials for Cladribine in multiple sclerosis have been conducted using either i.v. or s.c. administration. As a result, Beutler et al. (Beutler et al., 1996, *Seminars in Hematology* 33, 1(S1), 45-52) excluded the oral route for the treatment of multiple sclerosis with Cladribine.

Grieb et al. reported a small trial in 11 patients with remitting-relapsing multiple sclerosis (Grieb et al., 1995, *Archivum Immunologiae et Therapiae Experimentalis*, 43 (5-6), 323-327) wherein Cladribine has been orally administered during 6 monthly courses of 5 days at a total dose of about 4-5.7 mg/kg (patients of about 52 and about 75 kilos, respectively) i.e. a total effective dose of 2-2.85 mg/kg. For some patients, a single re-treatment of 5 days was performed at a cumulative dose of 0.4-0.66 mg/kg after a Cladribine free-period of 3 or 6 months. The side effects observed with the regimen above were said to be less severe than the ones observed in the study on patients suffering from chronic progressive multiple sclerosis treated by i.v. infusion of Cladribine (Sipe et al., 1994, *Lancet*, 344, 9-13) but were still present. In addition, the therapeutic efficacy of the oral regimen above versus the i.v. infusion therapy was questioned (Grieb et al., 1995, above) and a group of "non-responders" has been identified (Stelmasiak et al., 1998, *Laboratory Investigations*, 4(1), 4-8).

Giovannoni et al (N Engl J Med 2010) report about a placebo-controlled phase III trial of oral Cladribine for relapsing multiple sclerosis (ClinicalTrials.gov number, NCT00213135). According to that, Cladribine provides immunomodulation through selective targeting of lymphocyte subtypes. Giovannoni et al describe the results of a 96-week phase 3 trial of a short-course oral tablet therapy in patients with relapsing-remitting multiple sclerosis. In that trial, 1326 patients were randomly assigned in an approximate 1:1:1 ratio to receive one of two cumulative doses of Cladribine tablets (either 3.5 mg or 5.25 mg per kilogram of body weight) or matching placebo, given in two or four short courses for the first 48 weeks, then in two short courses starting at week 48 and week 52 (for a total of 8 to 20 days per year). The primary end point was the rate of relapse at 96 weeks. Among patients who received Cladribine tablets (either 3.5 mg or 5.25 mg per kilogram), there was a significantly lower annualized rate of relapse than in the placebo group (0.14 and 0.15, respectively, vs. 0.33; P<0.001 for both comparisons), a higher relapse-free rate (79.7% and 78.9%, respectively, vs. 60.9%; P<0.001 for both comparisons), a lower risk of 3-month sustained progression of disability (hazard ratio for the 3.5-mg group, 0.67; 95% confidence interval [CI], 0.48 to 0.93; P=0.02; and hazard ratio for the 5.25-mg group, 0.69; 95% CI, 0.49 to 0.96; P=0.03), and significant reductions in the brain lesion count on magnetic resonance imaging (MRI) (P<0.001 for all comparisons). Adverse events that were more frequent in the Cladribine groups included lymphocytopenia (21.6% in the 3.5-mg group and 31.5% in the 5.25-mg group, vs. 1.8%) and herpes zoster (8 patients and 12 patients, respectively, vs. no patients). Thus, treatment with Cladribine tablets significantly reduced relapse rates, the risk of disability progression, and MRI measures of disease activity at 96 weeks. However, the benefits are said to be needed to be weighed against the risks.

Therefore, it would be desirable to have a method for treating multiple sclerosis comprising the oral administration of Cladribine that would permit the same or improved effect on MS lesions while decreasing the occurrence adverse events, severity of adverse events and/or the progression of the disease in general also for patients suffering from progressive forms of MS, preferably selected from the group consisting of PPMS and/or SPMS. In addition, as MS is a chronic disease, it would be desirable to decrease the occurrence and/or severity adverse events in such a way that re-treatments are possible. A sustained benefit of Cladribine treatment between the treatment periods and/or beyond treatment periods is also desirable.

BRIEF SUMMARY OF THE INVENTION

The present invention is inter-alia directed towards new uses of Cladribine for the preparation of oral pharmaceutical formulations for the treatment of progressive forms of Multiple Sclerosis, including, but not limited to Primary Progressive Multiple Sclerosis and/or Secondary Progressive Multiple Sclerosis, wherein said pharmaceutical formulations are to be the orally administered according a certain regimen. Additionally, the invention is to directed towards specific methods of treating patients suffering from progressive forms of Multiple Sclerosis, including, but not limited to Primary Progressive Multiple Sclerosis and/or Secondary Progressive Multiple Sclerosis, comprising orally administering Cladribine according to a certain regimen.

Furthermore, the invention provides improved dosing regimen for the oral use of Cladribine in the treatment of progressive form of Multiple Sclerosis.

An additional aspect of the invention relates to a use of Cladribine for the preparation of a pharmaceutical formulation for the treatment of progressive forms of Multiple Sclerosis, wherein efficacy to the patient is provided and/or wherein adverse effects are reduced, thus preferably providing new therapeutic options for patients suffering from progressive forms of multiple sclerosis.

Furthermore, the invention preferably provides a use of Cladribine for the preparation of a pharmaceutical formulation wherein the formulation is to be orally administered as described herein.

The efficacy of cladribine in the treatment of progressive forms of MS, including PPMS and/or SPMS, can preferably be shown by improvements with regard to one or more selected from Expanded Disability Status Scale (EDSS), No Evidence of Disease Activity (NEDA), No Evidence Of Progression Or Active Disease (NEPAD) and/or Quality of Life (QoL), preferably as known and described in the art and/or as described herein. Additionally, or alternatively, MRI measures of lesions can preferably be likewise used in order to track efficacy, preferably as known and described in the art and/or as described herein.

DETAILED DESCRIPTION OF THE INVENTION

Figure 1:
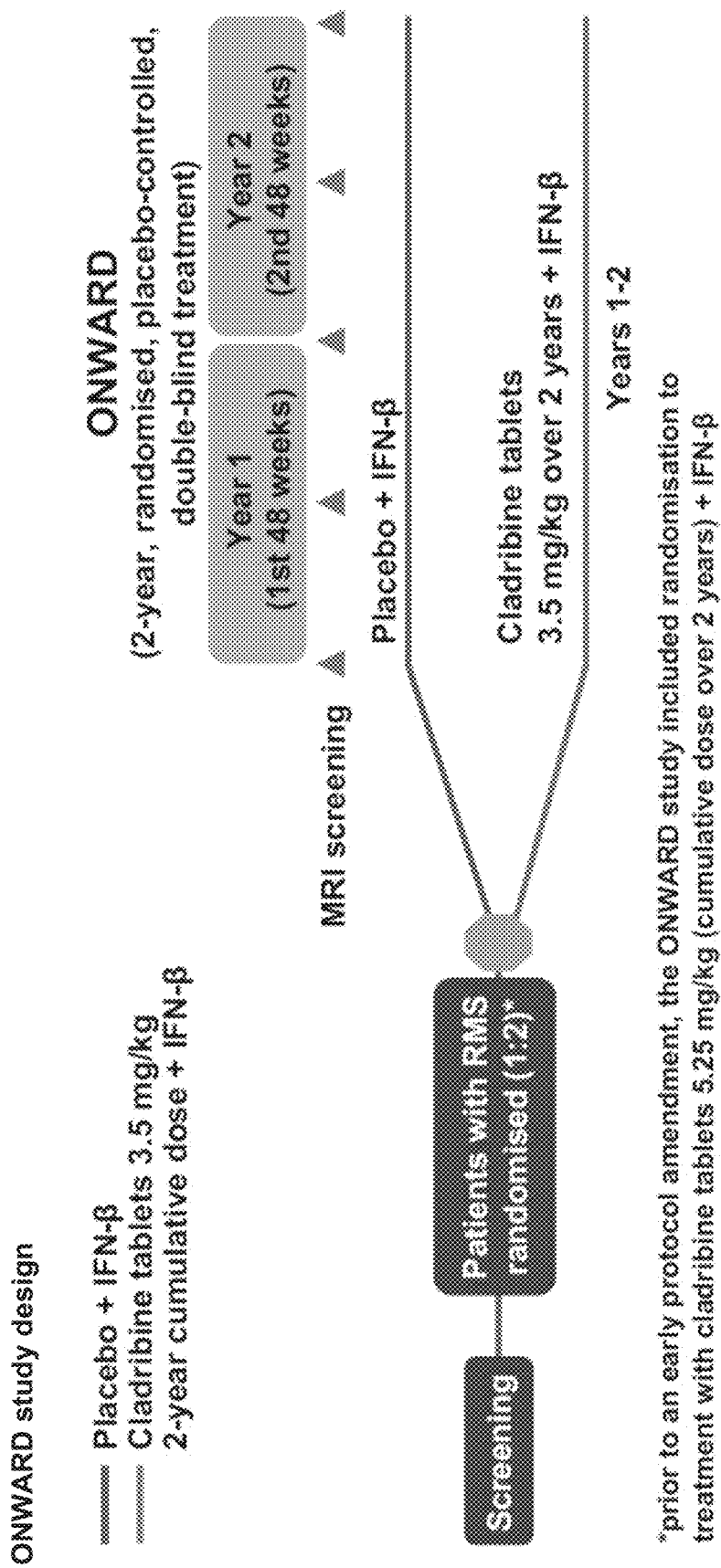
FIG. 1 shows the ONWARD study design in Example 1.

The instant invention is described in more detail in the Sections given below including the following embodiments:
1. Cladribine for use in the oral treatment of patients suffering from progressive forms of Multiple Sclerosis, wherein said Cladribine is to be orally administered to each patient at a certain dose that is calculated per patient, per body weight and per treatment year, wherein said dose or said certain dose is selected from the range of 1.5 mg/kg to 4.0 mg/kg. Preferably, a dose that is calculated per patient, per body weight of the patient and per treatment year is referred to as a "fixed dose". Thus, preferred is Cladribine for use in the oral treatment of patients suffering from progressive forms of Multiple Sclerosis, wherein said Cladribine is to be orally administered to each patient at fixed dose per patient, per body weight and per treatment year, wherein said fixed dose is selected from the range of 1.5 mg/kg to 4.0 mg/kg. Typically, a treatment year lasts about 12 months. Administration of Cladribine may be to a patient in need thereof or a subject in need thereof.
2. Cladribine for use as described herein, preferably as described in one or more of the numbered Sections above and/or below and more preferably as described in Section 1, wherein said fixed dose is selected from the range of 1.5 mg/kg to 2.0 mg/kg, preferably selected from the range of 1.5 mg/kg to 2.0 mg/kg per year. Especially preferred is Cladribine for use as described herein, preferably as described in one or more of the numbered Sections above and/or below and more preferably as described in Section 1, wherein said fixed dose is selected from the range of 1.5 mg/kg to 2.0 mg/kg, preferably selected from the range of 1.5 mg/kg to 2.0 mg/kg per year, for two consecutive treatment years. Thus, said fixed dose is preferably selected from the range of 3.0 mg/kg to 4.0 mg/kg over two consecutive years (or to be administered over two consecutive years), wherein said fixed dose is selected from the range of 1.5 mg/kg to 2.0 mg/kg per year in each of the two years.

3. Cladribine for use as described herein, preferably as described in one or more of the numbered Sections above and/or below and more preferably as described in Section numbered 1 and/or 2, wherein said fixed dose per patient, preferably for each patient, is 1.75 mg/kg per treatment year with a maximum deviation of +/−0.2 mg/kg. Especially preferred is Cladribine for use as described herein, preferably as described in one or more of the numbered Sections above and/or below and more preferably as described in Section numbered 1 and/or 2, wherein said fixed dose per patient, preferably for each patient, is 1.75 mg/kg per treatment year with a maximum deviation of +/−0.2 mg/kg, for two consecutive treatment years. Thus, said fixed dose per patient, preferably for each patient, is preferably 3.5 mg/kg over two consecutive years with a maximum deviation of +/−0.4 mg/kg.

4. Cladribine for use as described herein, preferably as described in one or more of the numbered Sections above and/or below and more preferably as described in Section 1, 2 and/or 3, where said progressive forms of multiple sclerosis comprise Primary Progressive Multiple Sclerosis and/or Secondary Progressive Multiple Sclerosis, and especially consist of Primary Progressive Multiple Sclerosis and/or Secondary Progressive Multiple Sclerosis.

5. Cladribine for use as described herein, preferably as described in one or more of the numbered Sections above and/or below and more preferably as described in Section 1, 2, 3 and/or 4, wherein said progressive form of Multiple Sclerosis is Primary Progressive Multiple Sclerosis. Preferably, Cladribine is used according to the invention for patients that are already diagnosed Primary Progressive Multiple Sclerosis before the start of the treatment. More preferably, Cladribine is used as described herein and especially as described above and/or below for patients that are already diagnosed Primary Progressive Multiple Sclerosis before the start of the treatment.

6. Cladribine for use as described herein, preferably as described in one or more of the numbered Sections above and/or below and more preferably as described in Section 1, 2, 3 and/or 4, wherein said progressive form of Multiple Sclerosis is Secondary Progressive Multiple Sclerosis. Preferably, Cladribine is used according to the invention for patients that are already diagnosed Secondary Progressive Multiple Sclerosis before the start of the treatment. Preferably, Secondary Progressive Multiple Sclerosis does not include Early Secondary Progressive Multiple Sclerosis.

7. Cladribine for use as described herein, preferably as described in one or more of the numbered Sections above and/or below and more preferably for use according to one or more of the preceding Sections, wherein said Cladribine is to be orally administered to patients having an age between 18 and 65 years, preferably inclusive of patients having the age of 18 years and patients having the age of 65 years.

8. Cladribine for use as described herein, preferably as described in one or more of the numbered Sections above and/or below and more preferably for use according to one or more of the preceding Sections, wherein said Cladribine is to be orally administered to patients having an age between 18 and 51 years, preferably inclusive of patients having the age of 18 years and having the age of 51 years.

9. Cladribine for use as described herein, preferably as described in one or more of the numbered Sections above and/or below and more preferably for use according to one or more of the preceding Sections, wherein said Cladribine is to be orally administered to patients having an age between 12 and 51 years, preferably inclusive of patients having the age of 18 years and having the age of 51 years.

10. Cladribine for use as described herein, preferably as described in one or more of the numbered Sections above and/or below and more preferably for use according to one or more of the preceding numbered Sections, wherein said Cladribine is to be orally administered to patients of female gender and/or to patients of male gender. Since female patients are more often affected and/or often more severely affected by progressive forms of multiple sclerosis, it is a preferred aspect of the instant invention to treat female patients in this regard.

11. Cladribine for use as described herein, preferably as described in one or more of the numbered Sections above and/or below and more preferably for use according to one or more of the preceding numbered Sections, wherein said Patient has High Disease Activity (HDA) and/or has been diagnosed High Disease Activity. Preferably, Cladribine is used according to the invention for patients that are already diagnosed High Disease Activity before the start of the treatment. More preferably, Cladribine is used described herein, preferably as described in one or more of the numbered Sections above and/or below and more preferably for use according to one or more of the preceding numbered Sections, for patients that are already diagnosed High Disease Activity before the start of the treatment 12. Cladribine for use as described herein, preferably as described in one or more of the numbered Sections above and/or below and more preferably for use according to one or more of the preceding Sections, wherein said Cladribine is to be orally administered to patients being treatment naïve to Cladribine and/or disease modifying drugs other than Cladribine.

13. Cladribine for use as described herein, preferably as described in one or more of the numbered Sections above and/or below and more preferably for use according to one or more of Sections 1 to 11, wherein said Cladribine is to be orally administered to patients who previously received Cladribine and/or disease modifying drugs other than Cladribine. Preferably, in this regard the disease modifying drugs other than Cladribine comprise Interferon beta-1a, Beta interferon-1a (e.g. Avonex®, Rebif®).

14. Cladribine for use as described herein, preferably as described in one or more of the numbered Sections above and/or below and more preferably for use according to one or more of the preceding Sections, wherein said Cladribine is to be orally administered to patients also receiving one or more disease modifying drugs other than Cladribine. Preferably, in this regard the disease modifying drugs other than Cladribine comprise Interferon beta-1a, Beta interferon-1a (e.g. Avonex®, Rebif®).

15. Cladribine for use as described herein, preferably as described in one or more of the numbered Sections above and/or below and more preferably for use according to one or more of Sections 12-14, wherein said disease modifying drugs other than Cladribine are selected from the group consisting of:
    Interferon beta-1a, Beta interferon-1a (e.g. Avonex®, Rebif®),
    Interferon beta-1b, Beta interferon-1b (e.g. Betaferon®, Extavia®),
    Peginterferon beta 1a (e.g. Plegridy®),
    Alemtuzumab (e.g. Lemtrada®),
    Daclizumab (e.g. Zinbryta®),
    Dimethyl fumarate (e.g. Tecfidera®),
    Fingolimod (e.g. Gilenya®),
    Glatiramer acetate (e.g. Copaxone®),
    Natalizumab (e.g. Tysabri®), and
    Teriflunomide (e.g. Aubagio®).

16. Cladribine for use as described herein, preferably as described in one or more of the numbered Sections above and/or below and more preferably for use according to one or more of the preceding Sections, wherein said Cladribine is to be orally administered to each patient at fixed dose per patient, per body weight and per treatment year, wherein said fixed dose is selected from the range of 1.5 mg/kg to 4.0 mg/kg, preferably selected from the range of 1.5 mg/kg to 2.0 mg/kg, and especially is, preferably for each patient, 1.75 mg/kg per treatment year with a maximum deviation of +/−0.2 mg/kg,
    and wherein the said fixed dose is orally administered to said patient within two adjacent months within said treatment year, preferably within two adjacent months at the beginning of said treatment year.

17. Cladribine for use as described herein, preferably as described in one or more of the numbered Sections above and/or below and more preferably for use according to Section 16, wherein said fixed dose is orally administered to said patient within two adjacent months starting at the beginning of said treatment year. More preferred is Cladribine for use as described herein, preferably as described in one or more of the numbered Sections above and/or below and more preferably for use according to Section 16, wherein said fixed dose is orally administered to said patient within two adjacent months starting at the beginning of each of said treatment years.

18. Cladribine for use as described herein, preferably as described in one or more of the numbered Sections above and/or below and more preferably for use according to Section 16 and/or 17, wherein said fixed dose is orally administered to said patient within one week or two weeks, preferably two adjacent weeks, in each one of said two adjacent months.

19. Cladribine for use as described herein, preferably as described in one or more of the numbered Sections above and/or below and more preferably for use according to Section 16, 17 and/or 18, wherein said fixed dose is orally administered to said patient within one week or two adjacent weeks located at the beginning of each one of said two adjacent months.

20. Cladribine for use as described herein, preferably as described in one or more of the numbered Sections above and/or below and more preferably for use according to Section 16, 17, 18 and/or 19, wherein said fixed dose is orally administered to said patient, preferably divided into the respective amounts numbers of daily doses, more preferably about equal doses, to be administered to said patient within 2 to 7 days during said week, or within 2 to 7 days of each of said weeks.

21. Cladribine for use as described herein, preferably as described in one or more of the numbered Sections above and/or below and more preferably for use according to Section 16, 17, 18, 19 and/or 20, wherein said fixed dose is orally administered to said patient, preferably divided into the respective amounts our numbers of daily doses, preferably about equal doses, within 2 to 7 days, preferably within 4 to 5 days during said week, or within 2 to 7 days, preferably within 4 to 5 days, of each of said weeks.
    Accordingly, a treatment year typically consists of 2 months of active treatment, i.e. 2 months wherein Cladribine is administered to the patient, and 10 months without active treatment, i.e. 10 months wherein no Cladribine is administered to said patients. Preferably, the 2 months of active treatment mark the beginning of the treatment year. Preferably, the Cladribine is administered to the patient during the respective first week of each said two months of active treatment.

22. Cladribine for use as described herein, preferably as described in one or more of the numbered Sections above and/or below and more preferably for use according to one or more of the preceding Sections, wherein said Cladribine is to be orally administered to each patient at said fixed dose per patient, per body weight and per treatment year, preferably as described in the Sections above and/or below, and wherein the treatment comprises one or more additional treatment years. Preferably, Cladribine for use as described herein is administered during two or more treatment years, more preferably 2 treatment years, which are preferably adjacent treatment years that are preferably basically identical.
    However, depending on the hematological state of the patient, it can become necessary or advantageous to separate two treatment years by a gap, i.e. a certain time where the previous treatment year is over and the foreseen next treatment year cannot or should not be started. Preferably and intentionally, Cladribine is not administered during such a gap. Typically, a gap in this regard lasts between 1 and 8 months, preferably between 1 and 6 months, more preferably between 1 and 3 months. Often, during such a gap, the hematological state of the patient is monitored in order to decide when the next treatment year can be started.

23. Cladribine for use as described herein, preferably as described in one or more of the numbered Sections above and/or below and more preferably for use according to one or more of the preceding Sections, wherein said Cladribine is to be orally administered to each patient at said fixed dose per patient, per body weight and per treatment year, preferably as described in the Sections above and/or below, and wherein the treatment comprises two treatment years, preferably two substantially identical treatment years.

24. Cladribine for use as described herein, preferably as described in one or more of the numbered Sections above and/or below and more preferably for use according to Section 20 and/or 21, wherein two of said treatment years are either directly adjacent to each other, or are separated by a gap 1 to 10 months. Typically, such a gap, if any, is induced by the hematological state of the patient at the end of the respective treatment year before the start of the new or subsequent treatment year. Sometimes, it can become necessary or advantageous to separate two treatment years by a gap, i.e. a certain time where the previous treatment year is over and the foreseen next treatment year cannot or should not be started. Preferably and intentionally, Cladribine is not administered during such a gap.

25. Cladribine for use as described herein, preferably as described in one or more of the numbered Sections above and/or below and more preferably for use according to one or more of the preceding Sections, wherein said Cladribine is to be orally administered to each patient at a fixed dose per patient, per body weight and per treatment year,
    a) wherein said fixed dose per treatment year is selected from the range of 1.5 mg/kg to 4.0 mg/kg, preferably selected from the range of 1.5 mg/kg to 2.0 mg/kg, and especially is, preferably for each patient, 1.75 mg/kg per treatment year with a maximum deviation of +/−0.2 mg/kg,
    b) wherein said treatment year comprises:
        (i) a treatment period of 2 months at the beginning of said treatment year, wherein said fixed dose of Cladribine is orally administered on about 1 to about 7 days each month, preferably on about 1 to about 7 days each month at the beginning of each month, said fixed dose being divided into daily doses of 5 to 20 mg of Cladribine, and
        (ii) a Cladribine-free period lasting 10 months, during which no Cladribine is administered.

26. Cladribine for use as described herein, preferably as described in one or more of the numbered Sections above and/or below and more preferably for use according to one or more of the preceding Sections, wherein said Cladribine is to be orally administered to each patient at a fixed dose per patient, per body weight and per treatment year,
    a) wherein said fixed dose per treatment year is selected from the range of 1.5 mg/kg to 4.0 mg/kg, preferably selected from the range of 1.5 mg/kg to 2.0 mg/kg, and especially is, preferably for each patient, 1.75 mg/kg per treatment year with a maximum deviation of +/−0.2 mg/kg,
    b) wherein said treatment year comprises:
        (i) a treatment period of 2 months at the beginning of said treatment year, wherein said fixed dose of Cladribine is orally administered on 3 to 5 days each month at the beginning of each month, said fixed dose being divided into daily doses of 10 or 20 mg of Cladribine,
        (ii) a Cladribine-free period lasting 10 months, during which no Cladribine is administered.

27. Cladribine for use as described herein, preferably as described in one or more of the numbered Sections above and/or below and more preferably for use according to one or more of the preceding Sections, wherein said oral treatment of patients suffering from Primary Progressive Multiple Sclerosis and/or patients suffering from Secondary Progressive Multiple Sclerosis, wherein said Cladribine is to be orally administered to each patient at fixed dose per patient, per body weight and per treatment year, wherein said fixed dose per patient is, preferably for each patient, 1.75 mg/kg per treatment year with a maximum deviation of +/−0.2 mg/kg, and wherein said treatment comprises at least two treatment years, preferably two or three treatment years.

28. Cladribine for use as described herein, preferably as described in one or more of the numbered Sections above and/or below and more preferably for use according to one or more of the preceding Sections, wherein the treatment comprises two treatment years that are substantially adjacent to either each other, or that are separated by a gap of 1 to 10 months, preferably 1 to 6 months, and especially 1 to 3 months.

29. Cladribine for use as described herein, preferably as described in one or more of the numbered Sections above and/or below and more preferably for use according to one or more of the preceding Sections, wherein the treatment additionally comprises a subsequent treatment year,
    a) wherein said fixed dose per treatment year is selected from the range of 0.75 mg/kg to 2.0 mg/kg, preferably selected from the range of 1.0 mg/kg to 1.5 mg/kg, and especially is, preferably for each patient, 0.8 mg/kg per treatment year with a maximum deviation of +/−0.2 mg/kg,
    b) wherein said subsequent treatment year comprises:
        (i) a treatment period of 1 month or 2 months at the beginning of said treatment year, wherein said fixed dose of Cladribine is orally administered on 3 to 5 days each month at the beginning of each month, said fixed dose being divided into daily doses of 10 or 20 mg of Cladribine,
        (ii) a Cladribine-free period lasting 11 or 10 months respectively, during which no Cladribine is administered.

30. Cladribine for use as described herein, preferably as described in one or more of the numbered Sections above and/or below and more preferably for use according to one or more of the preceding Sections, wherein the treatment comprises one or two treatment years as described in the Sections above and/or below, preferably 2 treatment years as described in the Sections above and/or below, optionally plus an additional subsequent treatment year as described in Section 26 or 29, followed by at least one year, preferably at least 2 years, in which no Cladribine is administered to said patients.

31. Cladribine for use as described herein, preferably as described in one or more of the numbered Sections above and/or below and more preferably for use according to one or more of the preceding Sections, wherein said Cladribine is to be orally administered as a liquid, a tablet or a capsule.

32. Cladribine for use as described herein, preferably as described in one or more of the numbered Sections above and/or below and more preferably for use according to one or more of the preceding Sections, wherein said Cladribine is to be orally administered as a tablet, preferably a tablet comprising about 10 mg of Cladribine.

33. Cladribine for use as described herein, preferably as described in one or more of the numbered Sections above and/or below and more preferably for use according to one or more of the preceding Sections, wherein said Cladribine is to be orally administered as a tablet comprising 10 mg of Cladribine in the form of a mixture of Cladribine, 2-hydroxypropyl-β-cyclodextrin and Cladribine-2-hydroxypropyl-3-cyclodextrin-complexes, wherein the weight ratio of Cladribine to 2-hydroxypropyl-β-cyclodextrin is between about 1:10 to about 1:16, preferably between 1:13 to 1:15.

34. A method of treating patients diagnosed to suffer from progressive forms of Multiple Sclerosis, said method comprising
   orally administering to said patients, preferably to each of said patients, a cumulative dose of Cladribine of about 3.5 mg/kg body weight, with a maximum deviation of +/−0.4 mg/kg, over 2 years (i.e. two treatment years), administered as one treatment course of about 1.75 mg/kg+/−0.2 mg/kg per year (i.e. per treatment year), wherein each treatment course consists of 2 treatment weeks, one at the beginning of the first month and one at the beginning of the second month of the respective treatment year.

35. The method as described herein, preferably as described in one or more of the numbered Sections above and/or below and more preferably as described in Section 34, wherein each treatment week consists of 4 or 5 days on which said patient receives 10 mg or 20 mg of Cladribine for oral administration, preferably as a single daily dose, depending on the body weight of the respective patient.

36. The method as described herein, preferably as described in one or more of the numbered Sections above and/or below and more preferably according to Section 35, wherein said patient receives the 10 mg or 20 mg of Cladribine for oral administration as a tablet or capsule, preferably a tablet or capsule containing 10 mg of Cladribine.

37. The method as described herein, preferably as described in one or more of the numbered Sections above and/or below and more preferably according to Section 36, wherein said patient receives the 10 mg or 20 mg of Cladribine for oral administration as a tablet or capsule comprising 10 mg of Cladribine in the form of a mixture of Cladribine, 2-hydroxypropyl-β-cyclodextrin and Cladribine-2-hydroxypropyl-β-cyclodextrin-complexes, wherein the weight ratio of Cladribine to 2-hydroxypropyl-β-cyclodextrin is between about 1:10 to about 1:16, preferably between 1:13 to 1:15.

38. The method as described herein, preferably as described in one or more of the numbered Sections above and/or below and more preferably according to one or more of Sections 34 to 37, wherein the progressive form of Multiple Sclerosis is Primary Progressive Multiple Sclerosis.

39. The method as described herein, preferably as described in one or more of the numbered Sections above and/or below and more preferably according to one or more of Sections 34 to 37, wherein the progressive form of Multiple Sclerosis is Secondary Progressive Multiple Sclerosis.

40. The method as described herein, preferably as described in one or more of the numbered Sections above and/or below and more preferably according to one or more of Sections 34 to 37, where the progressive form of Multiple Sclerosis is selected from the group consisting of Primary Progressive Multiple Sclerosis and Secondary Progressive Multiple Sclerosis, said method comprising orally administering to said patients a cumulative dose of Cladribine of about 3.5 mg/kg body weight over 2 years, administered as 1 treatment course of about 1.75 mg/kg, wherein each treatment course consists of 2 treatment weeks, one at the beginning of the first month and one at the beginning of the second month of the respective treatment year.

41. The method as described herein, preferably as described in one or more of the numbered Sections above and/or below and more preferably according to Section 40, wherein each treatment week consists of 4 or 5 days on which said patient receives 10 mg or 20 mg of Cladribine for oral administration, preferably as a single daily dose, and preferably depending on the body weight of the respective patient.

42. The method as described herein, preferably as described in one or more of the numbered Sections above and/or below and more preferably according to one or more of the preceding Sections, wherein said patients to be treated are between 18 and 65 years old, preferably inclusive.

43. The method as described herein, preferably as described in one or more of the numbered Sections above and/or below and more preferably according to one or more of the preceding Sections, wherein said patients to be treated are between 18 and 51 years old, preferably inclusive.

44. The method as described herein, preferably as described in one or more of the numbered Sections above and/or below and more preferably according to one or more of the preceding Sections, wherein said patients to be treated are between 12 and 51 years old, preferably inclusive.

45. The method as described herein, preferably as described in one or more of the numbered Sections above and/or below and more preferably according to one or more of the preceding Sections, wherein said patients to be treated are patients of female gender and/or patients of male gender. Since female patients are more often affected and/or often more severely affected by progressive forms of multiple sclerosis, it is a preferred aspect of the instant invention to treat female patients in this regard.

46. The method as described herein, preferably as described in one or more of the numbered Sections above and/or below and more preferably according to one or more of the preceding Sections, wherein said patients to be treated are treatment naïve to Cladribine and/or disease modifying drugs other than Cladribine.

47. The method as described herein, preferably as described in one or more of the numbered Sections above and/or below and more preferably according to one or more of the preceding Sections, wherein said patients our patients who previously received Cladribine and/or disease modifying drugs other than Cladribine. Preferably, in this regard the disease modifying drugs other than Cladribine comprise Interferon beta-1a, Beta interferon-1a (e.g. Avonex®, Rebif®).

48. The method as described herein, preferably as described in one or more of the numbered Sections above and/or below and more preferably according to one or more of the preceding Sections, wherein said patients to be treated additionally receive one or more disease modifying drugs other than Cladribine. Preferably, in this regard the disease modifying drugs other than Cladribine comprise Interferon beta-1a, Beta interferon-1a (e.g. Avonex®, Rebif®).

49. The method as described herein, preferably as described in one or more of the numbered Sections above and/or below and more preferably according to one or more of the preceding Sections, wherein said disease modifying drugs other than Cladribine are selected from the group consisting of:
Interferon beta-1a, Beta interferon-1a (e.g. Avonex®, Rebif®),
Interferon beta-1b, Beta interferon-1b (e.g. Betaferon®, Extavia®),
Peginterferon beta 1a (e.g. Plegridy®),
Alemtuzumab (e.g. Lemtrada®),
Daclizumab (e.g. Zinbryta®),
Dimethyl fumarate (e.g. Tecfidera®),
Fingolimod (e.g. Gilenya®),
Glatiramer acetate (e.g. Copaxone®),
Natalizumab (e.g. Tysabri®), and
Teriflunomide (e.g. Aubagio®).

50. The method as described herein, preferably as described in one or more of the numbered Sections above and/or below and more preferably according to one or more of the preceding Sections, wherein after the completion of said 2 years with said 2 treatment courses, no Cladribine is administered to the patients in the subsequent 1 or 2 years following the completion of said 2 years with said 2 treatment courses.

51. The method as described herein, preferably as described in one or more of the numbered Sections above and/or below and more preferably according to one or more of the preceding Sections, wherein to the patients having completed said 2 treatment courses of one year each, no further Cladribine treatment is required and/or administered to said patients in the subsequent years 3 and 4.

52. A method of treating patients suffering from progressive forms of Multiple Sclerosis, comprising orally administering to said patient tablets or capsules containing about 10 mg of Cladribine each, wherein said tablets or capsules are administered during a period called treatment year comprising the following regimen:
(i) a treatment course lasting 2 months, wherein Cladribine tablets or capsules are orally administered to the patient daily at a daily dose of 10 or 20 mg of Cladribine on 3 to up to 6 days each month, preferably on 4 or 5 days of each month, preferably in the 1$^{st}$ week of the respective month (each a treatment week);
(ii) followed by a Cladribine-free period lasting 10 months, preferably until the end of the 1$^{st}$ treatment year, wherein no Cladribine is administered to said patient;
wherein a patient having a bodyweight
in the range of 40 to less than 50 kg is or is to be administered
1) 4 tablets or capsules (40 mg of Cladribine) in the 1$^{st}$ month or treatment week of said treatment course,
2) 4 tablets or capsules (40 mg of Cladribine) in the 2$^{nd}$ month or treatment week of said treatment course,
in the range of 50 to less than 60 kg is or is to be administered
1) 5 tablets or capsules (50 mg of Cladribine) in the 1$^{st}$ month or treatment week of said treatment course, respectively,
2) 5 tablets or capsules (50 mg of Cladribine) in the 2$^{nd}$ month or treatment week of said treatment course,
in the range of 60 to less than 70 kg is or is to be administered
1) 6 tablets or capsules (60 mg of Cladribine) in the 1$^{st}$ month or treatment week of said treatment course,
2) 6 tablets or capsules (60 mg of Cladribine) in the 2$^{nd}$ month or treatment week of said treatment course,
in the range of 70 to less than 80 kg is or is to be administered
1) 7 tablets or capsules (70 mg of Cladribine) in the 1 month or treatment week of said treatment course,
2) 7 tablets or capsules (70 mg of Cladribine) in the 2$^{nd}$ month or treatment week of said treatment course,
in the range of 80 to less than 90 kg is or is to be administered
1) 8 tablets or capsules (80 mg of Cladribine) in the 1$^{st}$ month or treatment week of said treatment course,
2) 7 tablets or capsules (70 mg of Cladribine) in the 2$^{nd}$ month or treatment week of said treatment course,
in the range of 90 to less than 100 kg is or is to be administered
1) 9 tablets or capsules (90 mg of Cladribine) in the 1$^{st}$ month or treatment week of said treatment course,
2) 8 tablets or capsules (80 mg of Cladribine) in the 2$^{nd}$ month or treatment week of said treatment course,
in the range of 100 to less than 110 kg is or is to be administered
1) 10 tablets or capsules (100 mg of Cladribine) in the 1$^{st}$ month or treatment week of said treatment course,
2) 9 tablets or capsules (90 mg of Cladribine) in the 2$^{nd}$ month or treatment week of said treatment course,
in the range of 110 kg and above is or is to be administered
1) 10 tablets or capsules (100 mg of Cladribine) in the 1$^{st}$ month or treatment week of said treatment course,
2) 10 tablets or capsules (100 mg of Cladribine) in the 2$^{nd}$ month or treatment week of said treatment course.

53. The method as described herein, preferably as described in one or more of the numbered Sections above and/or below and more preferably according to Section 52, wherein the method further comprises at least one subsequent period called additional treatment year, wherein said additional treatment year is substantially identical, or preferably identical, to said regimen called treatment year. Preferably, Cladribine is administered during two or more treatment years, more preferably 2 treatment years, which are preferably adjacent treatment years that are preferably basically identical.
However, depending on the hematological state of the patient, it can become necessary or advantageous to separate two treatment years by a gap, i.e. a certain time where the previous treatment year is over and the foreseen next treatment year cannot or should not be started. Preferably and intentionally, Cladribine is not administered during such a gap. Typically, a gap in this regard lasts between 1 and 8 months, preferably between 1 and 6 months, more preferably between 1 and 3 months. Often, during such a gap, the hematological state of the patient is monitored in order to decide when the next treatment year can be started.

54. The method as described herein, preferably as described in one or more of the numbered Sections above and/or below and more preferably according to Section 53, wherein said additional treatment year is directly adjacent to said regimen called treatment year, or there is gap of 1 to 10 months in between the two treatment years. Typically, such a gap, if any, is induced by the hematological state of the patient at the end of the respective treatment year before the start of the new or subsequent treatment year. Sometimes, it can become necessary or advantageous to separate two treatment years by a gap, i.e. a certain time where the previous treatment year is over and the foreseen next treatment year cannot or should not be started. Preferably and intentionally, Cladribine is not administered during such a gap.

55. The method as described herein, preferably as described in one or more of the numbered Sections above and/or below and more preferably according to Section 52 or 53, wherein the method further comprises more than one subsequent periods called additional treatment year, preferably two additional treatment years, wherein all said additional treatment years are substantially identical, or preferably identical, and wherein said additional treatment years are directly adjacent to each other, or there is gap of 1 to 10 months in between at least two of said additional treatment years.

56. A method of treating patients suffering from progressive forms of Multiple Sclerosis, comprising orally administering to said patient tablets or capsules containing about 10 mg of Cladribine each, wherein said tablets or capsules are administered during a period called treatment year according comprising the following regimen:
   (i) a first treatment course lasting 2 months, wherein Cladribine tablets or capsules are orally administered daily at a daily dose of 10 or 20 mg of Cladribine on 3 to up to 6 days each month, preferably on 4 or 5 days of each month, preferably in the $1^{st}$ week of the respective month (treatment week);
   (ii) followed by a first Cladribine-free period lasting 10 months, preferably until the end of a first treatment year, wherein no Cladribine is administered to said patient;
   (iii) followed by a second treatment course lasting 2 months, wherein Cladribine tablets or capsules are orally administered daily at a daily dose of 10 or 20 mg of Cladribine on 3 to up to 6 days each month, preferably on 4 or 5 days of each month, preferably in the $1^{st}$ week of the respective month (treatment week); and
   (iv) followed by a second Cladribine-free period lasting 10 months, preferably until the end of a second treatment year, wherein no Cladribine is administered to said patient, and
wherein a patient having a bodyweight
   in the range of 40 to less than 50 kg is administered or is to be administered
1) 4 tablets or capsules (40 mg of Cladribine) in the $1^{st}$ month or treatment week of both the $1^{st}$ and the $2^{nd}$ treatment course, respectively,
2) 4 tablets or capsules (40 mg of Cladribine) in the $2^{nd}$ month or treatment week of both the $1^{st}$ and the $2^{nd}$ treatment course, respectively,
   in the range of 50 to less than 60 kg is administered or is to be administered
1) 5 tablets or capsules (50 mg of Cladribine) in the $1^{st}$ month or treatment week of both the $1^{st}$ and the $2^{nd}$ treatment course, respectively,
2) 5 tablets or capsules (50 mg of Cladribine) in the $2^{nd}$ month or treatment week of both the $1^{st}$ and the $2^{nd}$ treatment course, respectively,
   in the range of 60 to less than 70 kg is administered or is to be administered
1) 6 tablets or capsules (60 mg of Cladribine) in the $1^{st}$ month or treatment week of both the $1^{st}$ and the $2^{nd}$ treatment course, respectively,
2) 6 tablets or capsules (60 mg of Cladribine) in the $2^{nd}$ month or treatment week of both the $1^{st}$ and the $2^{nd}$ treatment course, respectively,
   in the range of 70 to less than 80 kg is administered or is to be administered
1) 7 tablets or capsules (70 mg of Cladribine) in the $1^{st}$ month or treatment week of both the $1^{st}$ and the $2^{nd}$ treatment course, respectively,
2) 7 tablets or capsules (70 mg of Cladribine) in the $2^{nd}$ month or treatment week of both the $1^{st}$ and the $2^{nd}$ treatment course, respectively,
   in the range of 80 to less than 90 kg is administered or is to be administered
1) 8 tablets or capsules (80 mg of Cladribine) in the $1^{st}$ month or treatment week of both the $1^{st}$ and the $2^{nd}$ treatment course, respectively,
2) 7 tablets or capsules (70 mg of Cladribine) in the $2^{nd}$ month or treatment week of both the 1 and the $2^{nd}$ treatment course, respectively,
   in the range of 90 to less than 100 kg is administered or is to be administered 1) 9 tablets or capsules (90 mg of Cladribine) in the $1^{st}$ month or treatment week of both the $1^{st}$ and the $2^{nd}$ treatment course, respectively,
2) 8 tablets or capsules (80 mg of Cladribine) in the $2^{nd}$ month or treatment week of both the 1a and the $2^{nd}$ treatment course, respectively,
   in the range of 100 to less than 110 kg is administered or is to be administered 1) 10 tablets or capsules (100 mg of Cladribine) in the $1^{st}$ month or treatment week of both the $1^{st}$ and the $2^{nd}$ treatment course, respectively.
2) 9 tablets or capsules (90 mg of Cladribine) in the $2^{nd}$ month or treatment week of both the 1 and the $2^{nd}$ treatment course, respectively,
   in the range of 110 kg and above is administered or is to be administered 1) 10 tablets or capsules (100 mg of Cladribine) in the $1^{st}$ month or treatment week of both the 1 and the $2^{nd}$ treatment course, respectively,
2) 10 tablets or capsules (100 mg of Cladribine) in the $2^{nd}$ month or treatment week of both the 1 and the $2^{nd}$ treatment course, respectively.

57. The method as described herein, preferably as described in one or more of the numbered Sections above and/or below and more preferably as described in the preceding Sections, wherein said 10 mg or 20 mg of Cladribine for oral administration are administered to the patient as a tablet or capsule comprising 10 mg of Cladribine in the form of a mixture of Cladribine, 2-hydroxypropyl-3-cyclodextrin and Cladribine-2-hydroxypropyl-β-cyclodextrin-complexes, wherein the weight ratio of Cladribine to 2-hydroxypropyl-β-cyclodextrin is between about 1:10 to about 1:16, preferably between 1:13 to 1:15.

58. The method as described herein, preferably as described in one or more of the numbered Sections above and/or below and more preferably according to one or more of the preceding Sections, wherein the progressive form of Multiple Sclerosis is Primary Progressive Multiple Sclerosis.
59. The method as described herein, preferably as described in one or more of the numbered Sections above and/or below and more preferably according to one or more of the preceding Sections, wherein the progressive form of Multiple Sclerosis is Secondary Progressive Multiple Sclerosis.
60. The method as described herein, preferably as described in one or more of the numbered Sections above and/or below and more preferably according to one or more of the preceding Sections, wherein said patients to be treated are between 18 and 51 years or 12 and 51 years old.
61. The method as described herein, preferably as described in one or more of the numbered Sections above and/or below and more preferably according to one or more of the preceding Sections, wherein said patients to be treated are patients of female gender and/or patients of male gender. Since female patients are more often affected and/or often more severely affected by progressive forms of multiple sclerosis, it is a preferred aspect of the instant invention to treat female patients in this regard.
62. The method as described herein, preferably as described in one or more of the numbered Sections above and/or below and more preferably according to one or more of the preceding Sections, wherein said patients to be treated are treatment naïve to Cladribine and/or disease modifying drugs other than Cladribine.
63. The method as described herein, preferably as described in one or more of the numbered Sections above and/or below and more preferably according to one or more of the preceding Sections, wherein said patients our patients who previously received Cladribine and/or disease modifying drugs other than Cladribine.
64. The method as described herein, preferably as described in one or more of the numbered Sections above and/or below and more preferably according to one or more of the preceding Sections, wherein said patients to be treated additionally receive one or more disease modifying drugs other than Cladribine.
65. The method as described herein, preferably as described in one or more of the numbered Sections above and/or below and more preferably according to one or more of the preceding Sections, wherein said disease modifying drugs other than Cladribine are selected from the group consisting of:
Interferon beta-1a, Beta interferon-1a (e.g. Avonex®, Rebif®),
Interferon beta-1b, Beta interferon-1b (e.g. Betaferon®, Extavia®),
Peginterferon beta 1a (e.g. Plegridy®),
Alemtuzumab (e.g. Lemtrada®),
Daclizumab (e.g. Zinbryta®),
Dimethyl fumarate (e.g. Tecfidera®),
Fingolimod (e.g. Gilenya®),
Glatiramer acetate (e.g. Copaxone®),
Natalizumab (e.g. Tysabri®), and
Teriflunomide (e.g. Aubagio®).
66. The method as described herein, preferably as described in one or more of the numbered Sections above and/or below and more preferably according to one or more of the preceding Sections, wherein after the completion of said 2 years with said 2 treatment courses, no Cladribine is administered to the patients in the subsequent 1 or 2 years following the completion of said 2 years with said 2 treatment courses.
67. The method as described herein, preferably as described in one or more of the numbered Sections above and/or below and more preferably according to one or more of the preceding Sections, wherein to the patients having completed said 2 treatment courses of one year each, no further Cladribine treatment is required and/or administered to said patients in the subsequent years 3 and 4.
68. The method as described herein, preferably as described in one or more of the numbered Sections above and/or below and more preferably according to one or more of the preceding Sections, wherein to the patients to be treated have been diagnosed to suffer from progressive forms Multiple Sclerosis, preferably selected from the group consisting of Primary Progressive Multiple Sclerosis and Secondary Progressive Multiple Sclerosis, preferably before the start of treatment according to the method.
69. The method as described herein, preferably as described in one or more of the numbered Sections above and/or below and more preferably according to one or more of the preceding Sections, wherein to the patients to be treated have been diagnosed Primary Progressive Multiple Sclerosis, preferably before the start of treatment according to the method.
70. The method as described herein, preferably as described in one or more of the numbered Sections above and/or below and more preferably according to one or more of the preceding Sections, wherein to the patients to be treated have been diagnosed Secondary Progressive Multiple Sclerosis, preferably before the start of treatment according to the method.
71. The method as described in one or more of the numbered Sections above and/or below and preferably according to one or more of the preceding Sections, wherein said Patient has High Disease Activity (HDA) and/or has been diagnosed High Disease Activity. Preferably, Cladribine is used according to the invention for patients that are already diagnosed High Disease Activity before the start of the treatment.

In another set of Sections, further embodiments are disclosed. The Sections may be combined with those above and below as long as there is no contradiction:
1. A method of treating a progressive form of Multiple Sclerosis, said method comprising: orally administering Cladribine to a patient in need thereof at fixed dose per patient, per body weight and per treatment year, wherein said fixed dose is in a range of 1.5 mg/kg to 4.0 mg/kg of body weight.
2. The method as described herein, preferably as described in one or more of the numbered Sections above and/or below and more preferably as described in Section 1, wherein said fixed dose is in a range of 1.5 mg/kg to 2.0 mg/kg.
3. The method as described herein, preferably as described in one or more of the numbered Sections above and/or below and more preferably as described in Section 1, wherein said fixed dose per patient is 1.75 mg/kg per treatment year with a maximum deviation of +/−0.2 mg/kg.
4. The method as described herein, preferably as described in one or more of the numbered Sections above and/or below and more preferably as described in Section 1, wherein said progressive form of multiple sclerosis comprises Primary Progressive Multiple Sclerosis and/or Secondary Progressive Multiple Sclerosis.
5. The method as described herein, preferably as described in one or more of the numbered Sections above and/or below and more preferably as described in Section 1, wherein said progressive form of Multiple Sclerosis is Primary Progressive Multiple Sclerosis.
6. The method as described herein, preferably as described in one or more of the numbered Sections above and/or below and more preferably as described in Section 1, wherein said progressive form of Multiple Sclerosis is Secondary Progressive Multiple Sclerosis.
7. The method as described herein, preferably as described in one or more of the numbered Sections above and/or below and more preferably as described in Section 1, wherein said patient has an age between 18 and 65 years.
8. The method as described herein, preferably as described in one or more of the numbered Sections above and/or below and more preferably as described in Section 1, wherein said patient has an age between 18 and 51 years.
9. The method as described herein, preferably as described in one or more of the numbered Sections above and/or below and more preferably as described in Section 1, wherein said patient has an age between 12 and 51 years.
10. The method as described herein, preferably as described in one or more of the numbered Sections above and/or below and more preferably as described in Section 1, wherein said Cladribine is orally administered to patients of female gender and/or to patients of male gender.
11. The method as described herein, preferably as described in one or more of the numbered Sections above and/or below and more preferably as described in Section 1, wherein said Patient has High Disease Activity (HDA) and/or has been diagnosed High Disease Activity.
12. The method as described herein, preferably as described in one or more of the numbered Sections above and/or below and more preferably as described in Section 1, wherein the patient is treatment naïve to Cladribine and/or disease modifying drugs other than Cladribine.
13. The method as described herein, preferably as described in one or more of the numbered Sections above and/or below and more preferably as described in Section 1, wherein the patient previously received Cladribine and/or one or more disease modifying drugs other than Cladribine.
14. The method as described herein, preferably as described in one or more of the numbered Sections above and/or below and more preferably as described in Section 1, wherein the patient is also receiving at least one disease modifying drug other than Cladribine.
15. The method as described herein, preferably as described in one or more of the numbered Sections above and/or below and more preferably as described in Section 14, wherein said at least one disease modifying drug other than Cladribine is at least one selected from the group consisting of:
Interferon beta-1a, Beta interferon-1a,
Interferon beta-1 b, Beta interferon-1b,
Peginterferon beta 1a,
Alemtuzumab,
Daclizumab,
Dimethyl fumarate,
Fingolimod,
Glatiramer acetate,
Natalizumab, and
Teriflunomide.
16. The method as described herein, preferably as described in one or more of the numbered Sections above and/or below and more preferably as described in Section 1, wherein said fixed dose is orally administered to said patient within two adjacent months within said treatment year.
17. The method as described herein, preferably as described in one or more of the numbered Sections above and/or below and more preferably as described in Section 16, wherein said fixed dose is orally administered to said patient within two adjacent months starting at the beginning of said treatment year.
18. The method as described herein, preferably as described in one or more of the numbered Sections above and/or below and more preferably as described in Section 16, wherein said fixed dose is orally administered to said patient within one week or two weeks of each of said two adjacent months.
19. The method as described herein, preferably as described in one or more of the numbered Sections above and/or below and more preferably as described in Section 16, wherein said fixed dose is orally administered to said patient within one week or two adjacent weeks at the beginning of each one of said two adjacent months.
20. The method as described herein, preferably as described in one or more of the numbered Sections above and/or below and more preferably as described in Section 16, wherein said fixed dose is orally administered to said patient within 2 to 7 days during said week, or within 2 to 7 days of each of said weeks.
21. The method as described herein, preferably as described in one or more of the numbered Sections above and/or below and more preferably as described in Section 16, wherein said fixed dose is orally administered to said patient within 4 to 5 days during said week, or within 4 to 5 days of each of said weeks.
22. The method as described herein, preferably as described in one or more of the numbered Sections above and/or below and more preferably as described in Section 1, wherein said Cladribine is orally administered for at least three treatment years.
23. The method as described herein, preferably as described in one or more of the numbered Sections above and/or below and more preferably as described in Section 1, wherein said Cladribine is orally administered to for at least two treatment years.
24. The method as described herein, preferably as described in one or more of the numbered Sections above and/or below and more preferably as described in Section 23, wherein two of said treatment years are either directly adjacent to each other, or are separated by a gap of from 1 to 10 months.
25. The method as described herein, preferably as described in one or more of the numbered Sections above and/or below and more preferably as described in Section 1,
wherein each treatment year comprises:
(i) a treatment period of 2 months at the beginning of said treatment year, wherein said fixed dose of Cladribine is orally administered on about 1 to about 7 days each month, said fixed dose being divided into daily doses of 5 to 20 mg of Cladribine, and (ii) a Cladribine-free period lasting 10 months, during which no Cladribine is administered.

26. The method as described herein, preferably as described in one or more of the numbered Sections above and/or below and more preferably as described in Section 1, wherein each treatment year comprises:
    (i) a treatment period of 2 months at the beginning of said treatment year, wherein said fixed dose of Cladribine is orally administered on 3 to 5 days each month at the beginning of each month, said fixed dose being divided into daily doses of 10 or 20 mg of Cladribine, and
    (ii) a Cladribine-free period lasting 10 months, during which no Cladribine is administered.

27. The method as described herein, preferably as described in one or more of the numbered Sections above and/or below and more preferably as described in Section 1, wherein said patient suffers from Primary Progressive Multiple Sclerosis and/or from Secondary Progressive Multiple Sclerosis, wherein said fixed dose per patient is 1.75 mg/kg per treatment year with a maximum deviation of +/−0.2 mg/kg, and wherein orally administering Cladribine comprises at least two treatment years.

28. The method as described herein, preferably as described in one or more of the numbered Sections above and/or below and more preferably as described in Section 1, wherein orally administering Cladribine comprises two treatment years that are substantially adjacent to either each other, or that are separated by a gap of 1 to 10 months.

29. The method as described herein, preferably as described in one or more of the numbered Sections above and/or below and more preferably as described in Section 1, wherein orally administering Cladribine comprises at least three treatment years,
    a) wherein said fixed dose per treatment year is from 0.75 mg/kg to 2.0 mg/kg,
    b) wherein the third treatment year comprises:
        (i) a treatment period of 1 month or 2 months at the beginning of said treatment year, wherein said fixed dose of Cladribine is orally administered on 3 to 5 days each month at the beginning of each month, said fixed dose being divided into daily doses of 10 or 20 mg of Cladribine, and
        (ii) a Cladribine-free period lasting 11 or 10 months respectively, during which no Cladribine is administered.

30. The method as described herein, preferably as described in one or more of the numbered Sections above and/or below and more preferably as described in Section 1, wherein orally administering Cladribine is in one or two treatment years, optionally plus an additional subsequent treatment year, followed by at least one year in which no Cladribine is administered to said patient.

31. The method as described herein, preferably as described in one or more of the numbered Sections above and/or below and more preferably as described in Section 1, wherein said Cladribine is orally administered as a liquid, a tablet, or a capsule.

32. The method as described herein, preferably as described in one or more of the numbered Sections above and/or below and more preferably as described in Section 1, wherein said Cladribine is orally administered as a tablet.

33. The method as described herein, preferably as described in one or more of the numbered Sections above and/or below and more preferably as described in Section 1, wherein said Cladribine is orally administered as a tablet comprising 10 mg of Cladribine in the form of a mixture of Cladribine, 2-hydroxypropyl-β-cyclodextrin and Cladribine-2-hydroxypropyl-β-cyclodextrin-complexes, wherein the weight ratio of Cladribine to 2-hydroxypropyl-β-cyclodextrin is between about 1:10 to about 1:16.

34. A method of treating a patient diagnosed as suffering from a progressive form of Multiple Sclerosis, said method comprising orally administering to said patient a cumulative dose of Cladribine of about 3.5 mg/kg body weight, with a maximum deviation of +/−0.4 mg/kg, over 2 years, administered in each year as 1 treatment course of about 1.75 mg/kg+/−0.2 mg/kg per year, wherein each treatment course consists of 2 treatment weeks, one at the beginning of the first month and one at the beginning of the second month of the respective treatment year.

35. The method as described herein, preferably as described in one or more of the numbered Sections above and/or below and more preferably as described in Section 34, wherein each treatment week consists of 4 or 5 days on which said patient receives 10 mg or 20 mg of Cladribine for oral administration, depending on the body weight of the patient.

36. The method as described herein, preferably as described in one or more of the numbered Sections above and/or below and more preferably as described in Section 35, wherein said patient receives the 10 mg or 20 mg of Cladribine for oral administration as a tablet or capsule.

37. The method as described herein, preferably as described in one or more of the numbered Sections above and/or below and more preferably as described in Section 36, wherein said patient receives the 10 mg or 20 mg of Cladribine for oral administration as a tablet or capsule comprising 10 mg of Cladribine in the form of a mixture of Cladribine, 2-hydroxypropyl-β-cyclodextrin and Cladribine-2-hydroxypropyl-β-cyclodextrin-complexes, wherein the weight ratio of Cladribine to 2-hydroxypropyl-β-cyclodextrin is between about 1:10 to about 1:16.

38. The method as described herein, preferably as described in one or more of the numbered Sections above and/or below and more preferably as described in Section 34, wherein the progressive form of Multiple Sclerosis is Primary Progressive Multiple Sclerosis.

39. The method as described herein, preferably as described in one or more of the numbered Sections above and/or below and more preferably as described in Section 34, wherein the progressive form of Multiple Sclerosis is Secondary Progressive Multiple Sclerosis.

40. The method as described herein, preferably as described in one or more of the numbered Sections above and/or below and more preferably as described in Section 34, where the progressive form of Multiple Sclerosis is selected from the group consisting of Primary Progressive Multiple Sclerosis and Secondary Progressive Multiple Sclerosis.

41. The method as described herein, preferably as described in one or more of the numbered Sections above and/or below and more preferably as described in Section 40, wherein each treatment week consists of 4 or 5 days on which said patient receives 10 mg or 20 mg of Cladribine for oral administration.

42. The method as described herein, preferably as described in one or more of the numbered Sections above and/or below and more preferably as described in Section 34, wherein said patient is between 18 and 65 years old.

43. The method as described herein, preferably as described in one or more of the numbered Sections above and/or below and more preferably as described in Section 34, wherein said patient is between 18 and 51 years old.

44. The method as described herein, preferably as described in one or more of the numbered Sections above and/or below and more preferably as described in Section 34, wherein said patient is between 12 and 51 years old.

45. The method as described herein, preferably as described in one or more of the numbered Sections above and/or below and more preferably as described in Section 34, wherein patients to be treated are patients of female gender and/or patients of male gender.

46. The method as described herein, preferably as described in one or more of the numbered Sections above and/or below and more preferably as described in Section 34, wherein the patient is treatment naïve to Cladribine and/or disease modifying drugs other than Cladribine.

47. The method as described herein, preferably as described in one or more of the numbered Sections above and/or below and more preferably as described in Section 34, wherein said patient previously received Cladribine and/or one or more disease modifying drugs other than Cladribine.

48. The method as described herein, preferably as described in one or more of the numbered Sections above and/or below and more preferably as described in Section 34, wherein the patient additionally receives at least one disease modifying drug other than Cladribine.

49. The method as described herein, preferably as described in one or more of the numbered Sections above and/or below and more preferably as described in Section 48, wherein said at least one disease modifying drug other than Cladribine is at least one selected from the group consisting of:
Interferon beta-1a, Beta interferon-1a,
Interferon beta-1b, Beta interferon-1b,
Peginterferon beta 1a,
Alemtuzumab,
Daclizumab,
Dimethyl fumarate,
Fingolimod,
Glatiramer acetate,
Natalizumab, and
Teriflunomide.

50. The method as described herein, preferably as described in one or more of the numbered Sections above and/or below and more preferably as described in Section 34, wherein after the completion of said 2 years with said 2 treatment courses, no Cladribine is administered to the patients in the subsequent 1 or 2 years following the completion of said 2 years with said 2 treatment courses.

51. The method as described herein, preferably as described in one or more of the numbered Sections above and/or below and more preferably as described in Section 34, wherein after said 2 treatment courses of one year each, no further Cladribine treatment is administered to said patient in the subsequent years 3 and 4.

52. A method of treating a patient suffering from a progressive form of Multiple Sclerosis, comprising orally administering to said patient tablets or capsules containing about 10 mg of Cladribine each, wherein said tablets or capsules are administered during a treatment year comprising the following regimen:
(i) a treatment course lasting 2 months, wherein Cladribine tablets or capsules are orally administered daily at a daily dose of 10 or 20 mg of Cladribine on a treatment week of from 3 to up to 6 days each month;
(ii) followed by a Cladribine-free period lasting 10 months wherein no Cladribine is administered to said patient;
wherein patients having a bodyweight
in the range of 40 to less than 50 kg are administered
1) 4 tablets or capsules (40 mg of Cladribine) in the $1^{st}$ treatment week of said treatment course,
2) 4 tablets or capsules (40 mg of Cladribine) in the $2^{nd}$ treatment week of said treatment course;
in the range of 50 to less than 60 kg are administered
1) 5 tablets or capsules (50 mg of Cladribine) in the $1^{st}$ treatment week of said treatment course, respectively,
2) 5 tablets or capsules (50 mg of Cladribine) in the $2^{nd}$ treatment week of said treatment course;
in the range of 60 to less than 70 kg are administered
1) 6 tablets or capsules (60 mg of Cladribine) in the $1^{st}$ treatment week of said treatment course,
2) 6 tablets or capsules (60 mg of Cladribine) in the $2^{nd}$ treatment week of said treatment course;
in the range of 70 to less than 80 kg are administered
1) 7 tablets or capsules (70 mg of Cladribine) in the $1^{st}$ treatment week of said treatment course,
2) 7 tablets or capsules (70 mg of Cladribine) in the $2^{nd}$ treatment week of said treatment course;
in the range of 80 to less than 90 kg are administered
1) 8 tablets or capsules (80 mg of Cladribine) in the 1 treatment week of said treatment course,
2) 7 tablets or capsules (70 mg of Cladribine) in the $2^{nd}$ treatment week of said treatment course;
in the range of 90 to less than 100 kg are administered
1) 9 tablets or capsules (90 mg of Cladribine) in the $1^{st}$ treatment week of said treatment course,
2) 8 tablets or capsules (80 mg of Cladribine) in the $2^{nd}$ treatment week of said treatment course;
in the range of 100 to less than 110 kg are administered
1) 10 tablets or capsules (100 mg of Cladribine) in the $1^{st}$ treatment week of said treatment course,
2) 9 tablets or capsules (90 mg of Cladribine) in the $2^{nd}$ treatment week of said treatment course; or
in the range of 110 kg and above are administered
1) 10 tablets or capsules (100 mg of Cladribine) in the $1^{st}$ treatment week of said treatment course,
2) 10 tablets or capsules (100 mg of Cladribine) in the $2^{nd}$ treatment week of said treatment course.

53. The method as described herein, preferably as described in one or more of the numbered Sections above and/or below and more preferably as described in Section 52, wherein the method further comprises at least one subsequent additional treatment year, wherein said additional treatment year is substantially identical to said treatment year.

54. The method as described herein, preferably as described in one or more of the numbered Sections above and/or below and more preferably as described in Section 53, wherein said additional treatment year is directly adjacent to said treatment year, or wherein the method comprises a gap of 1 to 10 months in between the two treatment years.

55. The method as described herein, preferably as described in one or more of the numbered Sections above and/or below and more preferably as described in Section 52, wherein the method further comprises two additional treatment years, wherein all said additional treatment years are substantially identical, and wherein said additional treatment years are directly adjacent to each other, or wherein the method comprises a gap of 1 to 10 months in between at least two of said additional treatment years.

56. A method of treating a patient suffering from a progressive form of Multiple Sclerosis, said method comprising orally administering to said patient tablets or capsules containing about 10 mg of Cladribine each, wherein said tablets or capsules are administered during two treatment years comprising the following regimen:
   (i) a first treatment course lasting 2 months, wherein Cladribine tablets or capsules are orally administered daily at a daily dose of 10 or 20 mg of Cladribine on 3 to up to 6 days each month;
   (ii) followed by a first Cladribine-free period lasting 10 months, wherein no Cladribine is administered to said patient;
   (iii) followed by a second treatment course lasting 2 months, wherein Cladribine tablets or capsules are orally administered daily at a daily dose of 10 or 20 mg of Cladribine on 3 to up to 6 days each month; and
   (iv) followed by a second Cladribine-free period lasting 10 months, wherein no Cladribine is administered to said patient, and
wherein patients having a bodyweight
   in the range of 40 to less than 50 kg are administered
      1) 4 tablets or capsules (40 mg of Cladribine) in the $1^{st}$ treatment week of both the $1^{st}$ and the $2^{nd}$ treatment course, respectively,
      2) 4 tablets or capsules (40 mg of Cladribine) in the $2^{nd}$ treatment week of both the $1^{st}$ and the $2^{nd}$ treatment course, respectively:
   in the range of 50 to less than 60 kg are administered
      1) 5 tablets or capsules (50 mg of Cladribine) in the $1^{st}$ treatment week of both the $1^{st}$ and the $2^{nd}$ treatment course, respectively,
      2) 5 tablets or capsules (50 mg of Cladribine) in the $2^{nd}$ treatment week of both the $1^{st}$ and the $2^{nd}$ treatment course, respectively:
   in the range of 60 to less than 70 kg are administered
      1) 6 tablets or capsules (60 mg of Cladribine) in the $1^{st}$ treatment week of both the $1^{st}$ and the $2^{nd}$ treatment course, respectively,
      2) 6 tablets or capsules (60 mg of Cladribine) in the $2^{nd}$ treatment week of both the 1a and the $2^{nd}$ treatment course, respectively;
   in the range of 70 to less than 80 kg are administered
      1) 7 tablets or capsules (70 mg of Cladribine) in the $1^{st}$ treatment week of both the 1 and the $2^{nd}$ treatment course, respectively,
      2) 7 tablets or capsules (70 mg of Cladribine) in the $2^{nd}$ treatment week of both the $1^{st}$ and the $2^{nd}$ treatment course, respectively;
   in the range of 80 to less than 90 kg are administered
      1) 8 tablets or capsules (80 mg of Cladribine) in the $1^{st}$ treatment week of both the $1^{st}$ and the $2^{nd}$ treatment course, respectively,
      2) 7 tablets or capsules (70 mg of Cladribine) in the $2^{nd}$ treatment week of both the $1^{st}$ and the $2^{nd}$ treatment course, respectively;
   in the range of 90 to less than 100 kg are administered
      1) 9 tablets or capsules (90 mg of Cladribine) in the $1^{st}$ treatment week of both the $1^{st}$ and the $2^{nd}$ treatment course, respectively,
      2) 8 tablets or capsules (80 mg of Cladribine) in the $2^{nd}$ treatment week of both the 1 and the $2^{nd}$ treatment course, respectively;
   in the range of 100 to less than 110 kg are administered
      1) 10 tablets or capsules (100 mg of Cladribine) in the $1^{st}$ treatment week of both the 1 and the $2^{nd}$ treatment course, respectively,
      2) 9 tablets or capsules (90 mg of Cladribine) in the $2^{nd}$ treatment week of both the 1 and the $2^{nd}$ treatment course, respectively; or
   in the range of 110 kg and above are administered
      1) 10 tablets or capsules (100 mg of Cladribine) in the $1^{st}$ treatment week of both the 1 and the $2^{nd}$ treatment course, respectively,
      2) 10 tablets or capsules (100 mg of Cladribine) in the $2^{nd}$ treatment week of both the $1^{st}$ and the $2^{nd}$ treatment course, respectively.

57. The method as described herein, preferably as described in one or more of the numbered Sections above and/or below and more preferably as described in Section 56, wherein said 10 mg or 20 mg of Cladribine for oral administration are administered to the patient as a tablet or capsule comprising 10 mg of Cladribine in the form of a mixture of Cladribine, 2-hydroxypropyl-β-cyclodextrin and Cladribine-2-hydroxypropyl-β-cyclodextrin-complexes, wherein the weight ratio of Cladribine to 2-hydroxypropyl-β-cyclodextrin is between about 1:10 to about 1:16.

58. The method as described herein, preferably as described in one or more of the numbered Sections above and/or below and more preferably as described in Section 56, wherein the progressive form of Multiple Sclerosis is Primary Progressive Multiple Sclerosis.

59. The method as described herein, preferably as described in one or more of the numbered Sections above and/or below and more preferably as described in Section 56, wherein the progressive form of Multiple Sclerosis is Secondary Progressive Multiple Sclerosis.

60. The method as described herein, preferably as described in one or more of the numbered Sections above and/or below and more preferably as described in Section 56, wherein the patient is between 12 and 51 years old.

61. The method as described herein, preferably as described in one or more of the numbered Sections above and/or below and more preferably as described in Section 56, wherein patients to be treated are patients of female gender and/or patients of male gender.

62. The method as described herein, preferably as described in one or more of the numbered Sections above and/or below and more preferably as described in Section 56, wherein the patient is treatment naïve to Cladribine and/or disease modifying drugs other than Cladribine.
63. The method as described herein, preferably as described in one or more of the numbered Sections above and/or below and more preferably as described in Section 56, wherein the patient previously received Cladribine and/or disease modifying drugs other than Cladribine.
64. The method as described herein, preferably as described in one or more of the numbered Sections above and/or below and more preferably as described in Section 56, wherein the patient additionally receives at least one disease modifying drug other than Cladribine.
65. The method as described herein, preferably as described in one or more of the numbered Sections above and/or below and more preferably as described in Section 64, wherein said at least one disease modifying drug other than Cladribine is at least one selected from the group consisting of:
Interferon beta-1a, Beta interferon-1a,
Interferon beta-1b, Beta interferon-1b,
Peginterferon beta 1a,
Alemtuzumab,
Daclizumab,
Dimethyl fumarate,
Fingolimod,
Glatiramer acetate,
Natalizumab, and
Teriflunomide.
66. The method as described herein, preferably as described in one or more of the numbered Sections above and/or below and more preferably as described in Section 56, wherein after the completion of said 2 years with said 2 treatment courses, no Cladribine is administered to the patients in the subsequent 1 or 2 years following the completion of said 2 years with said 2 treatment courses.
67. The method as described herein, preferably as described in one or more of the numbered Sections above and/or below and more preferably as described in Section 56, wherein to the patients having completed said 2 treatment courses of one year each, no further Cladribine treatment is administered to said patients in the subsequent years 3 and 4.
68. The method as described herein, preferably as described in one or more of the numbered Sections above and/or below and more preferably as described in Section 56, wherein the progressive form of Multiple Sclerosis is selected from the group consisting of Primary Progressive Multiple Sclerosis and Secondary Progressive Multiple Sclerosis.
69. The method as described herein, preferably as described in one or more of the numbered Sections above and/or below and more preferably as described in Section 56, wherein the progressive form of Multiple Sclerosis is Primary Progressive Multiple Sclerosis.
70. The method as described herein, preferably as described in one or more of the numbered Sections above and/or below and more preferably as described in Section 56, wherein the progressive form of Multiple Sclerosis is Secondary Progressive Multiple Sclerosis.
71. The method as described herein, preferably as described in one or more of the numbered Sections above and/or below and more preferably as described in Section 56, wherein said Patient has High Disease Activity (HDA) and/or has been diagnosed High Disease Activity.

Alternatively, preferred are methods of treatment as described herein and especially as described in the two sets of sections numbered 1 to 71 above, wherein one or more of the below given preferred features are realized:
the induction period lasts up to about 2 months;
the Cladribine free period (ii) lasts about 10 months, about 12 months, about 14 months or about 16 months, preferably about 10 months;
the Cladribine free period (iv) lasts at least 10 months, at least 14 months, at least 22 months or at least 32 months, or the Cladribine free period (iv) lasts about 10 months, about 14 months, about 22 months or about 32 months;
the total dose of Cladribine reached at the end of the induction period is about 1.75 mg/kg, or the total dose of Cladribine reached at the end of the induction period is about 3.5 mg/kg, preferably it is about 1.75 mg/kg;
the total dose of Cladribine reached at the end of the maintenance period is about 1.75 mg/kg, or the total dose of Cladribine reached at the end of the maintenance period is about 3.5 mg/kg, preferably it is about 1.75 mg/kg;
the total dose of Cladribine reached at the end of the induction period is about 1.75 mg/kg, and the total dose of Cladribine reached at the end of the maintenance period is about 1.75 mg/kg;
the cumulative total dose of Cladribine reached after the end of both the induction period and the maintenance period is about 3.5 mg/kg;
the Cladribine-free period (ii) lasts up to about 10 months, or the Cladribine-free as East End does finish Isa period (ii) lasts at least about 10 months;
the Cladribine-free period (ii) lasts at least about 10 months, typically 10 to 13 months, and especially about 10 months;
the Cladribine-free (iv) period lasts at least about 8 months, more preferably at least about 10 months, even more preferably at least 18 months and especially at least 24 months
the Cladribine-free period (iv) lasts at least about 10 months or at least 10 months;
the Cladribine-free (iv) period lasts at least about 8 months, more preferably at least about 10 months, even more preferably at least 18 months and especially at least 24 months.
the Cladribine-free period (iv) lasts up to about 34 months, up to 20 months, up to 13 months or up to 10 months;
the Cladribine-free period (ii) and/or (iv) is free of any administration, more preferably free of any administration regarding MS therapy;
the maintenance period lasts up to about 4 months, or up to about 3 months, or up to about 2 months, preferably up to about 2 months;
the maintenance therapy lasts about two months;
the steps (iii) to (iv) are repeated at least one or two times.

It is understood that two or more of the above given features are only to be combined if they are not contradicting each other.

Definitions

The "total dose" or "cumulative dose" preferably refers to the total dose of Cladribine administered during the treatment, i.e. the dose reached at the end of the treatment that is calculated by adding the daily doses. For example, the total dose of Cladribine corresponding to a treatment of 0.7 mg/kg Cladribine per day for 5 days is 3.5 mg/kg or the total dose of Cladribine corresponding to a treatment of 0.35 mg/kg Cladribine per day for 5 days is 1.7 mg/kg.

"The total effective dose" or "cumulative effective dose" preferably refers to the bioavailable dose of Cladribine after a given administration period, i.e. the bioavailable dose reached at the end of the treatment that is calculated by adding the daily doses reduced by the bioavailability coefficient. For example, the total effective dose of Cladribine corresponding to a treatment of 0.7 mg/kg Cladribine per day for 5 days wherein the bioavailability of Cladribine is of about 40% is 1.4 mg/kg or the total effective dose of Cladribine corresponding to a treatment of 0.35 mg/kg Cladribine per day for 5 days wherein the bioavailability of Cladribine is of about 40% is 0.7 mg/kg.

Typically, the bioavailability of Cladribine or of a Cladribine formulation used in the context of this invention is from about 30% to about 90%, preferably from about 40% to about 60%, such as about 50%.

Cladribine may be orally administered to each patient at a certain dose that is calculated per patient, per body weight and per treatment year, wherein said dose or said certain dose is selected from the range of 1.5 mg/kg to 4.0 mg/kg. Preferably, a dose that is calculated per patient, per body weight of the patient and per treatment year is referred to as a "fixed dose".

"A week" preferably refers to a period of time of or about 5, about 6 or about 7 days. It may be about 5-8 days.

"A month" preferably refers to a period of time of or about 28, about 29, about 30 or about 31 days. It may be about 26-33 days.

"Treatment" as used herein preferably comprises the sequential succession of an "induction treatment" and at least a "maintenance treatment". Typically, a treatment according to the invention comprises an "induction treatment" and about one or about two or about three maintenance treatments, preferably one or two maintenance treatments, more preferably one maintenance treatment.

Typically, a treatment according to the invention is of about 2 years (about 24 months) or about 3 years (about 36 months) or about 4 years (about 48 months). Following completion of 2 treatment courses, further Cladribine treatment in Year 3 and/or Year 4 may not be necessary but may be considered as an option in PPMS and/or SPMS.

An "Induction Treatment" preferably consists in the sequential succession of (i) an induction period wherein the Cladribine or the Cladribine pharmaceutical preparation of the invention is orally administered and (ii) a Cladribine-free period. An induction period preferably lasts up to about 4 months or up to about 3 month or up to about 2 months. For example, an induction period lasts for about 2 to about 4 months. An induction period preferably consists in the oral administration of Cladribine or a pharmaceutical preparation thereof during about 1 to about 7 days each month.

A "Cladribine-free period" preferably is a period wherein no Cladribine is administered to the patient. During a Cladribine-free period, the patient can be free of any administration or be dosed with a placebo-pill, or another drug except Cladribine. A Cladribine-free period preferably lasts up to about 10 months or up to about 9 months or up to about 8 months. For example, a Cladribine-free period lasts from about 8 to about 10 months, typically at least of about 8 months. More preferably, a Cladribine-free period lasts at least about 8 months, at least about 9 months or at least about 10 months. Especially preferably, a Cladribine-free period lasts about 10 months. However, if recommended by the physician, the Cladribine-free period can preferably also be extended, preferably by 1-3 months. The durations given for the Cladribine-free period in this section are especially preferred for the Cladribine-free period between the Induction Treatment and the Maintenance Treatment. With regard to the Cladribine-free period after a Maintenance Treatment, duration of at least about 10 months, at least 22 months or at least 34 months is preferred. Typically, a Cladribine-free period after a Maintenance Treatment will be between about 10 months and about 22 months, between.

A "Maintenance Treatment" preferably consists in the sequential succession of (i) a maintenance period wherein the Cladribine or the Cladribine pharmaceutical preparation of the invention is orally administered at a lower or equal dose than the Cladribine dose orally administered during the induction treatment and (ii) a Cladribine-free period. A maintenance period preferably lasts for up to about 4 months, or up to about 3 months, or up to about 2 months, preferably up to about 2 months. For example, a maintenance period lasts for about 2 to about 4 months, preferably for about 2 months. A maintenance period consists in the oral administration of Cladribine or of a pharmaceutical preparation thereof during about 1 to about 7 days each month.

Within the context of this invention, the beneficial effect, preferably including but not limited to one or more selected from an attenuation, reduction, decrease or diminishing of the pathological development after onset of the disease, may be seen after one or more a "treatments", after an "induction treatment", after a "maintenance treatment" or during a Cladribine-free period.

"Daily dose" preferably refers to the total dose of Cladribine orally administered to the patient each day of administration. The daily dose can be reached through a single or several administrations per day, such as for example once a day, twice a day or three times a day. Preferably, it is reached or achieved by single administration per day, preferably consisting of one or more tablets or capsules, preferably tablets or capsules as described herein.

Preferably, the dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired. Preferably, the dosage or dose of administered will vary only on one factor, i.e. body weight of the respective individual, patient or human. A dose of about 1.75 mg per kg of body weight of the respective individual, patient, or human is preferred for each Induction Period and each Maintenance Period. Preferably, said dose of about 1.75 mg per kg of body weight of the includes a deviation of plus or minus 10%, preferably a deviation of plus or minus 5%. Typically, this deviation is caused by the dosage strength of the respective Cladribine-containing dosage form, e.g. 10 mg tablets or capsules, to be administered to the respective individual, patient or human, and/or the weight ranges the respective individuals, patients or humans are preferably divided in, e.g. weight ranges of about 5 kg or about 10 kg, in order to provide sufficient guidance and practicability for administering such a fixed dosing per body weight of that respective individual, patient or human.

Patients suffering from MS can be defined for example as having clinically definite or laboratory-definite MS according to Schumacher or Poser criteria (Schumacher et al., 1965, *Ann. NY Acad. Sci.* 1965; 122:552-568; Poser et al., 1983, *Ann. Neurol.* 13(3): 227-31).

"Relapses" preferably involve neurologic problems that occur over a short period, typically days but sometimes as short as hours or even minutes. These attacks most often involve motor, sensory, visual or coordination problems early in the disease. Later, bladder, bowel, sexual and cognitive problems may be shown. Sometimes the attack onset occurs over several weeks. Typical MS relapse involves a period of worsening, with development of neurological deficits, then a plateau, in which the patient is not getting any better but also not getting any worse followed by a recovery period. Recovery usually begins within a few weeks.

"Efficacy" of a treatment according to the invention can be preferably measured based on changes in the course of disease in response to a use according to the invention. For example, treatment of MS efficacy can be measured by the frequency of relapses in RRMS and the presence or absence of new lesions in the CNS as detected using methods such as MRI technique (Miller et al., 1996, *Neurology*, 47(Suppl 4): S217; Evans et al., 1997, *Ann. Neurology*, 41:125-132).

Preferably, the observation of the reduction and/or suppression of MRI $T_1$ gadolinium-enhanced lesions (thought to represent areas of active inflammation) gives a primary efficacy variable.

Secondary efficacy variables preferably include MRI $T_1$ enhanced brain lesion volume, MRI $T_1$ enhanced lesion number, MRI $T_2$ lesion volume (thought to represent total disease burden, i.e. demyelination, gliosis, inflammation and axon loss), MRI $T_1$ enhanced hypointense lesion volume (thought to represent primarily demyelination and axon loss), time-to-progression of MS, frequency and severity of exacerbations and time-to-exacerbation, Expanded Disability Status Scale score and Scripps Neurologic Rating Scale (SNRS) score (Sipe et al., 1984. *Neurology*, 34, 1368-1372). Methods of early and accurate diagnosis of multiple sclerosis and of following the disease progression are described in Mattson, 2002, *Expert Rev. Neurotherapeutics*, 319-328.

Degree of disability of MS patients can be for example measured by Kurtzke Expanded Disability Status Scale (EDSS) score (Kurtzke, 1983, *Neurology*, 33, 1444-1452). Typically, a decrease in EDSS score corresponds to an improvement in the disease and conversely, an increase in EDSS score corresponds to a worsening of the disease.

Patients with "high disease activity" (HDA) include
patients with 1 relapse in the previous year and at least 1 T1 Gd+ lesion or 9 or more T2 lesions, while on therapy with other DMDs (Disease Modifying Drugs), patients with 2 or more relapses in the previous year, whether on DMD treatment or not.

Cladribine (2-CdA)

2-CdA and its pharmacologically acceptable salts may be used in the practice of this invention.

Cladribine can be formulated in any pharmaceutical preparation suitable for oral administration. Representative oral formulations of 2-CdA are described in (WO 96/19230; WO 96/19229; U.S. Pat. Nos. 6,194,395; 5,506,214; WO 2004/087100; WO 2004/087101), the contents of which are incorporated herein by reference. Examples of ingredients for oral formulations are given below.

Processes for preparing 2-CdA are well known in the art. For example, the preparation of 2-CdA is described in (EP 173.059; WO 04/028462; WO 04/028462; U.S. Pat. No. 5,208,327; WO 00/64918) and Robins et al., *J. Am. Chem. Soc.*, 1984, 106: 6379. Alternatively, pharmaceutical preparations of 2-CdA may be purchased from Bedford Laboratories, Bedford, Ohio.

Oral administration of Cladribine may be in capsule, tablet, oral suspension, or syrup form. The tablet or capsules may contain from about 3 to 500 mg of Cladribine. Preferably they may contain about 3 to about 10 mg of Cladribine, more preferably about 3, about 5 or about 10 mg of Cladribine. The capsules may be gelatin capsules and may contain, in addition to Cladribine in the quantity indicated above, a small quantity, for example less than 5% by weight, magnesium stearate or another excipient. Tablets may contain the foregoing amount of the compound (Cladribine) and a binder, which may be a gelatin solution, a starch paste in water, polyvinyl alcohol in water, etc. with a typical sugar coating. Alternatively, tablets may contain the foregoing amount of the compound (Cladribine) and a binder, comprising one or more cyclodextrines, or consisting of one or more cyclodextrines. Preferably, said binder is contained in said tablet in an amount of 50% or more, in an amount of 60% or more, in an amount of 70% or more, in an amount of 80% or more or in an amount of 90% or more, e.g. in an amount of about 60%, in an amount of about 70%, in an amount of about 80%, in an amount of about 90% or in an amount of about 95%, based on the total weight of the tablet. Additionally, tablets may contain one or more other excipients in an amount of less than 50% and preferably less than 40%, e.g. in an amount of about 400, in an amount of about 30%, in an amount of about 20%, or in an amount of about 10%, based on the total weight of the tablet. Preferably, said one or more cyclodextrines comprise 2-hydroxypropyl-β-cyclodextrin, or essentially consist of 2-hydroxypropyl-β-cyclodextrin.

Compositions

Compositions may further comprise one or more pharmaceutically acceptable additional ingredient(s) such as alum, stabilizers, antimicrobial agents, buffers, coloring agents, flavoring agents, adjuvants, and the like.

Compositions may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate). Tablets may be coated according to methods well known in the art.

Compositions may also be liquid formulations including, but not limited to, aqueous or oily suspensions, solutions, emulsions, syrups, and elixirs. The compositions may also be formulated as a dry product for constitution with water or other suitable vehicle before use. Such liquid preparations may contain additives including, but not limited to, suspending agents, emulsifying agents, nonaqueous vehicles and preservatives. Suspending agent include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

Combination

Preferably, Cladribine can be administered alone or in combination with IFN-beta, prophylactically or therapeutically to an individual prior to, simultaneously or sequentially with other therapeutic regimens or agents (e.g. multiple drug regimens), in a therapeutically effective amount, especially therapeutic agents for the treatment of multiple sclerosis. Active agents that are administered simultaneously with other therapeutic agents can be administered in the same or different compositions and in the same or different routes of administration.

For example, when Cladribine is administered in combination with IFN-beta, IFN-beta is preferably administered during the Cladribine-free period.

Alternatively, when Cladribine is administered in combination with IFN-beta, IFN-beta is preferably administered after the "treatment" according to the invention.

The term "interferon-beta (IFN-β)", as used herein, is preferably intended to include fibroblast interferon in particular of human origin, as obtained by isolation from biological fluids or as obtained by DNA recombinant techniques from prokaryotic or eukaryotic host cells, as well as its salts, functional derivatives, variants, analogues and active fragments.

IFN-β preferably suitable for use accordance with the present invention is commercially available e.g. as Rebif® (Serono), Avonex® (Biogen) or Betaferon® (Schering). The use of interferons of human origin is also preferred in accordance with the present invention. The term interferon, as used herein, is intended to encompass salts, functional derivatives, variants, analogues and active fragments thereof.

Rebif® (recombinant human interferon-β) is one of the latest developments in interferon therapy for multiple sclerosis (MS) and is believed to represent a significant advance in MS therapy. Rebif® is interferon (IFN)-beta 1a, produced from mammalian cell lines. It was established that interferon beta-1a given subcutaneously three times per week is efficacious in the treatment of Relapsing-Remitting Multiple Sclerosis (RRMS). Interferon beta-1a can have a positive effect on the long-term course of MS by reducing number and severity of relapses and reducing the burden of the disease and disease activity as measured by MRI.

If applicable, the dosing of IFN-β in the treatment of progressive Forms of MS according to the invention preferably depends on the type of IFN-β used.

If applicable in accordance with the present invention, in case where IFN is recombinant IFN-β1b produced in *E. Coli*, commercially available under the trademark Betaseron®, it may preferably be administered sub-cutaneously every second day at a dosage of about of 250 to 300 µg or 8 MIU to 9.6 MIU per person.

If applicable in accordance with the present invention, in case where IFN is recombinant IFN-β1a, produced in Chinese Hamster Ovary cells (CHO cells), commercially available under the trademark Avonex®, it may preferably be administered intra-muscularly once a week at a dosage of about of 30 µg to 33 µg or 6 MIU to 6.6 MIU per person.

In accordance with the present invention, when IFN is recombinant IFN-β1a, produced in Chinese Hamster Ovary cells (CHO cells), commercially available under the trademark Rebif®, it may preferably be administered sub-cutaneously three times a week (TIW) at a dosage of 22 to 44 µg or 6 MIU to 12 MIU per person.

Patients

Preferably, patients according to the invention are patients suffering from Primary Progressive Multiple Sclerosis (PPMS), Secondary Progressive Multiple Sclerosis (SPMS) and Early Secondary Progressive Multiple Sclerosis (ESPMS), preferably Primary Progressive Multiple Sclerosis (PPMS) and Secondary Progressive Multiple Sclerosis (SPMS).

Especially preferably, patients according to the invention are patients diagnosed Primary Progressive Multiple Sclerosis (PPMS), Secondary Progressive Multiple Sclerosis (SPMS) and Early Secondary Progressive Multiple Sclerosis (ESPMS), preferably Primary Progressive Multiple Sclerosis (PPMS) and Secondary Progressive Multiple Sclerosis (SPMS). The criteria for the diagnosis are known to the one skilled in the art, and furthermore described at various sections herein.

Thus, preferably patients according to the invention do not suffer from RRMS and/or or ESPMS, or are not diagnosed RRMS and/or ESPMS. More preferably, patients to be treated according to the invention are diagnosed a form of MS that is different from RRMS and/or ESPMS, or are diagnosed to suffer from a form of MS that is different from relapsing forms of MS.

Preferably, according to this invention, patients are selected from human males or females between 10 and 70 of age, more preferably between 18 and 65 years of age, even more preferably 18 and 55 years of age, and especially 18 and 51 years of age. Since female patients are in the vast majority and often have a higher disease burden, the treatment of female patients is preferred.

Alternative Uses and/or Methods of Treatment According to the Invention

In one embodiment, the invention provides a use of Cladribine for the preparation of a pharmaceutical formulation for the treatment of progressive forms of Multiple Sclerosis, preferably PPMS and/or SPMS, wherein the formulation is to be orally administered following the sequential steps below:
  (i) An induction period wherein Cladribine pharmaceutical formulation is administered and wherein the total dose of Cladribine reached at the end of the induction period is from about 1.7 mg/kg to about 3.5 mg/kg;
  (ii) A Cladribine-free period wherein no Cladribine is administered;
  (iii) A maintenance period wherein Cladribine pharmaceutical formulation is administered and wherein the total dose of Cladribine reached at the end of the maintenance period is lower than or an equal to the total dose of Cladribine reached at the end of the induction period (i);
  (iv) A Cladribine-free period wherein no Cladribine is administered.

In a further embodiment, the invention provides a use according to the invention wherein the induction period lasts up to about 4 months or up to about 3 months or up to about 2 months.

In a further embodiment, the invention provides a use according to the invention wherein the induction period lasts up to about 2 months.

In a further embodiment, the invention provides a use according to the invention wherein the induction period lasts up to about 4 months.

In a further embodiment, the invention provides a use according to the invention wherein the Cladribine free period (ii) lasts about 10 months, about 12 months, about 14 months or about 16 months.

In a further embodiment, the invention provides a use according to the invention wherein the Cladribine free period (iv) lasts about 10 months, about 14 months, about 22 months or about 32 months.

In a further embodiment, the invention provides a use according to the invention wherein the total dose of Cladribine reached at the end of the induction period is about 1.75 mg/kg.

In a further embodiment, the invention provides a use according to the invention wherein the total dose of Cladribine reached at the end of the induction period is about 3.5 mg/kg.

In a further embodiment, the invention provides a use according to the invention wherein the total dose of Cladribine reached at the end of the maintenance period is about 1.75 mg/kg.

In a further embodiment, the invention provides a use according to the invention wherein the total dose of Cladribine reached at the end of the maintenance period is about 3.5 mg/kg, more preferably about 1.75 mg/kg.

In another further embodiment, the invention provides a use according to the invention wherein the Cladribine-free period lasts up to about 34 months, or up to 20 months, or up to 10 months. This is especially preferred regarding the Cladribine free period (iv).

In another further embodiment, the invention provides a use according to the invention wherein the Cladribine-free (ii) period lasts up to about 8 months.

In another further embodiment, the invention provides a use according to the invention wherein the Cladribine-free (ii) period lasts at least about 8 months.

In another further embodiment, the invention provides a use according to the invention wherein the Cladribine-free period (ii) lasts at least about 10 months, typically 10 to 18 months, and especially about 10 months.

In another further embodiment, the invention provides a use according to the invention wherein the Cladribine-free (iv) period lasts at least about 10 months.

In another further embodiment, the invention provides a use according to the invention wherein the Cladribine-free (iv) period lasts at least about 8 months, more preferably at least about 10 months, even more preferably at least 18 months and especially at least 24 months.

In another further embodiment, the invention provides a use according to the invention wherein the Cladribine-free periods (ii) and/or (iv) last at least about 8, more preferably at least 10 months, and typically either about 10 months or about 10 to 18 months.

In another further embodiment, the invention provides a use according to the invention wherein a placebo-pill is administered during the Cladribine-free period.

In another further embodiment, the invention provides a use according to the invention wherein the Cladribine-free period is free of any administration.

In another further embodiment, the invention provides a use according to the invention wherein the maintenance period lasts up to about 4 months, or up to about 3 months, or up to about 2 months, preferably up to about 2 months.

In another further embodiment, the invention provides a use according to the invention wherein the total dose of Cladribine reached at the end of the maintenance period (iii) is about 1.75 mg/kg.

In another further embodiment, the invention provides a use according to the invention wherein the steps (iii) to (iv) are repeated at least one or two times.

In this regard, the Cladribine-free period (iv) preferably lasts at least about 24 months, or least about 18 months, or at least 12 months, or at least about 10 months, or at least about 9 months, or at least about 8 months.

In a preferred embodiment, the invention provides a use of Cladribine for the preparation of a pharmaceutical formulation for the treatment of progressive forms of Multiple Sclerosis, preferably PPMS and/or SPMS, wherein the formulation is to be orally administered following the sequential steps below:
  (i) An induction period wherein Cladribine pharmaceutical formulation is administered and wherein the total dose of Cladribine reached at the end of the induction period is from about 1.7 mg/kg to about 3.5 mg/kg;
  (ii) A Cladribine-free period wherein no Cladribine is administered;
  (iii) A maintenance period wherein Cladribine pharmaceutical formulation is administered and wherein the total dose of Cladribine reached at the end of the maintenance period is lower than or about equal, preferably about equal, to the total dose of Cladribine reached at the end of the induction period (i)
  (iv) A Cladribine-free period wherein no Cladribine is administered;
wherein the induction period last up to about 4 months, or up to about 3 months, or up to about 2 months; the Cladribine-free period (ii) lasts up to about 10 months, or up to about 9 months, or up to about 8 months; the maintenance period (iii) lasts up to about 2 months; the Cladribine-free period (iv) lasts up to about 10 months; the total dose of Cladribine reached at the end of the maintenance period is about 1.7 mg/kg and steps (iii) to (iv) are repeated performed one, two or three times.

In another embodiment, the invention provides a use of Cladribine for the preparation of a pharmaceutical formulation for the treatment of progressive Forms of Multiple Sclerosis, preferably PPMS and/or SPMS, wherein the formulation is to be orally administered following the sequential steps below:
  (i) An induction period wherein Cladribine pharmaceutical formulation is administered and wherein the total effective dose of Cladribine reached at the end of the induction period is from about 0.7 mg/kg to about 1.4 mg/kg;
  (ii) A Cladribine-free period wherein no Cladribine is administered;
  (iii) A maintenance period wherein Cladribine pharmaceutical formulation is administered and wherein the total effective dose of Cladribine reached at the end of the maintenance period (iii) is lower than or about equal, preferably about equal, to the total effective dose of Cladribine reached at the end of the induction period (i);
  (iv) A Cladribine-free period wherein no Cladribine is administered.

In a further embodiment, the invention provides a use of Cladribine for the preparation of a pharmaceutical formulation for the treatment of progressive forms of Multiple Sclerosis, preferably PPMS and/or SPMS, wherein the formulation is to be orally administered following the sequential steps below:
  (i) An induction period wherein Cladribine pharmaceutical formulation is administered and wherein the total effective dose of Cladribine reached at the end of the induction period is from about 0.7 mg/kg to about 1.4 mg/kg;
(ii) A Cladribine-free period wherein no Cladribine is administered;
(iii) A maintenance period wherein Cladribine pharmaceutical formulation is administered and wherein the total effective dose of Cladribine reached at the end of the maintenance period is lower than or equal, preferably equal, to the total effective dose of Cladribine reached at the end of the induction period (i);
(iv) A Cladribine-free period wherein no Cladribine is administered;
wherein the induction period lasts up to about 4 months, or up to about 3 months, or up to about 2 months; the Cladribine-free period (ii) lasts up to about 10 months, or up to about 9 months, or up to about 8 months; the maintenance period (iii) lasts up to about 2 months; the Cladribine-free period (ii) lasts up to about 10 months; the total effective dose of Cladribine reached at the end of the maintenance period is about 0.7 mg/kg and steps (iii) to (iv) are repeated performed one, two or three times.

In a preferred embodiment, the invention provides Cladribine for use as a medicament for the treatment of progressive forms of Multiple Sclerosis, preferably PPMS and/or SPMS, wherein the medicament is to be orally administered following the sequential steps below:
(i) An induction period wherein Cladribine pharmaceutical formulation is administered and wherein the total dose of Cladribine reached at the end of the induction period is from about 1.7 mg/kg to about 3.5 mg/kg, preferably either about 1.75 mg/kg are about 3.5 mg/kg, more preferably about 1.75 mg/kg;
(ii) A Cladribine-free period wherein no Cladribine is administered;
(iii) A maintenance period wherein Cladribine pharmaceutical formulation is administered and wherein the total dose of Cladribine reached at the end of the maintenance period is lower than or equal to the total dose of Cladribine reached at the end of the induction period (i);
(iv) A Cladribine-free period wherein no Cladribine is administered;
wherein the induction period last up to about 4 months, or up to about 3 months, or up to about 2 months; the Cladribine-free period (ii) lasts up to about 10 months, or up to about 9 months, or up to about 8 months; the maintenance period (iii) lasts up to about 2 months; the Cladribine-free period (iv) lasts up to about 10 months; the total dose of Cladribine reached at the end of the maintenance period is about 1.75 mg/kg and steps (iii) to (iv) are repeated performed one, two or three times.

In another embodiment, the invention provides a use of Cladribine according to the invention wherein the pharmaceutical formulation is to be orally administered at a daily dose of Cladribine about 3 to 30 mg Cladribine, preferably 5 to 20 mg Cladribine, most preferably 10 mg Cladribine.

In another further embodiment, the invention provides a use according to the invention wherein the total dose of Cladribine reached at the end of the induction period is about 3.5 mg/kg and the total dose of Cladribine reached at the end of the maintenance period is about 1.75 mg/kg.

In a further embodiment, the invention provides a use according to the invention wherein the total dose of Cladribine reached at the end of the induction period is about 1.75 mg/kg, and the total dose of Cladribine reached at the end of the maintenance period is about 1.75 mg/kg In another further embodiment, the invention provides a use according to the invention wherein the total effective dose of Cladribine reached at the end of the induction period is about 1.4 mg/kg and the total effective dose of Cladribine reached at the end of the maintenance period is about 0.7 mg/kg.

In another embodiment, the invention provides a use of Cladribine according to the invention wherein the pharmaceutical formulation is to be orally administered once a day during the induction period.

In another embodiment, the invention provides a use of Cladribine according to the invention wherein the pharmaceutical formulation is to be orally administered several times a day administered once a day during the induction period, preferably twice or three times a day, more preferably twice a day.

In another embodiment, the invention provides a use of Cladribine according to the invention whereby the pharmaceutical formulation is orally administered about 1 to about 7 days per month, preferably from about 5 to about 7 days per month during the induction period.

In another embodiment, the invention provides a use of Cladribine according to the invention whereby the pharmaceutical formulation is orally administered about 0.02 days/kg to about 0.08 days/kg per month during the induction period.

In another embodiment, the invention provides a use of Cladribine according to the invention whereby the pharmaceutical formulation is orally administered about 0.02 days/kg to about 0.08 days/kg per month during the maintenance period.

In another embodiment, the invention provides a use of Cladribine according to the invention wherein the pharmaceutical formulation is to be orally administered at a daily dose of about 10 mg Cladribine from day 1 to about day 2 each month during the induction period.

In another embodiment, the invention provides a use of Cladribine according to the invention wherein the pharmaceutical formulation is to be orally administered at a daily dose of about 10 mg Cladribine from day 1 to about day 3 each month during the induction period.

In another embodiment, the invention provides a use of Cladribine according to the invention wherein the pharmaceutical formulation is to be orally administered at a daily dose of about 10 mg Cladribine from day 1 to about day 4 each month during the induction period.

In another embodiment, the invention provides a use of Cladribine according to the invention wherein the pharmaceutical formulation is to be orally administered at a daily dose of about 10 mg Cladribine from day 1 to about day 5 each month during the induction period.

In another embodiment, the invention provides a use of Cladribine according to the invention wherein the pharmaceutical formulation is to be orally administered at a daily dose of about 10 mg Cladribine from day 1 to about day 6 each month during the induction period.

In another embodiment, the invention provides a use of Cladribine according to the invention wherein the pharmaceutical formulation is to be orally administered at a daily dose of about 10 mg Cladribine from day 1 to about day 4 each month during the induction period and wherein the pharmaceutical formulation is a pharmaceutical formulation described in WO 2004/087101 or in WO 2004/087100.

In another embodiment, the invention provides a use of Cladribine according to any of the preceding sections wherein the pharmaceutical formulation is to be administered in combination with interferon-beta.

In a preferred embodiment, the invention provides a method for the treatment of progressive forms of Multiple Sclerosis, preferably PPMS and/or SPMS, comprising the oral administration of Cladribine or of a pharmaceutical formulation thereof in a patient in need thereof comprising the following steps:
- (i) An induction period, preferably an induction period of about 2 months, wherein Cladribine or a pharmaceutical formulation thereof is administered and wherein the total dose of Cladribine reached at the end of the induction period is from about 1.5 mg/kg to about 3.5 mg/kg, preferably either about 1.75 mg/kg or about 3.5 mg/kg, more preferably about 1.75 mg/kg;
- (ii) A Cladribine-free period, preferably a Cladribine free period of at least 10 months, wherein no Cladribine is administered;
- (iii) A maintenance period, preferably a maintenance period of about 2 months, wherein Cladribine or a pharmaceutical formulation thereof is administered and wherein the total dose of Cladribine reached at the end of the maintenance period is lower than our equal to the total dose of Cladribine reached at the end of the induction period (i), preferably either about 1.75 mg/kg or about 3.5 mg/kg, more preferably about 1.75 mg/kg;
- (iv) A Cladribine-free period, preferably a Cladribine free period of at least 10 months, wherein no Cladribine is administered.

In a preferred embodiment, the invention provides a method for the treatment of progressive forms of Multiple Sclerosis, preferably PPMS and/or SPMS, comprising the oral administration of Cladribine or of a pharmaceutical formulation thereof in a patient in need thereof comprising the following steps:
- (i) An induction period wherein Cladribine or a pharmaceutical formulation thereof is administered and wherein the total effective dose of Cladribine reached at the end of the induction period is from about 0.7 mg/kg to about 1.4 mg/kg;
- (ii) A Cladribine-free period wherein no Cladribine is administered;
- (iii) A maintenance period wherein Cladribine pharmaceutical formulation is administered and wherein the total effective dose of Cladribine reached at the end of the maintenance period is lower than or equal to the total effective dose of Cladribine reached at the end of the induction period (i);
- (iv) A Cladribine-free period wherein no Cladribine is administered.

In another further embodiment, the invention provides a method according to the invention wherein the steps (iii) to (iv) are repeated at least one or two times.

In this regard, the Cladribine-free period (iv) preferably lasts at least about 24 months, or least about 18 months, or at least 12 months, or at least about 10 months, or at least about 9 months, or at least about 8 months.

In a preferred embodiment, the invention provides a method of treating progressive forms of Multiple Sclerosis, preferably PPMS and/or SPMS, with Cladribine, wherein Cladribine is orally administered following the sequential steps below:
- (i) Administering Cladribine, such that the total dose of Cladribine reached at the end of the induction period is from about 1.7 mg/kg to about 3.5 mg/kg, preferably about 1.75 mg/kg or about 3.5 mg/kg, more preferably 1.75 mg/kg;
- (ii) Administering no Cladribine during a Cladribine free period;
- (iii) Administering Cladribine such that the total dose of Cladribine reached at the end of a maintenance period is lower than or equal to the total dose of Cladribine reached at the end of the induction period (i), preferably about 1.75 mg/kg or about 3.5 mg/kg, more preferably about 1.75 mg/kg);
- (iv) And optionally, a Cladribine-free period wherein no Cladribine is administered.

In a further preferred embodiment, the invention provides a method wherein the induction period lasts up to about 4 months, or up to about 3 months, or up to about 2 months.

In a further preferred embodiment, the invention provides a method wherein the total dose of Cladribine reached at the end of the induction period is about 1.75 mg/kg.

In a further preferred embodiment, the invention provides a method wherein the total dose of Cladribine reached at the end of the induction period is about 3.5 mg/kg.

In a further preferred embodiment, the invention provides a method wherein the total effective dose of Cladribine reached at the end of the induction period is about 1.4 mg/kg.

In a further preferred embodiment, the invention provides a method wherein the Cladribine-free period lasts up to about 18 months, or up to 12 months, or up to 10 months, or up to about 9 months, or up to about 8 months.

In a further preferred embodiment, the invention provides a method wherein the Cladribine-free period (ii) lasts up to about 18 months, or up to 12 months, or up to 10 months, or up to about 9 months, or up to about 8 months.

In a further preferred embodiment, the invention provides a method wherein the maintenance period lasts up to about 4 months, or up to about 3 months or up to about 2 months.

In a further preferred embodiment, the invention provides a method wherein the total dose of Cladribine reached at the end of the maintenance period is about 1.75 mg/kg.

In a further preferred embodiment, the invention provides a method wherein the total effective dose of Cladribine reached at the end of the maintenance period is about 0.7 mg/kg.

In a further preferred embodiment, the invention provides a method wherein the maintenance period is followed by a Cladribine-free period.

In another further embodiment, the invention provides a method according to the invention wherein the total dose of Cladribine reached at the end of the induction period is about 3.5 mg/kg and the total dose of Cladribine reached at the end of the maintenance period is about 1.75 mg/kg.

In another further embodiment, the invention provides a method according to the invention wherein the total effective dose of Cladribine reached at the end of the induction period is about 1.4 mg/kg and the total effective dose of Cladribine reached at the end of the maintenance period is about 0.7 mg/kg.

In another further embodiment, the invention provides a method according to the invention wherein Cladribine is to be orally administered at a daily dose of about 3 to about 30 mg.

In another further embodiment, the invention provides a method according to the invention wherein Cladribine is to be orally administered at a daily dose of about 10 mg.

In another further embodiment, the invention provides a method according to the invention wherein Cladribine is orally administered about 1 to about 7 days per month during the induction period.

In another further embodiment, the invention provides a method according to the invention wherein the steps (iii) are repeated at least one or two times.

In another further embodiment, the invention provides a method according to the invention wherein Cladribine is to be administered in combination with interferon-beta.

Further especially preferred aspects of Cladribine for use as described herein, preferably Cladribine tablets for use as described herein, its properties and/or its use are described below.

Preferred Medicinal Product

Cladribine 10 mg tablets (Mavenclad®)

Qualitative and Quantitative Composition: Each tablet contains 10 mg of Cladribine, Excipients with known effect: Each tablet contains 64 mg sorbitol.

Preferred Pharmaceutical Form: Tablet; white, round, biconvex tablets of 8.5 mm diameter Preferred Clinical Particulars:

Posology and Method of Administration

Posology

In preferred embodiments, a recommended cumulative dose of Cladribine tablets is 3.5 mg/kg body weight over 2 years, administered as 1 treatment course of 1.75 mg/kg per year. Following completion of 2 treatment courses, further Cladribine treatment in Year 3 and/or Year 4 may not be necessary, but may be considered as an option in PPMS and/or SPMS. In these embodiments, each treatment course consists of 2 treatment weeks, one at the beginning of the first month and one at the beginning of the second month of the respective treatment year. Each treatment week consists of 4 or 5 days on which a patient receives 10 mg or 20 mg (one or two tablets) as a single daily dose, depending on body weight. For details, see Tables 1 and 2 below.

The gradual recovery of the lymphocyte counts occurs without the triggering of a homeostatic expansion of residual lymphocyte subtypes potentially associated with rebound activity or autoimmunity seen with some other disease modifying drugs (DMDs) used in MS (Jones, 2013; Zwang, 2014; Willis, 2015). This pharmacokinetic (PK)/PD profile results in a unique posology for an oral drug in the field of MS, with short courses of treatment administered at the beginning of Year 1 and Year 2 (a total of up to 20 days of treatment).

Criteria for Initiating and Continuing Therapy

Lymphocyte counts are recommended to be:

normal before initiating MAVENCLAD in year 1, at least 800 cells/mm$^3$ before initiating MAVENCLAD in year 2.

If necessary, the treatment course in year 2 can be delayed, preferably for up to 6 months, to allow for recovery of lymphocytes.

Distribution of Dose

In certain embodiments, the preferred distribution of the total dose over the 2 years of treatment is provided in Table 1 below. For some weight ranges the number of tablets may vary from one treatment week to the next.

TABLE 1

Dose of MAVENCLAD per treatment week by patient weight in each treatment year

| Weight range | Dose in mg (number of 10 mg tablets) per treatment week | |
|---|---|---|
| kg | Treatment week 1 | Treatment week 2 |
| 40 to <50 | 40 mg (4 tablets) | 40 mg (4 tablets) |
| 50 to <60 | 50 mg (5 tablets) | 50 mg (5 tablets) |
| 60 to <70 | 60 mg (6 tablets) | 60 mg (6 tablets) |

TABLE 1-continued

Dose of MAVENCLAD per treatment week by patient weight in each treatment year

| Weight range | Dose in mg (number of 10 mg tablets) per treatment week | |
|---|---|---|
| kg | Treatment week 1 | Treatment week 2 |
| 70 to <80 | 70 mg (7 tablets) | 70 mg (7 tablets) |
| 80 to <90 | 80 mg (8 tablets) | 70 mg (7 tablets) |
| 90 to <100 | 90 mg (9 tablets) | 80 mg (8 tablets) |
| 100 to <110 | 100 mg (10 tablets) | 90 mg (9 tablets) |
| 110 and above | 100 mg (10 tablets) | 100 mg (10 tablets) |

Table 2 below shows how the total number of tablets per treatment week is distributed over the individual days. It is recommended that the daily Cladribine doses in each treatment week be taken at intervals of 24 hours at approximately the same time each day. If a daily dose consists of two tablets, both tablets are taken together as a single dose.

TABLE 2

MAVENCLAD 10 mg tablets per weekday

| Total number of tablets per week | Day 1 | Day 2 | Day 3 | Day 4 | Day 5 |
|---|---|---|---|---|---|
| 4 | 1 | 1 | 1 | 1 | 0 |
| 5 | 1 | 1 | 1 | 1 | 1 |
| 6 | 2 | 1 | 1 | 1 | 1 |
| 7 | 2 | 2 | 1 | 1 | 1 |
| 8 | 2 | 2 | 2 | 1 | 1 |
| 9 | 2 | 2 | 2 | 2 | 1 |
| 10 | 2 | 2 | 2 | 2 | 2 |

In certain preferred embodiments, a missed dose must be taken as soon as remembered on the same day according to the treatment schedule.

In certain preferred embodiments, a missed dose must not be taken together with the next scheduled dose on the following day. In the case of a missed dose, the patient must take the missed dose on the following day, and extend the number of days in that treatment week. If two consecutive doses are missed, the same rule applies, and the number of days in the treatment week is extended by two days.

Method of Administration

MAVENCLAD is for oral use. In this embodiment, tablets must be taken with water, and swallowed without chewing. The tablets can be taken independent of food intake.

Hematological Monitoring

Cladribine's mode of action is closely linked to a reduction in lymphocyte count. The effect on lymphocyte count is dose-dependent. Decreases in neutrophil count, red blood cell count, hematocrit, hemoglobin or platelet count compared to baseline values have also been observed in clinical studies, although these parameters usually remain within normal limits. Additive hematological adverse reactions may be expected if Cladribine is administered prior to or concomitantly with other substances that affect the hematological profile (see section 4.5).

In certain embodiments, lymphocyte counts must be determined before initiating MAVENCLAD in year 1, before initiating MAVENCLAD in year 2, 2 and 6 months after start of treatment in each treatment year. If the lymphocyte count is below 500 cells/mm$^3$, it should be actively monitored until values increase again.

Mechanism of Action

Cladribine is a nucleoside analogue of deoxyadenosine. A chlorine substitution in the purine ring protects Cladribine from degradation by adenosine deaminase, increasing the intracellular residence time of the Cladribine prodrug. Subsequent phosphorylation of Cladribine to its active triphosphate form, 2-chlorodeoxyadenosine triphosphate (Cd-ATP), is particularly efficiently achieved in lymphocytes, due to their constitutively high deoxycytidine kinase (DCK) and relatively low 5'-nucleotidase (5'-NTase) levels. A high DCK to 5'-NTase ratio favors the accumulation of Cd-ATP, making lymphocytes particularly susceptible to cell death. As a result of a lower DCK/5'-NTase ratio other bone marrow derived cells are less affected than lymphocytes. DCK is the rate limiting enzyme for conversion of the Cladribine prodrug into its active triphosphate form, leading to selective depletion of dividing and non-dividing T and B cells.

The primary apoptosis-inducing mechanism of action of Cd-ATP has direct and indirect actions on DNA synthesis and mitochondrial function. In dividing cells, Cd-ATP interferes with DNA synthesis via inhibition of ribonucleotide reductase and competes with deoxyadenosine triphosphate for incorporation into DNA by DNA polymerases. In resting cells Cladribine causes DNA single-strand breaks, rapid nicotinamide adenine dinucleotide consumption, ATP depletion and cell death. There is evidence that Cladribine can also cause direct caspase-dependent and -independent apoptosis via the release of cytochrome c and apoptosis-inducing factor into the cytosol of non-dividing cells.

Pharmacodynamic Effects

Cladribine has been shown to exert long-lasting effects by preferentially targeting lymphocytes and the autoimmune processes involved in the pathophysiology of MS.

Across studies, the largest proportion of patients with grade 3 or 4 lymphopenia (<500 to 200 cells/mm$^3$ or <200 cells/mm$^3$) was seen 2 months after the first Cladribine dose in each year, indicating a time gap between Cladribine plasma concentrations and the maximum hematological effect.

Across clinical studies, data with the proposed cumulative dose of 3.5 mg/kg body weight show a gradual improvement in the median lymphocyte counts back to the normal range at week 84 from the first dose of Cladribine (approximately 30 weeks after the last dose of Cladribine). The lymphocyte counts of more than 75% of patients returned to the normal range by week 144 from the first dose of Cladribine (approximately 90 weeks after the last dose of Cladribine).

Treatment with oral Cladribine leads to rapid reductions in circulating CD4+ and CD8+ T cells. CD8+ T cells have a less pronounced decrease and a faster recovery than CD4+ T cells, resulting in a temporarily decreased CD4 to CD8 ratio. Cladribine reduces CD19+ B cells and CD16+/CD56+ natural killer cells, which also recover faster than CD4+ T cells.

Clinical Efficacy and Safety

Relapsing-Remitting MS

Efficacy and safety of oral Cladribine were evaluated in a randomized, double-blind, placebo-controlled clinical study (CLARITY) in 1,326 patients with relapsing-remitting MS. Study objectives were to evaluate the efficacy of Cladribine versus placebo in reducing the annualized relapse rate (ARR) (primary endpoint), slowing disability progression and decreasing active lesions as measured by MRI.

Patients received either placebo (n=437), or a cumulative dose of Cladribine of 3.5 mg/kg (n=433) or 5.25 mg/kg body weight (n=456) over the 96-week (2-year) study period in 2 treatment courses. Patients randomized to the 3.5 mg/kg cumulative dose received a first treatment course at weeks 1 and 5 of the first year and a second treatment course at weeks 1 and 5 of the second year. Patients randomized to the 5.25 mg/kg cumulative dose received additional treatment at weeks 9 and 13 of the first year. The majority of patients in the placebo (87.0%) and the Cladribine 3.5 mg/kg (91.9%) and 5.25 mg/kg (89.0%) treatment groups completed the full 96 weeks of the study.

Patients were required to have at least 1 relapse in the previous 12 months. In the overall study population, the median age was 39 years (range 18 to 65), and the female to male ratio was approximately 2:1. The mean duration of MS prior to study enrolment was 8.7 years, and the median baseline neurological disability based on Kurtzke Expanded Disability Status Scale (EDSS) score across all treatment groups was 3.0 (range 0 to 6.0). Over two thirds of the study patients were treatment-naive for MS disease-modifying drugs (DMDs). The remaining patients were pre-treated with either interferon beta-1a, interferon beta-1b, glatiramer acetate or natalizumab.

Patients with relapsing-remitting MS receiving Cladribine 3.5 mg/kg showed statistically significantly improvements in the annualized relapse rate, proportion of patients relapse-free over 96 weeks, proportion of patients free of sustained disability over 96 weeks and time to 3-month EDSS progression compared to patients on placebo (see Table 3 below).

TABLE 3

Clinical outcomes in the CLARITY study (96 weeks)

|  | | Cladribine cumulative dose | |
| --- | --- | --- | --- |
| Parameter | Placebo (n = 437) | 3.5 mg/kg (n = 433) | 5.25 mg/kg (n = 456) |
| Annualised relapse rate (95% CI) | 0.33 (0.29, 0.38) | 0.14* (0.12, 0.17) | 0.15* (0.12, 0.17) |
| Relative reduction (cladribine vs. placebo) |  | 57.6% | 54.5% |
| Proportion of patients relapse-free over 96 weeks | 60.9% | 79.7% | 78.9% |
| Time to 3-month EDSS progression, 10$^{th}$ percentile (months) | 10.8 | 13.6 | 13.6 |
| Hazard ratio (95% CI) |  | 0.67* (0.48, 0.93) | 0.69* (0.49, 0.96) |

*p < 0.001 compared to placebo

In addition, the Cladribine 3.5 mg/kg treatment group was statistically significantly superior to placebo with regard to number and relative reduction of T1 Gd+ lesions, active T2 lesions and combined unique lesions as demonstrated in brain MRI over the entire 96 weeks of the study. Patients taking Cladribine compared to the placebo treatment group had 86% relative reduction in the mean number of T1 Gd+ lesions (adjusted mean number for Cladribine 3.5 mg/kg, and placebo groups were 0.12 and 0.91, respectively), 73% relative reduction in the mean number of active T2 lesions (adjusted mean number for Cladribine 3.5 mg/kg, and placebo groups were 0.38 and 1.43, respectively) and 74% relative reduction in the mean number of combined unique lesions per patient per scan (adjusted mean number for Cladribine 3.5 mg/kg, and placebo groups were 0.43 and 1.72, respectively) ($p<0.001$ across all 3 MRI outcomes).

Post-hoc analysis of time to 6-month confirmed EDSS progression resulted in a 47% reduction of the risk of disability progression in the Cladribine 3.5 mg/kg compared to placebo (hazard ratio=0.53, 95% CI [0.36, 0.79], $p<0.05$); in the placebo group the 10th percentile was reached at 245 days, and not reached at all during the study period in the Cladribine 3.5 mg/kg group.

As shown in Table 3 above, higher cumulative doses did not add any clinically meaningful benefit, but were associated with a higher incidence in ≥grade 3 lymphopenia (44.9% in the 5.25 mg/kg group vs. 25.6% in the 3.5 mg/kg group).

Patients who had completed the CLARITY study could be enrolled in CLARITY Extension. In this extension study, 806 patients received either placebo or a cumulative dose of Cladribine 3.5 mg/kg (in a regimen similar to that used in CLARITY) over the 96-week study period. The primary objective of this study was safety, while efficacy endpoints were exploratory.

The magnitude of the effect in reducing the frequency of relapses and slowing disability progression in patients receiving the 3.5 mg/kg dose over 2 years was maintained in years 3 and 4 (see section 4.2).

Efficacy in Patients with High Disease Activity

Post-hoc subgroup efficacy analyses have been conducted in patients with high disease activity treated with oral Cladribine at the recommended 3.5 mg/kg cumulative dose. These included
patients with 1 relapse in the previous year and at least 1 T1 Gd+ lesion or 9 or more T2 lesions, while on therapy with other DMDs,
patients with 2 or more relapses in the previous year, whether on DMD treatment or not.

In the analyses of the CLARITY data, a consistent treatment effect on relapses was observed with the annualized relapse rate ranging from 0.16 to 0.18 in the Cladribine groups and 0.47 to 0.50 in the placebo group ($p<0.0001$). Compared to the overall population, a greater effect was observed in time to 6-month sustained disability where Cladribine reduced the risk of disability progression by 82% (hazard ratio=0.18, 95% CI [0.07, 0.47]). For placebo the 10th percentile for disability progression was reached between 16 and 23 weeks, while for the Cladribine groups it was not reached during the entire study.

Secondary Progressive MS with Relapses

A supportive study in patients treated with Cladribine as an add-on to interferon-beta vs. placebo+interferon-beta also included a limited number of patients with secondary progressive MS (26 patients). In these patients, treatment with Cladribine 3.5 mg/kg resulted in a reduction of the annualized relapse rate compared to placebo (0.03 versus 0.30, risk ratio: 0.11, $p<0.05$). There was no difference in annualized relapse rate between patients with relapsing-remitting MS and patients with secondary progressive MS with relapses. An effect on disability progression could not be shown in either subgroup.

Patients with secondary progressive MS were excluded in the CLARITY study. However, a post-hoc analysis of a mixed cohort including CLARITY and ONWARD patients, defined by a baseline EDSS score of ≥3.5 as a proxy for secondary progressive MS, showed a similar reduction in annualized relapse rate compared to patients with an EDSS score below 3.

Pharmacokinetic Properties

Cladribine is a prodrug that has to be phosphorylated intracellularly to become biologically active. Cladribine pharmacokinetics were studied following oral and intravenous administration in MS patients and patients with malignancies, and in in vitro systems.

Absorption

Following oral administration, Cladribine is rapidly absorbed. Administration of 10 mg Cladribine resulted in a Cladribine mean Cmax in the range of 22 to 29 ng/mL and corresponding mean AUC in the range of 80 to 101 ng·h/mL (arithmetic means from various studies).

When oral Cladribine was given in fasted state, median Tmax was 0.5 h (range 0.5 to 1.5 h). When administered with a high-fat meal, Cladribine absorption was delayed (median Tmax 1.5 h, range 1 to 3 h) and Cmax was reduced by 29% (based on geometric mean), while AUC was unchanged. The bioavailability of 10 mg oral Cladribine was approximately 40%.

Distribution

The volume of distribution is large, indicating extensive tissue distribution and intracellular uptake. Studies revealed a mean volume of distribution of Cladribine in the range of 480 to 490 L. The plasma protein binding of Cladribine is 20%, and independent of plasma concentration.

The distribution of Cladribine across biological membranes is facilitated by various transport proteins, including ENT1, CNT3 and BCRP.

In vitro studies indicate that Cladribine efflux is only minimally P-gp related. Clinically relevant interactions with inhibitors of P-gp are not expected. The potential consequences of P-gp induction on the bioavailability of Cladribine have not been formally studied.

In vitro studies showed negligible transporter-mediated uptake of Cladribine into human hepatocytes.

Cladribine is almost equally distributed between plasma and whole blood cells and has the potential to penetrate the blood brain barrier by 25% (Liliemark, 1992; Kearns, 1994). A small study in cancer patients has shown a cerebrospinal fluid/plasma concentration ratio of approximately 0.25.

Cladribine and/or its phosphorylated metabolites are substantially accumulated and retained in human lymphocytes. In vitro, intra-versus extracellular accumulation ratios were found to be around 30 to 40 already 1 hour after Cladribine exposure.

Biotransformation

The metabolism of Cladribine was studied in MS patients following the administration of a single 10-mg tablet and a single 3-mg intravenous dose. Following both oral and intravenous administration, the parent compound Cladribine was the main component present in plasma and urine. The metabolite 2-chloroadenine was a minor metabolite both in plasma and in urine, e.g. accounting only for ≤3% of plasma parent drug exposure after oral administration. Only traces of other metabolites could be found in plasma and in urine.

In hepatic in vitro systems, negligible metabolism of Cladribine was observed (at least 90% was unchanged Cladribine).

Cladribine is not a relevant substrate to cytochrome P450 enzymes and does not show significant potential to act as inhibitor of CYP1A2, CYP2B6, CYP2C8, CYP2C9, CYP2C19, CYP2D6, CYP2E1 and CYP3A4. Inhibition of these enzymes or genetic polymorphisms (e.g. CYP2D6, CYP2C9 or CYP2C19) are not expected to result in clinically significant effects on Cladribine pharmacokinetics or exposure. Cladribine has no clinically meaningful inductive effect on CYP1A2, CYP2B6 and CYP3A4 enzymes.

After entering the target cells, Cladribine is phosphorylated to Cladribine monophosphate (Cd-AMP) by DCK (and also by deoxyguanosine kinase in the mitochondria). Cd-AMP is further phosphorylated to Cladribine diphosphate (Cd-ADP) and Cladribine triphosphate (Cd-ATP). The dephosphorylation and deactivation of Cd-AMP is catalyzed by cytoplasmic 5'-NTase. In a study of the intracellular pharmacokinetics of Cd-AMP and Cd-ATP in patients with chronic myelogenous leukemia, the levels of Cd-ATP were approximately half of the Cd-AMP levels.

Intracellular half-life of Cd-AMP was 15 h. Intracellular half-life of Cd-ATP was 10 h.

Elimination

Based on pooled population pharmacokinetic data from various studies, the median values for elimination were 22.2 L/h for renal clearance and 23.4 L/h for non-renal clearance. Renal clearance exceeded the glomerular filtration rate, indicating active renal tubular secretion of Cladribine.

The non-renal part of the elimination of Cladribine (approximately 50%) consists of negligible hepatic metabolism and of extensive intracellular distribution and trapping of the active Cladribine principle (Cd-ATP) within the targeted intracellular compartment (i.e. the lymphocytes) and subsequent elimination of intracellular Cd-ATP according to the life-cycle and elimination pathways of these cells. The intracellular metabolism of Cladribine plays an important role in the overall efficacy and safety of Cladribine, and is probably the most important non-renal elimination pathway of Cladribine.

The estimated terminal half-life for a typical patient from the population pharmacokinetic analysis is approximately 1 day. This however does not result in any drug accumulation after once daily dosing as this half-life only accounts for a small portion of the AUC.

Dose and Time Dependence

After oral administration of Cladribine across a dose range from 3 to 20 mg, Cmax and AUC increased in a dose-proportional fashion, suggesting that absorption is not affected by rate- or capacity-limited processes up to a 20 mg oral dose.

No significant accumulation of Cladribine concentration in plasma has been observed after repeated dosing. There is no indication that Cladribine pharmacokinetics might change in a time-dependent fashion after repeated administration.

Special Populations

No studies have been conducted to evaluate the pharmacokinetics of Cladribine in elderly or in pediatric MS patients, or in subjects with renal or hepatic impairment.

A population kinetic analysis did not show any effect of age (range 18 to 65 years) or gender on Cladribine pharmacokinetics.

Renal Impairment

Renal clearance of Cladribine was shown to be dependent on creatinine clearance. Based on a population pharmacokinetic analysis including patients with normal renal function and with mild renal impairment, total clearance in patients with mild renal impairment (CLCR=60 mL/min) is expected to decrease moderately, leading to an increase in exposure of 25%.

Hepatic Impairment

The role of hepatic function for the elimination of Cladribine is considered negligible.

Pharmacokinetic Interactions

A drug interaction study in MS patients showed that the bioavailability of 10 mg oral Cladribine was not altered when co-administered with pantoprazole.

Preclinical Safety Data

Non-clinical safety pharmacological and toxicological assessment of Cladribine in animal models relevant for the safety assessment of Cladribine did not yield significant findings other than those predicted by the pharmacologic mechanism of Cladribine. The primary target organs identified in the repeat-dose toxicology studies by parenteral routes (intravenous or subcutaneous) up to 1-year duration in mice and monkeys were the lymphoid and hematopoietic system. Other target organs after longer administration (14 cycles) of Cladribine to monkeys by subcutaneous route were the kidneys (karyomegaly of renal tubular epithelium), adrenals (cortex atrophy and decreased vacuolation), gastrointestinal tract (mucosa atrophy) and testes. Effects on the kidneys were also seen in mice.

Mutagenicity

Cladribine is incorporated into DNA strands and inhibits DNA synthesis and repair. Cladribine did not induce gene mutation in bacteria or mammalian cells, but it was clastogenic causing chromosomal damage in mammalian cells in vitro at a concentration which was 17-fold above the expected clinical Cmax. In vivo clastogenicity in mice was detected at 10 mg/kg, which was the lowest dose tested.

Carcinogenicity

The carcinogenic potential of Cladribine was assessed in a long-term 22-month study with subcutaneous administration in mice and in a short-term 26-week study by oral route in transgenic mice.

In the long-term carcinogenicity study in mice, the highest dose used was 10 mg/kg, which was seen to be genotoxic in the mouse micronucleus study (equivalent to approximately 16-fold the expected human exposure in AUC in patients taking the maximum daily dose of 20 mg Cladribine). No increased incidence of lymphoproliferative disorders or other tumor types (apart from Harderian gland tumors, predominantly 1n adenomas) was seen in mice. Harderian gland tumors are not considered to be of clinical relevance, as humans do not have comparable anatomical structures.

In the short-term carcinogenicity study in Tg rasH2 mice, no Cladribine-related increase in incidence of lymphoproliferative disorders or other tumor types was seen at any dose tested up to 30 mg/kg per day (equivalent to approximately 25-fold the expected human exposure in AUC in patients taking the maximum daily dose of 20 mg Cladribine).

Cladribine was also assessed in a 1-year monkey study by the subcutaneous route. No increased incidence in lymphoproliferative disorders and no tumors were seen in this study.

Although Cladribine may have a potential for genotoxicity, long-term data in mice and monkeys did not provide any evidence of a relevant increased carcinogenicity risk in humans.

Reproduction Toxicity

While there were no effects on female fertility, reproductive function or general performance of offspring, Cladribine was shown to be embryo lethal when administered to pregnant mice, and the compound was teratogenic in mice (also following treatment of the males only) and rabbits. The observed embryo lethal and teratogenic effects are consistent with the pharmacologic mechanisms of Cladribine. In a male mouse fertility study, malformed fetuses with agenesis of portions of appendage(s) distal the humerus and/or femur were seen. The incidence of affected mouse fetuses in this study was in the same range of spontaneous incidence of amelia and phocomelia in this strain of mice. However, considering Cladribine genotoxicity, male-mediated effects related to potential genetic alteration of differentiating sperm cells cannot be excluded.

Cladribine did not affect the fertility of male mice, but observed testicular effects were reduced testicular weights and increased numbers of non-motile sperm. Testicular degeneration and reversible decrease in spermatozoa with rapid progressive motility were also seen in the monkey. Histologically, testicular degeneration was only seen in one male monkey in a 1-year subcutaneous toxicity study.

Pharmaceutical Particulars:
List of Excipients
Hydroxypropylbetadex (2-hydroxypropyl-β-cyclodextrin)
Sorbitol
Magnesium stearate
How to Take MAVENCLAD This medicine is preferably taken exactly as recommended by the doctor. If in doubt, checking with a doctor or pharmacist it is recommended.

Treatment Courses

Patients will be given MAVENCLAD as two treatment courses over 2 years.

Each treatment course consists of 2 treatment weeks, which are one month apart at the beginning of each treatment year.

A treatment week consists of 4 or 5 days on which a patient receives 1 or 2 tablets daily (see Table 4, below).

Example

If a patient starts treatment in mid-April, the tablets are administered as shown in Table 4, below.

TABLE 4

|  | Year 1 |  | Year 2 |
|---|---|---|---|
| 1st treatment week | 1 or 2 tablets daily for 4 or 5 days, mid April | 1st treatment week | 1 or 2 tablets daily for 4 or 5 days, mid April |
| 2nd treatment week | 1 or 2 tablets daily for 4 or 5 days, mid May | 2nd treatment week | 1 or 2 tablets daily for 4 or 5 days, mid May |

Before the start of a treatment course, the doctor will do a blood test to check that the levels of lymphocytes (a type of white blood cells) are in an acceptable range. If this is not the case, treatment can be delayed.

Once patients have completed the 2 treatment courses over 2 years, the doctor will preferably continue to monitor the health status of the respective patient for another 2 years, in which the respective subject preferably does not need to take the medicine.

Dose

1. Each patient will be prescribed the correct number of tablets for each treatment week, based on patient body weight as shown in Table 5, below.
2. Each patient will receive one or more packs of Cladribine tablets to provide the correct number of tablets.
3. After receipt of the respective supply of medicine by the respective patient, every patient is recommended to check that he or she has received the correct number of tablets.
4. In the left column of Table 5 below, each patient can preferably find the row that fits his or her body weight (in kg), and then the number of tablets that should be in the pack(s) for the treatment week that he or she will be starting should be again checked.
5. If the number of tablets in the respective pack(s) is different from the number shown for the respective patient for the respective weight in the Table 5 below, the doctor should be contacted.
6. It is highlighted that for some weight ranges the number of tablets may vary from one treatment week to the next.

Example

If the respective patient weighs 85 kg and is about to start treatment week 1, he or she will be given 8 tablets.

TABLE 5

| | Number of tablets to take | | | |
|---|---|---|---|---|
| | Year 1 treatment course | | Year 2 treatment course | |
| Your weight | Treatment week 1 | Treatment week 2 | Treatment week 1 | Treatment week 2 |
| less than 40 kg | Your doctor will tell you the number of tablets to take | | | |
| 40 to less than 50 kg | 4 | 4 | 4 | 4 |
| 50 to less than 60 kg | 5 | 5 | 5 | 5 |
| 60 to less than 70 kg | 6 | 6 | 6 | 6 |
| 70 to less than 80 kg | 7 | 7 | 7 | 7 |
| 80 to less than 90 kg | 8 | 7 | 8 | 7 |
| 90 to less than 100 kg | 9 | 8 | 9 | 8 |
| 100 to less than 110 kg | 10 | 9 | 10 | 9 |
| 110 kg and above | 10 | 10 | 10 | 10 |

How to Take the Medicine

The tablet(s) are to be taken at about the same time each day and swallowed without chewing. It is not required to take the tablets at meal times, they can be taken with meals or between meals.

Duration of a Treatment Week

Depending on the total number of tablets prescribed, they have to be taken over 4 or 5 days, in each treatment week.

Table 6, below, shows how many tablets (1 or 2 tablets) have to be taken on each day. If the daily dose is 2 tablets, they preferably are to be taken at the same time.

Example

If 8 tablets have to be taken, take 2 tablets on Day 1, Day 2, Day 3, then 1 tablet on Day 4 and Day 5.

TABLE 6

| Total number of tablets per treatment week | Day 1 | Day 2 | Day 3 | Day 4 | Day 5 |
|---|---|---|---|---|---|
| 4 | 1 | 1 | 1 | 1 | 0 |
| 5 | 1 | 1 | 1 | 1 | 1 |

TABLE 6-continued

| Total number of tablets per treatment week | Day 1 | Day 2 | Day 3 | Day 4 | Day 5 |
|---|---|---|---|---|---|
| 6 | 2 | 1 | 1 | 1 | 1 |
| 7 | 2 | 2 | 1 | 1 | 1 |
| 8 | 2 | 2 | 2 | 1 | 1 |
| 9 | 2 | 2 | 2 | 2 | 1 |
| 10 | 2 | 2 | 2 | 2 | 2 |

Further Information

The following abbreviations preferably refer respectively to the definitions below: kg (kilogram), µg (microgram), mg (milligram), AEs (Adverse effects), CNS (Central nervous system), CSF (Cerebrospinal fluid), EDSS (Expanded Disability Status Scale, SNRS (Scripps Neurologic Rating Scale), IFN (interferon), i.v. (intra-venous), MIU (Million International units), MS (multiple sclerosis), MRI (Magnetic resonance imaging), p.o. (per os), PPMS (Primary progressive multiple sclerosis), PRMS (Progressive relapsing multiple sclerosis), RRMS (Relapsing-remitting multiple sclerosis), SPMS (Secondary progressive multiple sclerosis), s.c. (subcutaneous), TIW (Three times a week), 2-CdA (2-chloro-2'deoxyadenosine or Cladribine), UI (International unit).

The term "about" as used herein with respect to numbers, figures, ranges and/or amounts is preferably meant to mean "circa" and/or "approximately". The meaning of those terms is well known in the art and preferably includes a variance, deviation and/or variability of the respective number, figure, range and/or amount of plus/minus 15% and especially of plus/minus 10%.

In any case, the term "about" as used herein with respect to numbers, figures, ranges and/or amounts is preferably meant to mean "circa" and/or "approximately". The meaning of those terms is well known in the art and preferably includes a variance, deviation and/or variability of the respective number, figure, range and/or amount of at least plus/minus 5%.

The terms "disorder(s)" and "disease(s)" as used herein are well-known and understood in the art. In the context of the present invention they are preferably used as synonyms and thus are preferably interchangeable, if the context they are used herein does not strongly implicate otherwise.

In the medical context, including, but not limited to treatment regimens, dosing schedules and clinical trial designs, for convenience and/or ease of use by patients, medical staff and/or physicians, as well as reliability and/or reproducibility of results etc., the terms "week"/"a week", "month"/"a month" and/or "year"/"a year" can used with slight deviations from the definitions of the Gregorian calendar. For example, in said medical context, a month is often referred to as 28 days, and a year is often referred to 48 weeks.

Thus, in the context of the instant invention, the term "week" or "a week" preferably refers to a period of time of about 5, about 6 or about 7 days, more preferably about 7 days.

In the medical context, the term "month" or "a month" preferably refers to a period of time of about 28, about 29, about 30 or about 31 days, more preferably about 28, about 30 or about 31 days.

In the medical context, the term "year" or "a year" preferably refers to a period of time of about 12 months or to a period of time of about 48, about 50, or about 52 weeks, more preferably 12 months, or about 48 or about 52 weeks.

Especially preferred according to the invention are subjects as described herein, wherein the characteristics of two or more preferred, more preferred and/or especially preferred embodiments, aspects and/or subjects are combined into one embodiment, aspect and/or subject. Preferably, according to this invention, preferred subjects or embodiments can be combined with other preferred subjects or embodiments; more preferred subjects or embodiments can be combined with other less preferred or even more preferred subjects or embodiments; especially preferred subjects or embodiments can be combined with other just preferred or just even more preferred subjects or embodiments, and the like.

The invention is explained in greater detail below by means of examples. The invention preferably can be carried out throughout the range described and is not restricted to the examples given here.

Moreover, the following examples are given in order to assist the skilled artisan to better understand the present invention by way of exemplification. The examples are not intended to limit the scope of protection conferred by the claims. The features, properties and advantages exemplified for the processes, compounds, compositions and/or uses defined in the examples may be assigned to other processes, compounds, compositions and/or uses not specifically described and/or defined in the examples, but falling under the scope of what is defined in the claims.

Thus, the following examples describe the invention in more detail but do not limit the invention and its scope.

EXAMPLES

Example 1: ONWARD Study

Patients aged 18-65 years were eligible to enter the ONWARD study if they fulfilled the following criteria:
a diagnosis of RRMS or SPMS with relapses (2005 McDonald criteria)4
treatment with IFN-β for ≥48 consecutive weeks before screening, with ≥1 MS relapse during that period
clinical stability (other than relapses) during the 28 days before screening
an Expanded Disability Status Scale (EDSS) score of 1.0-5.5
normal hematological parameters within 28 days of baseline (Day 1 of randomization), defined as: platelets, 140-450×103/µL; absolute neutrophil count, 2.03-8.36×103/µL; absolute lymphocyte count, 1.02-3.36×103/µL; white blood cell count, 4.1-12.3×103/µL; haemoglobin, 11.6-16.2 g/dL
Switching from one IFN-β therapy to another was permitted in the 48 weeks before screening if the patient had been on a stable regimen of the current IFN-β≥3 months prior to screening.
Patients were excluded if they had an infectious or immune-compromising disease, had been previously treated with an immunosuppressive or cytotoxic therapy, or if they were pregnant, breastfeeding or refused to use contraception during the study.
In the study, a dose of Cladribine tablets of 3.5 mg/kg, added to existing IFN-β therapy, were applied.
All analyses were post-hoc and not pre-specified, no multiplicity adjustments were done to the resulting p values. All comparisons where the p value was less than 0.05 by statistical testing should be regarded as nominally significant.

In the CLARITY study, Cladribine tablets given in short-duration treatment courses annually for 2 years to patients with relapsing-remitting multiple sclerosis (RRMS) significantly improved clinical and MRI outcomes. In the 2-year CLARITY Extension study, the clinical benefits of the initial 2-years of Cladribine treatment (3.5 mg/kg of bodyweight) given in CLARITY were shown to be durable, in patients re-randomised to receive placebo without further active treatment. The ONWARD study confirmed the safety and tolerability of Cladribine tablets (3.5 mg/kg) administered as an add-on to interferon-β (IFN-β) therapy as a primary endpoint in patients who experienced at least one relapse on IFN-β. The ONWARD study also confirmed efficacy as a secondary objective, and showed similar benefits for Cladribine tablets 3.5 mg/kg added on to IFN-β in patients with relapsing MS (RMS). The ONWARD study recruited patients with RMS, (FIG. 1), with patients being eligible for study entry if they had RRMS or secondary progressive MS (SPMS) with relapses. The inclusion of patients with SPMS in ONWARD provided an opportunity to confirm the efficacy of treatment with Cladribine tablets 3.5 mg/kg vs placebo added on to IFN-β in these patients. The objective was to confirm the effect of Cladribine tablets 3.5 mg/kg in patients with SPMS or RRMS in the ONWARD study.

Clinical Efficacy

Figure 2:
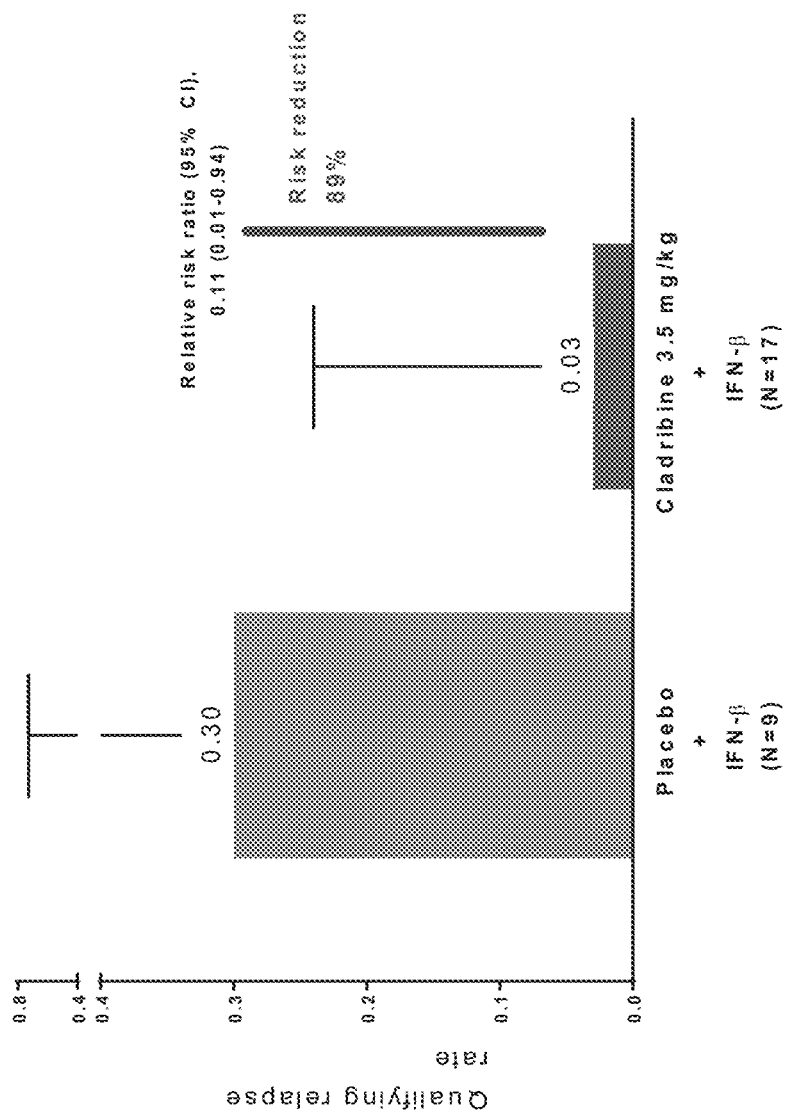
FIG. 2 shows the qualifying relapse rate (annualized, adjusted) in patients with SPMS treated with cladribine tablets 3.5 mg/kg+IFN-β or placebo+IFN-β in ONWARD in Example 1.

In patients with SPMS and in patients with RRMS, patients who received treatment with Cladribine tablets 3.5 mg/kg showed nominally statistically significant reductions in annualized relapse rate compared with placebo. In SPMS patients, the annualized relapse rate was 0.03 (95% CI: 0.00-0.24) for patients treated with Cladribine 3.5 mg/kg+ IFN-β and 0.30 (95% CI 0.13-0.73) for those who received placebo+IFN-β. Cladribine-treated SPMS patients were 89% less likely to have a qualifying relapse than those treated with placebo (FIG. 2).

Figure 3:
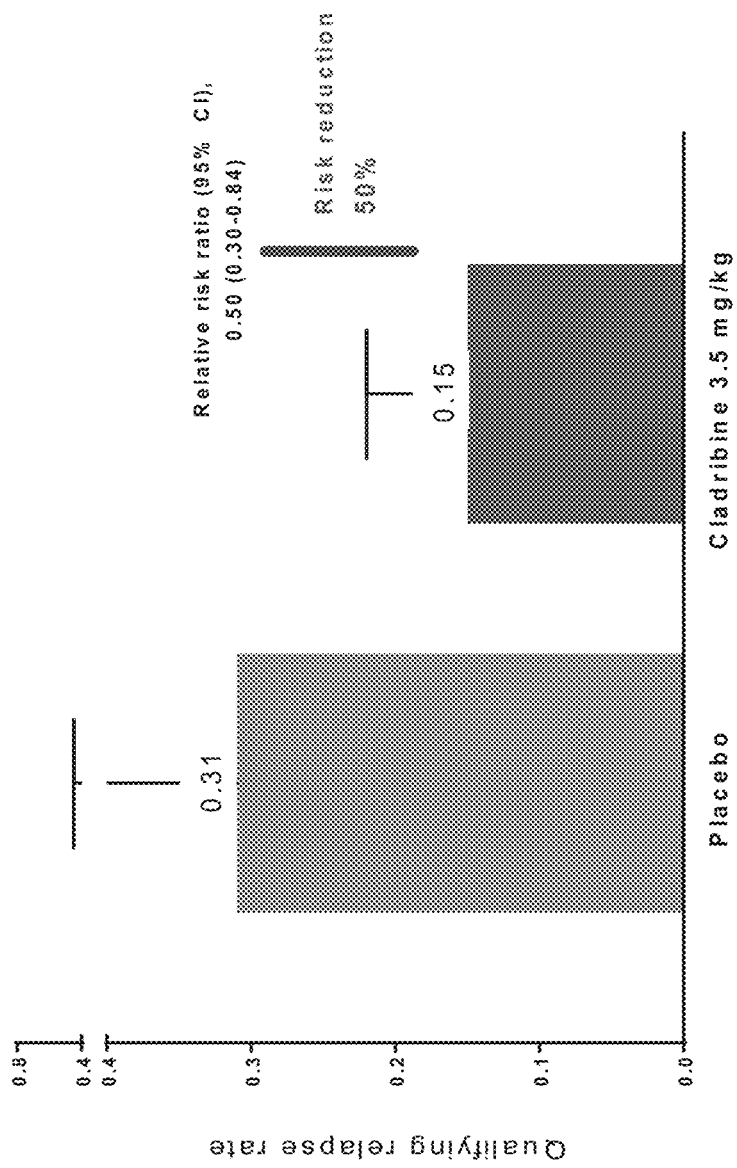
FIG. 3 shows the qualifying relapse rate (annualized, adjusted) in patients with RRMS treated with cladribine tablets 3.5 mg/kg+IFN-0 or placebo+IFN-β in ONWARD in Example 1.
Figure 4:
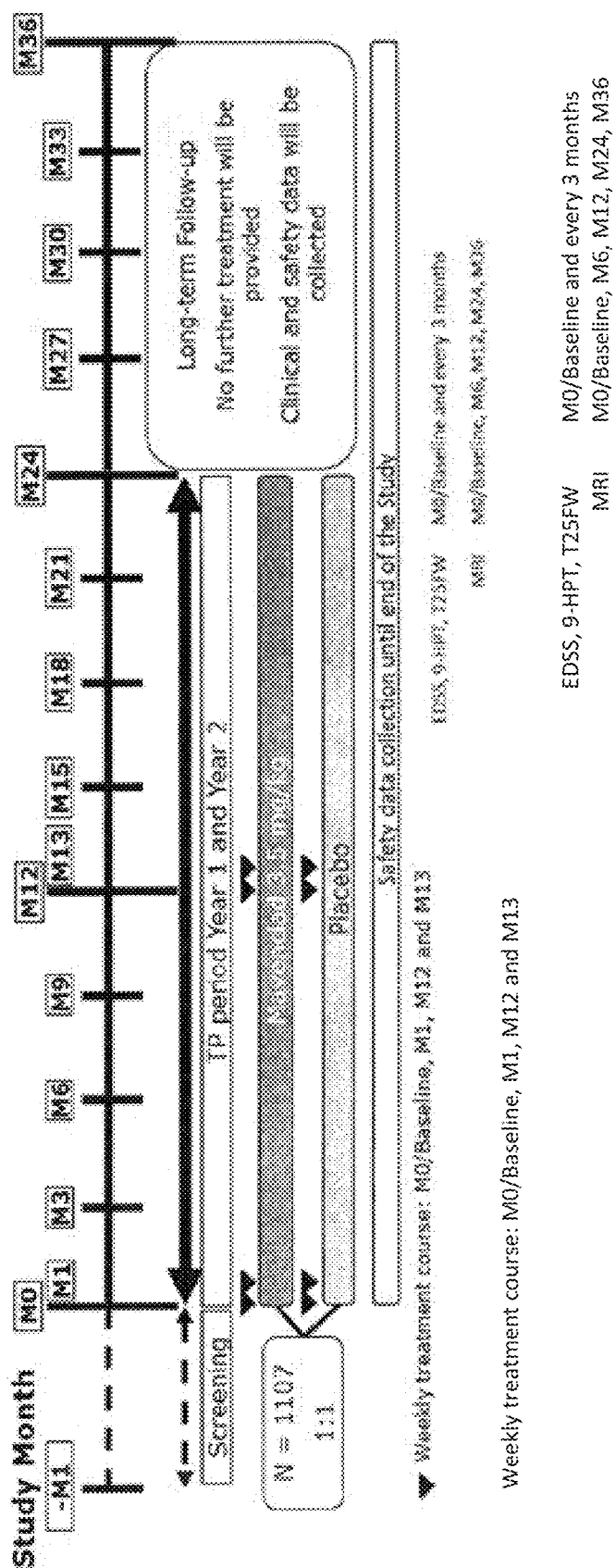
FIG. 4 shows a schematic of the study design for the PPMS Study in Example 2.

In contrast thereto, in RRMS patients, the annualized relapse rate was 0.15 (95% CI: 0.11-0.22) for patients treated with Cladribine 3.5 mg/kg+IFN-β and 0.31 (95% CI 0.21-0.45) for those who received placebo+IFN-β. Thus, Cladribine-treated RRMS patients were only 50% less likely to have a qualifying relapse than those treated with placebo (FIG. 3).

Disability Progression

No treatment effect was observed for the SPMS or RRMS subgroups on either time to 3-month or 6-month confirmed EDSS progression (not shown). These findings are similar to those the overall ONWARD study population and may reflect the low number of patients in the study.

Magnetic Resonance Imaging (MRI) Outcomes

In patients with both SPMS and RRMS, treatment with Cladribine tablets 3.5 mg/kg was associated with reduction

TABLE 7

Patient demographics and disease characteristics for patients classified as SPMS or RRMS (overall ITT population)

| | SPMS patients N = 26[a] | | RRMS patients N = 171[a] | |
|---|---|---|---|---|
| | Placebo + IFN-β N = 9 | Cladribine tablets 3.5 mg/kg + IFN-β N = 17 | Placebo + IFN-β N = 48 | Cladribine tablets 3.5 mg/kg + IFN-β N = 123 |
| Age, years; mean (SD) | 39.9 (10.1) | 41.1 (11.3) | 40.2 (10.0) | 38.1 (10.0) |
| Female, n (%) | 5 (55.6) | 10 (58.8) | 37 (77.1) | 84 (68.3) |
| Disease duration, years; mean (SD) | 8.63 (5.15) | 8.22 (5.85) | 8.18 (6.50) | 6.50 (4.85) |
| Prior use of DMDs. n (%) | 9 (100.0) | 17 (100.0) | 48 (100.0) | 123 (100.0) |
| Relapses in the 12 months prior to study entry, n (%) | | | | |
| 0 | 0 (0.0) | 0 (0.0) | 1 (2.1) | 0 (0.0) |
| 1 | 8 (88.9) | 10 (58.8) | 28 (58.3) | 96 (78.0) |
| 2 | 1 (11.1) | 6 (35.3) | 16 (33.3) | 24 (19.5) |
| ≥3 | 0 (0.0) | 1 (5.9) | 3 (6.3) | 3 (2.4) |
| EDSS score at baseline | | | | |
| Mean (SD) | 4.39 (0.42) | 4.18 (1.33) | 2.80 (1.11) | 2.69 (1.09) |
| Number of T1 Gd+ lesions at baseline | | | | |
| Mean (SD) | 0.1 (0.3) | 1.5 (4.8) | 1.0 (3.1) | 0.9 (3.6) |
| Number of T2 lesions at baseline | | | | |
| Mean (SD) | 37.8 (26.7) | 38.3 (28.8) | 32.5 (19.2) | 32.7 (21.6) |
| T2 lesion volume (cm$^3$) | | | | |
| Mean (SD) | 10.15 (8.60) | 12.46 (14.33) | 13.58 (16.54) | 10.33 (10.73) |

EDSS, Expanded Disability Status Scale;
Gd+, Gadolinium-enhancing;
RRMS, relapsing-remitting multiple sclerosis;
SD, Standard Deviation;
SPMS, secondary progressive multiple sclerosis.
[a]Overall N of placebo and 3.5 mg/kg cladribine groups, excluding 5.25 mg/kg cladribine group in the ITT population (patients randomized under both the original and amended protocols).

in the mean number of T1 Gd+ lesions and in the mean number of active T2 lesions (Table 8, below).

TABLE 8

MRI outcomes for patients classified as SPMS or RRMS

| | SPMS patients N = 26[a] | | RRMS patients N = 171[a] | |
|---|---|---|---|---|
| | Placebo + IFN-β N = 9 | Cladribine tablets 3.5 mg/kg + IFN-β N = 17 | Placebo + IFN-β N = 48 | Cladribine tablets 3.5 mg/kg + IFN-β N = 123 |
| Mean number of new T1 Gd+ lesions per patient per scan | | | | |
| Mean (SD) | 0.67 (2.00) | 0.13 (0.55) | 0.29 (0.64) | 0.05 (0.31) |
| Mean number of T2 lesions per patient per scan | | | | |
| Mean (SD) | 0.59 (1.66) | 0.29 (0.52) | 1.31 (2.36) | 0.58 (1.40) |

Gd+, Gadolinium-enhancing;
RRMS, relapsing-remitting multiple sclerosis;
SD, Standard Deviation;
SPMS, secondary progressive multiple sclerosis.
[a]Overall N of placebo and 3.5 mg/kg cladribine groups, excluding 5.25 mg/kg cladribine group in the ITT population (patients randomised under both the original and amended protocols)

Example 2: PPMS Study

To confirm the efficacy of Cladribine compared with placebo in delaying 6-month confirmed disability progression in subjects with primary progressive multiple sclerosis (PPMS), a second Example is described. This example also describes the efficacy of Cladribine compared with placebo on further measures of disability progression in subjects with PPMS and the efficacy of Cladribine compared with placebo on magnetic resonance imaging (MRI) measures of disease progression in subjects with PPMS.

It also describes the safety and tolerability of treatment with oral Cladribine compared with placebo in subjects with PPMS.

A randomized, double-blind, 2-arm, parallel-group, placebo-controlled, multi-center study, is described for the efficacy and safety of oral Cladribine versus placebo in subjects with PPMS.

This study includes a screening period followed by a 2-year double-blind treatment period with visits occurring at months 0, 1, 3, 6, 9, 11, 12, 13, 15, 18, 21, and 24 followed by a 12-month period of safety follow up.

Subjects are randomized to treatment in a 1:1 ratio. Subjects receiving Cladribine are given up to the recommended cumulative dose of 3.5 mg/kg body weight over 2 years (contingent upon meeting re-treatment criteria: at the time of the second yearly treatment course subjects should have a lymphocyte count of Common Terminology Criteria for Adverse Events [CTCAE] Grade 0 or 1), administered as 1 treatment course of 1.75 mg/kg per year. Subjects receiving matching placebo are given tablets in a similar schedule as the Cladribine-treated subjects.

Assessments of disability, including assessments of Expanded Disability Status Scale, Timed 25-Foot Walk and 9-hole Peg Test, are performed throughout the treatment period. Magnetic resonance imaging will also be performed. Safety is assessed with monitoring of adverse events. In addition, patient-reported outcomes and clinician-reported outcomes are frequently assessed.

Primary Endpoint:
Time to 6-month confirmed disability progression based on EDSS.
Key Secondary Endpoints:
The key secondary endpoints of the study include:
Time to 3-month confirmed disability progression based on a composite score defined by:
A 3-month confirmed EDSS progression and/or;
A 3-month confirmed worsening (>20%) in Timed 25-Foot Walk (T25FW) versus baseline and/or;
A 3-month confirmed worsening (>20%) in 9-Hole Peg Test (9-HPT) versus baseline;
Percent change in total volume of lesions on T2 weighted images from baseline to Month 24;
Percent change in brain volume from Month 6 to Month 24.
Safety Endpoints:
Occurrence of treatment-emergent adverse events (non-serious adverse events [AEs], serious adverse events [SAEs] and adverse events of special interest [AESIs]) in subjects receiving Cladribine compared with placebo;
Evaluation of laboratory parameters (hematology and clinical chemistry) in subjects receiving Cladribine compared with placebo.
Diagnosis and Key Inclusion and Exclusion Criteria:
Inclusion Criteria
Male and female subjects aged 18 to 51 years (inclusive);
Diagnosis of PPMS as per the revised McDonald criteria, preferably the McDonald 2010 criteria (Polman, 2011), and confirmed by PPMS Adjudication Committee (PPMS AC);
EDSS score from 2.5 to 5.5, inclusive; subjects with an EDSS score of 2.0 are eligible if the documented deficit affects either the pyramidal or cerebellar functional systems;
Time from onset of symptoms of PPMS of <15 years for subjects with an EDSS score of 5.5 at screening, or <10 years for subjects with an EDSS score of 5.0 or less at screening.
Medicinal Product: Dose/Mode of Administration/Dosing Schedule:
Cladribine tablets (10 mg) or matching placebo: 3.5 mg/kg body weight to be administered over 2 years (i.e., 1 treatment course of 1.75 mg/kg per year), followed by observation for another 12 months for safety. Each treatment course consists of 2 treatment weeks, 1 week at the beginning of the first month and 1 week at the beginning of the second month of the respective year. Each treatment week consists of 4 or 5 days, in which a subject receives either 10 mg or 20 mg (either 1 or 2 tablets) as a single daily dose, depending on body weight.
Study and Treatment Duration Per Subject:
Subjects will undergo screening assessments followed by a 2-year treatment period. Safety will then be followed for an additional 12 months.
Background Information
The preferred cumulative dose of Cladribine is 3.5 mg/kg body weight over 2 years (as approved for the indication of relapsing-remitting MS (RMS)), preferably administered as 2 treatment courses (i.e., 1.75 mg/kg per year).
Cladribine has shown proven efficacy in relapsing MS (RMS). This clinical study is part of the overall development strategy of oral Cladribine to expand the labeling indication to include not only subjects with relapsing MS, but also PPMS, because of the high unmet medical need in this indication. Although PPMS accounts only for 10% to 15% of MS cases (Miller, 2007), the absence of a widely available proven effective oral treatment underscores the unmet medical need.

The results from the Phase II/III oral Cladribine studies provided clinical efficacy data, both individually and in integrated analyses, showing that oral Cladribine is highly efficacious in subjects with active disease across the clinical spectrum of RMS. The CLARITY study demonstrated robust clinical and MRI efficacy in a population comprising both treatment-naïve and treatment-experienced RRMS. Analysis of CLARITY and CLARITY EXT showed that the efficacy of Cladribine in reducing relapses and slowing EDSS progression is maintained for at least 2 additional years off therapy after 2 short treatment courses with the recommended dose of 3.5 mg/kg. The ORACLE MS study showed consistent clinical and MRI efficacy, with Cladribine reducing the conversion of clinically isolated syndrome (CIS) subjects into clinically definite MS and McDonald 2005 MS. ONWARD was not fully designed for a formal proof of efficacy, but for an evaluation of the safety and efficacy profile of Cladribine as add-on therapy to interferon (IFN)-β; however, the efficacy data do support the findings of the CLARITY study in a RMS patient population. For all of the above studies, the 5.25 mg/kg Cladribine dose (and in the case of some additional studies, 2 higher doses: 7.0 mg/kg and 8.75 mg/kg) did not add any clinically meaningful benefit, compared with the 3.5 mg/kg dose. The significant efficacy of Cladribine on MRI endpoints highlights the anti-inflammatory characteristics of Cladribine.

Selective depletion of lymphocytes, including B-cells, is thought to play an important role in early PPMS. Ocrelizumab, a humanized monoclonal antibody that targets the CD20 surface molecule on B-cells triggering their depletion, has recently been approved by the Food and Drug Administration (FDA) for the treatment of patients with RRMS and early PPMS; approval has been denied in Europe. No other agents are currently available for clinical use in early PPMS.

Several lines of evidence suggest that B-cells and B-cell-derived products could be instrumental in chronic progression of MS (Fereidan-Esfahani, 2015). In RRMS and secondary progressive MS (SPMS), and in the majority of patients with PPMS, clonally-expanded B-cells sequestered within the central nervous system (CNS) compartment produce oligoclonal bands and further clonally expand within the lesions. Recent findings suggest that meningeal B-cell infiltrates, possibly organized in B-cell follicle-like structures, could be the niche maintaining pathogenic CNS B-cell function (Magliozzi, 2007). In progressive forms of MS, meningeal and perivascular B-cell accumulation often co-localizes with activated T-cells and macrophages and experimental evidence suggests that these meningeal immune cell conglomerates are associated with cortical lesion formation, demyelination and microglia activation. Cladribine is a good candidate drug for PPMS due to its high efficacy, demonstrated in subjects with RMS and CIS, and its ability to target selectively B-cells and T-cells, both in the periphery and potentially in the CNS, since Cladribine is found to be blood-brain barrier penetrant and enters the brain independent of vascular leakage. Moreover, previous data with parenteral Cladribine in chronic MS showed trends in MRI efficacy (T1-weighted gadolinium-enhanced [T1 Gd+]) (Rice, 2000; see Section 5.2 for details). Therefore, the Sponsor has designed this clinical study to confirm Cladribine's effects in subjects with PPMS. Data from this study is used to achieve indication expansion for Cladribine to patients with PPMS.

TABLE 9

Large PPMS studies: Comparison of key entry criteria, baseline characteristics, and outcomes

| Study/ Study Drug | n | Entry age EDSS | Actual mean age Mean EDSS | Baseline % T1 Gd+ scans | CSF+ at baseline | Endpoint | % with CDP placebo | % with CDP study drug | EDSS progression overall HR (95% CI) |
|---|---|---|---|---|---|---|---|---|---|
| PROMISE glatiramer acetate | 943 | 30-65 3.0-6.5 | 50.4 4.9 | 14% | 78.4% (not a requirement) | CDP (3) Month 12 Month 24 | 22% 40% | 22% 41% | 0.87 (0.71-1.07) p = 0.1753 |
| OLYMPUS rituximab | 439 | 18-65 2.0-6.5 | 49.9 4.8 | 25% | Required | CDP (3) Week 48 Week 96 CDP (6) Week 96 | 19.3% 38.5% 30.4% | 20.2% 30.2% 27.3% | 0.77 (0.55-1.09) p = 0.14 p = 0.59 |
| INFORMS fingolimod | 654 | 25-65 3.5-6.0 | 48.5 4.67 | 13% | Required | CDP (3) EDSS Composite | 58.7% 80.3% | 54.3% 77.2% | 0.88 (0.80-1.12) p = 0.21 0.95 (0.80-1.12) p = 0.544 |
| ORATORIO ocrelizumab | 725 | 18-55 3.0-6.5 | 44.7 4.7 | ~25% | Required | CDP (3) Month 12 Week 120 CDP (6) Month 12 Week 120 | ~18.9% 39.3% ~21.4% 35.7% | ~13.2% 32.9% ~15.2% 29.7% | 0.76 (0.59-0.98) p = 0.0321 0.75 (0.58-0.98) p = 0.0365 |

CDP = confirm EDSS progression, CSF = cerebrospinal fluid, EDSS = Expanded Disability Status Scale, HR = hazard ratio, PPMS = primary progressive multiple sclerosis, T1 Gd+ = T1-weighted gadolinium-enhanced. For ORATORIO: Proportion of subjects with CDP at Month 12 derived from the KM, (Montalban, 2017), Source: (PROMISE) Wolinsky, 2007, (OLYMPUS) Hawker, 2009, (INFORMS) Lublin, 2016, (ORATORIO) Montalban, 2017.

Based on our experience, we believe that a younger PPMS population with greater MRI activity may be more suitable to treatment, especially one with a high inflammatory burden and thus high otherwise unmet medical need.

In summary, based on our assessment, by including a study population with PPMS of <55 years of age and with lower EDSS, the chance of including subjects with inflammatory disease is increased. There is an unmet need for drugs that target PPMS early, prior to the development of irreversible disability. The penetration of Cladribine into the CNS (Liliemark, 1997) and its presumed action beyond the blood-brain barrier provides a strong further rationale for this study, as the pathophysiology of progressive MS is deemed to involve inflammation within the CNS.

Dosage and Administration

Randomized subjects are administered oral Cladribine or matching placebo in a blinded manner, in 2 once yearly treatment courses during the treatment period.

The first dose is administered at the site and treatment for the following 3-4 days is taken by the patient at home. See appendix below for details.

The recommended cumulative dose of Cladribine is 3.5 mg/kg body weight over 2 years, administered as 1 treatment course of 1.75 mg/kg per year. Each treatment course consists of 2 treatment weeks, 1 week at the beginning of the first month (Baseline) and 1 week at the beginning of the second month (Month 1) and subsequently in the second year at the beginning of Months 12 and 13. Depending on body weight, each treatment week consists of 4 or 5 days on which a subject receives 10 mg or 20 mg (1 or 2 tablets) as a single daily dose.

Following completion of the 2 treatment courses, no further Cladribine treatment is currently deemed required in years 3 and/or 4. However, re-initiation of therapy in year 3 may be an options to further improve the situation of the patients, especially the PPMS patients.

Preferred Criteria for Initiating and Continuing Therapy

Lymphocyte counts must be
normal before initiating Cladribine in year 1,
at least Grade 0 or 1 ALC before initiating Cladribine in year 2.

If necessary, the treatment course in year 2 can be delayed for up to 6 months to allow for recovery of lymphocytes. If this recovery takes more than 6 months the patient should not receive Cladribine anymore.

TABLE 10

Dosages by patient weight
Dose of cladribine per treatment week
by patient weight in each treatment year

| Weight range kg* | Dose in mg (number of 10 mg tablets) per treatment week | |
|---|---|---|
| | Treatment week 1 | Treatment week 2 |
| 40 to <50 | 40 mg (4 tablets) | 40 mg (4 tablets) |
| 50 to <60 | 50 mg (5 tablets) | 50 mg (5 tablets) |
| 60 to <70 | 60 mg (6 tablets) | 60 mg (6 tablets) |
| 70 to <80 | 70 mg (7 tablets) | 70 mg (7 tablets) |
| 80 to <90 | 80 mg (8 tablets) | 70 mg (7 tablets) |
| 90 to <100 | 90 mg (9 tablets) | 80 mg (8 tablets) |
| 100 to <110 | 100 mg (10 tablets) | 90 mg (9 tablets) |
| 110 and above | 100 mg (10 tablets) | 100 mg (10 tablets) |

Subjects are instructed to take the medication at the same time each day with water; tablets must be swallowed whole. As tablets are uncoated, they must be taken immediately after being removed from the blister pack. There are no fasting restrictions; tablets may be taken independent of food intake.

A missed dose must be taken as soon as remembered on the same day according to the treatment schedule.

A missed dose must not be taken together with the next scheduled dose on the following day. In the case of a missed dose, the patient must take the missed dose on the following day, and extend the number of days in that treatment week. If two consecutive doses are missed, the same rule applies, and the number of days in the treatment week is extended by two days.

Example 3

The efficacy and safety of oral Cladribine administration, eventually multi-dose administration, as described herein, can alternatively also be assessed for example following the protocol for the treatment of relapsing forms of MS as given below:

Oral Cladribine in the Treatment of Relapsing Forms of MS

A study of sixty patients with relapsing forms of clinically definite multiple sclerosis is undertaken. Each patient is first examined for normal hepatic, renal, and bone marrow functioning to establish baseline values.

Patients are selected from Male or Female, between 18 and 55 years of age who had one or more relapses within the prior 12 months. Female patients are non-pregnant female.

Patients are randomly assigned to one of the treatment groups listed in Table 11 below.

TABLE 11

| Group | 2-CdA |
|---|---|
| 1 | — |
| 2 | 1.75 mg/kg |
| 3 | 3.5 mg/kg |

Each of the patients in Groups 2 and 3 receives 3 mg or 10 mg 2-CdA (1, 2 or 3 administration(s) a day depending on the patient's weight) combined in cyclodextrin formulation as described in WO 2004/087101, Example 3. The Compositions of the Cladribine formulations in 3 mg or 10 mg 2-CdA tablets containing hydroxypropyl-beta-cyclodextrin are listed in Table 12, below.

TABLE 12

| Name of ingredients | Formula mg/tablet | Formula mg/tablet |
|---|---|---|
| Cladribine-2-hydroxypropyl-ß-cyclodextrin-complex* | 153.75 equivalent to 10 mg 2-CdA | 30.60 equivalent to 3 mg 2-CdA |
| Sorbitol powder | 44.25 | 68.4 |
| Magnesium Stearate (vegetable grade) | 2.0 | 1.00 |
| Total | 200.0 | 100 |

*Cladribine is complexed and lyophilised with 2-hydroxypropyl-ß-cyclodextrin as a separate process as described in WO 2004/087101.

Administration schemes for the induction period depending on the patient's weight are given below in Tables 3 and 4 for the target doses of 1.75 mg/kg and 3.5 mg/kg respectively. For the maintenance period, the example of administration scheme of Table 13 is applicable.

TABLE 13

| Patient weight ranges (kg) | | | Total target dose (kg) equivalent to 1.75 mg/kg | | Number of pills (10 mg)/ induction period | | |
|---|---|---|---|---|---|---|---|
| Min | Mid-range | Max | Min | Max | Month 1 | Month 2 | Total |
| 40 | 42.5 | 44.9 | 28 | 31.4 | 4 | 3 | 7 |
| 45 | 47.5 | 49.9 | 31.5 | 34.9 | 4 | 4 | 8 |
| 50 | 52.5 | 54.9 | 35 | 38.4 | 5 | 4 | 9 |
| 55 | 57.5 | 59.9 | 38.5 | 41.9 | 5 | 5 | 10 |
| 60 | 62.5 | 64.9 | 42 | 45.4 | 5 | 5 | 10 |
| 65 | 67.5 | 69.9 | 45.5 | 48.9 | 6 | 5 | 11 |
| 70 | 72.5 | 74.9 | 49 | 52.4 | 6 | 6 | 12 |
| 75 | 77.5 | 79.9 | 52.5 | 55.9 | 7 | 6 | 13 |
| 80 | 82.5 | 84.9 | 56 | 59.4 | 7 | 6 | 13 |
| 85 | 87.5 | 89.9 | 59.5 | 62.9 | 7 | 7 | 14 |
| 90 | 92.5 | 94.9 | 63 | 66.4 | 8 | 7 | 15 |
| 95 | 97.5 | 99.9 | 66.5 | 69.9 | 8 | 8 | 16 |

TABLE 13-continued

| Patient weight ranges (kg) | | | Total target dose (kg) | | Number of pills (10 mg)/ induction period | | |
|---|---|---|---|---|---|---|---|
| | Mid- | | equivalent to 1.75 mg/kg | | Month | Month | |
| Min | range | Max | Min | Max | 1 | 2 | Total |
| 100 | 102.5 | 104.9 | 70 | 73.4 | 9 | 8 | 17 |
| 105 | 107.5 | 109.9 | 73.5 | 76.9 | 9 | 9 | 18 |
| 110 | 112.5 | 114.9 | 77 | 80.4 | 9 | 9 | 18 |
| 115 | 117.5 | 119.9 | 80.5 | 83.9 | 10 | 9 | 19 |

TABLE 14

| Patient weight ranges (kg) | | | Total target dose (kg) | | Number of pills (10 mg)/ induction period | | | | |
|---|---|---|---|---|---|---|---|---|---|
| | Mid- | | equivalent to 3.5 mg/kg | | Month | Month | Month | Month | |
| Min | range | Max | Min | Max | 1 | 2 | 3 | 4 | Total |
| 40 | 42.5 | 44.9 | 56 | 62.9 | 4 | 4 | 3 | 3 | 14 |
| 45 | 47.5 | 49.9 | 63 | 69.9 | 4 | 4 | 4 | 4 | 16 |
| 50 | 52.5 | 54.9 | 70 | 76.9 | 5 | 4 | 4 | 4 | 17 |
| 55 | 57.5 | 59.9 | 77 | 83.9 | 5 | 5 | 5 | 4 | 19 |
| 60 | 62.5 | 64.9 | 84 | 90.9 | 6 | 5 | 5 | 5 | 21 |
| 65 | 67.5 | 69.9 | 91 | 97.9 | 6 | 6 | 5 | 5 | 22 |
| 70 | 72.5 | 74.9 | 98 | 104.9 | 6 | 6 | 6 | 6 | 24 |
| 75 | 77.5 | 79.9 | 105 | 111.9 | 7 | 7 | 6 | 6 | 26 |
| 80 | 82.5 | 84.9 | 112 | 118.9 | 7 | 7 | 7 | 6 | 27 |
| 85 | 87.5 | 89.9 | 119 | 125.9 | 7 | 7 | 7 | 7 | 28 |
| 90 | 92.5 | 94.9 | 126 | 132.9 | 8 | 8 | 7 | 7 | 30 |
| 95 | 97.5 | 99.9 | 133 | 139.9 | 8 | 8 | 8 | 8 | 32 |
| 100 | 102.5 | 104.9 | 140 | 146.9 | 9 | 8 | 8 | 8 | 33 |
| 105 | 107.5 | 109.9 | 147 | 153.9 | 9 | 9 | 9 | 8 | 35 |
| 110 | 112.5 | 114.9 | 154 | 160.9 | 10 | 9 | 9 | 9 | 37 |
| 115 | 117.5 | 119.9 | 161 | 167.9 | 10 | 10 | 9 | 9 | 38 |

In Group 1 patients receive a placebo (saline) for 4 months followed by 8 months of no treatment.

In Group 2 patients receive a daily oral administration of Cladribine for about 5 days a month during 2 months (induction period) of 2-CdA cyclodextrin formulation such that the total effective dose administered at the end of the first 2 months approximates about 0.7 mg/kg (total dose of about 1.75 mg/kg for a bioavailability of about 40%); followed by administration of placebo for 2 months; followed by 8 months of no treatment.

In Group 3 patients receive a daily oral administration of Cladribine for about 5 days a month for 4 months (induction period) of 2-CdA cyclodextrin formulation such that the total effective dose administered at the end of the first 4 months approximates about 1.4 mg/kg (total dose of about 3.5 mg/kg for a bioavailability of about 40%); followed by 8 months of no treatment.

Beginning at month 13, all 3 patient groups receive re-treatment with Cladribine cyclodextrin formulation for about 5 days a month for 2 months (maintenance period) with the lower dose (such that the total effective dose administered at the end of the first 2 months approximates about 0.7 mg/kg) followed by 10 months of no treatment.

Finally, beginning at month 25, all patient groups receive re-treatment with Cladribine cyclodextrin formulation for about 5 days a month for 2 months (maintenance period) with the lower dose (such that the total effective dose administered at the end of the first 2 months approximates about 0.7 mg/kg) followed by 10 more months of no treatment.

Patients are monitored to determine whether there is any progression or improvement of brain lesions associated with progression of MS through MRI scans and neurological examination as described in Miller et al., 1996, above; Evans et al., 1997, above; Sipe et al., 1984, above; and Mattson, 2002, above. All patients have a baseline and MRI study (brain or spinal cord, according to localization of the lesions) at month 12.

The patient's disability progression and the time for having a first relapse are monitored as well as the proportion of relapse-fee patients at 24 months.

Lymphocyte markers and monocyte counts are monitored in the patients.

Patients in Groups 2 and 3 have a decrease in brain lesions.

The data show that the 2-CdA regimen consisting in the succession of an induction treatment and maintenance treatments is efficient in decreasing brain lesions and no severe adverse effect is observed.

The invention claimed is:

1. A method of treating a progressive form of Multiple Sclerosis, said method comprising: orally administering Cladribine to a patient in need thereof at fixed dose per patient, per body weight and per treatment year, wherein said fixed dose is in a range of 1.5 mg/kg to 4.0 mg/kg, wherein the progressive form of Multiple Sclerosis is selected from the group consisting of Secondary Progressive Multiple Sclerosis (SPMS), Primary Progressive Multiple Sclerosis (PPMS), and Progressive Relapsing Multiple Sclerosis (PRMS), and wherein the progressive form of Multiple Sclerosis does not include Early Secondary Progressive Multiple Sclerosis (ESPMS).

2. The method according to claim 1, wherein said fixed dose per patient is 1.75 mg/kg per treatment year with a maximum deviation of +/−0.2 mg/kg.

3. The method according to claim 1, wherein said progressive form of multiple sclerosis comprises Primary Progressive Multiple Sclerosis and/or Secondary Progressive Multiple Sclerosis.

4. The method according to claim 1, wherein said fixed dose is orally administered to said patient within two adjacent months within said treatment year.

5. The method according to claim 4, wherein said fixed dose is orally administered to said patient within one week or two adjacent weeks at the beginning of each one of said two adjacent months.

6. The method according to claim 4, wherein said fixed dose is orally administered to said patient within 4 to 5 days during said week, or within 4 to 5 days of each of said weeks.

7. The method according to claim 1, wherein said Cladribine is orally administered for at least three treatment years.

8. The method according to claim 1, wherein each treatment year comprises:
   (i) a treatment period of 2 months at the beginning of said treatment year, wherein said fixed dose of Cladribine is orally administered on 3 to 5 days each month at the beginning of each month, said fixed dose being divided into daily doses of 10 or 20 mg of Cladribine, and
   (ii) a Cladribine-free period lasting 10 months, during which no Cladribine is administered.

9. The method according to claim 1, wherein said patient suffers from Primary Progressive Multiple Sclerosis and/or from Secondary Progressive Multiple Sclerosis, wherein said fixed dose per patient is 1.75 mg/kg per treatment year with a maximum deviation of +/−0.2 mg/kg, and wherein orally administering Cladribine comprises at least two treatment years.

10. The method according to claim 1, wherein orally administering Cladribine comprises at least three treatment years,
   a) wherein said fixed dose per treatment year is from 0.75 mg/kg to 2.0 mg/kg,
   b) wherein the third treatment year comprises:
      (i) a treatment period of 1 month or 2 months at the beginning of said treatment year, wherein said fixed dose of Cladribine is orally administered on 3 to 5 days each month at the beginning of each month, said fixed dose being divided into daily doses of 10 or 20 mg of Cladribine, and
      (ii) a Cladribine-free period lasting 11 or 10 months respectively, during which no Cladribine is administered.

11. The method according to claim 1, wherein orally administering Cladribine is in one or two treatment years, optionally plus an additional subsequent treatment year, followed by at least one year in which no Cladribine is administered to said patient.

12. The method according to claim 1, wherein said Cladribine is orally administered as a liquid, a tablet, or a capsule.

13. The method according to claim 1, wherein said Cladribine is orally administered as a tablet comprising 10 mg of Cladribine in the form of a mixture of Cladribine, 2-hydroxypropyl-β-cyclodextrin and Cladribine-2-hydroxypropyl-β-cyclodextrin-complexes, wherein the weight ratio of Cladribine to 2-hydroxypropyl-β-cyclodextrin is between about 1:10 to about 1:16.

14. A method of treating a patient diagnosed as suffering from a progressive form of Multiple Sclerosis, said method comprising:
   orally administering to said patient a cumulative dose of Cladribine of about 3.5 mg/kg body weight, with a maximum deviation of +/−0.4 mg/kg, over 2 years, administered in each year as 1 treatment course of about 1.75 mg/kg+/−0.2 mg/kg per year, wherein each treatment course consists of 2 treatment weeks, one at the beginning of the first month and one at the beginning of the second month of the respective treatment year,
   wherein the progressive form of Multiple Sclerosis is selected from the group consisting of Secondary Progressive Multiple Sclerosis (SPMS), Primary Progressive Multiple Sclerosis (PPMS), and Progressive Relapsing Multiple Sclerosis (PRMS), and wherein the progressive form of Multiple Sclerosis does not include Early Secondary Progressive Multiple Sclerosis (ESPMS).

15. The method according to claim 14, wherein each treatment week consists of 4 or 5 days on which said patient receives 10 mg or 20 mg of Cladribine for oral administration, depending on the body weight of the patient.

16. The method according to claim 15, wherein said patient receives the 10 mg or 20 mg of Cladribine for oral administration as a tablet or capsule.

17. The method according to claim 16, wherein said patient receives the 10 mg or 20 mg of Cladribine for oral administration as a tablet or capsule comprising 10 mg of Cladribine in the form of a mixture of Cladribine, 2-hydroxypropyl-β-cyclodextrin and Cladribine-2-hydroxypropyl-β-cyclodextrin-complexes, wherein the weight ratio of Cladribine to 2-hydroxypropyl-β-cyclodextrin is between about 1:10 to about 1:16.

18. The method according to claim 14, where the progressive form of Multiple Sclerosis is selected from the group consisting of Primary Progressive Multiple Sclerosis and Secondary Progressive Multiple Sclerosis.

19. The method according to claim 18, wherein each treatment week consists of 4 or 5 days on which said patient receives 10 mg or 20 mg of Cladribine for oral administration.

20. The method according to claim 14, wherein said patient is between 18 and 65 years old.

21. The method according to claim 14, wherein the patient additionally receives at least one disease modifying drug other than Cladribine.

22. The method according to claim 21, wherein said at least one disease modifying drug other than Cladribine is an interferon selected from the group consisting of: Interferon beta-1a, Beta interferon-1a, Interferon beta-1b, Beta interferon-1b, and Peginterferon beta 1a.

23. The method according to claim 14, wherein after the completion of said 2 years with said 2 treatment courses, no Cladribine is administered to the patients in the subsequent 1 or 2 years following the completion of said 2 years with said 2 treatment courses.

24. A method of treating a patient suffering from a progressive form of Multiple Sclerosis, comprising orally administering to said patient tablets or capsules containing about 10 mg of Cladribine each, wherein said tablets or capsules are administered during a treatment year comprising the following regimen:
   (i) a treatment course lasting 2 months, wherein Cladribine tablets or capsules are orally administered daily at a daily dose of 10 or 20 mg of Cladribine on a treatment week of from 3 to up to 6 days each month;
   (ii) followed by a Cladribine-free period lasting 10 months wherein no Cladribine is administered to said patient;
wherein patients having a bodyweight
   in the range of 40 to less than 50 kg are administered
      1) 4 tablets or capsules (40 mg of Cladribine) in the 1st treatment week of said treatment course, 2) 4 tablets or capsules (40 mg of Cladribine) in the 2nd treatment week of said treatment course;

in the range of 50 to less than 60 kg are administered
1) 5 tablets or capsules (50 mg of Cladribine) in the 1st treatment week of said treatment course, respectively,
2) 5 tablets or capsules (50 mg of Cladribine) in the 2nd treatment week of said treatment course;

in the range of 60 to less than 70 kg are administered
1) 6 tablets or capsules (60 mg of Cladribine) in the 1st treatment week of said treatment course,
2) 6 tablets or capsules (60 mg of Cladribine) in the 2nd treatment week of said treatment course;

in the range of 70 to less than 80 kg are administered
1) 7 tablets or capsules (70 mg of Cladribine) in the 1st treatment week of said treatment course,
2) 7 tablets or capsules (70 mg of Cladribine) in the 2nd treatment week of said treatment course;

in the range of 80 to less than 90 kg are administered
1) 8 tablets or capsules (80 mg of Cladribine) in the 1st treatment week of said treatment course,
2) 7 tablets or capsules (70 mg of Cladribine) in the 2nd treatment week of said treatment course;

in the range of 90 to less than 100 kg are administered
1) 9 tablets or capsules (90 mg of Cladribine) in the 1st treatment week of said treatment course,
2) 8 tablets or capsules (80 mg of Cladribine) in the 2nd treatment week of said treatment course;

in the range of 100 to less than 110 kg are administered
1) 10 tablets or capsules (100 mg of Cladribine) in the 1st treatment week of said treatment course,
2) 9 tablets or capsules (90 mg of Cladribine) in the 2nd treatment week of said treatment course; or in the range of 110 kg and above are administered
1) 10 tablets or capsules (100 mg of Cladribine) in the 1st treatment week of said treatment course,
2) 10 tablets or capsules (100 mg of Cladribine) in the 2nd treatment week of said treatment course.

25. The method according to claim 24, wherein the method further comprises at least one subsequent additional treatment year, wherein said additional treatment year is substantially identical to said treatment year.

26. The method according to claim 25, wherein said additional treatment year is directly adjacent to said treatment year, or wherein the method comprises a gap of 1 to 10 months in between the two treatment years.

27. A method of treating a patient suffering from a progressive form of Multiple Sclerosis, wherein the progressive form of Multiple Sclerosis is selected from the group consisting of Secondary Progressive Multiple Sclerosis (SPMS), Primary Progressive Multiple Sclerosis (PPMS), and Progressive Relapsing Multiple Sclerosis (PRMS), and wherein the progressive form of Multiple Sclerosis does not include Early Secondary Progressive Multiple Sclerosis (ESPMS), said method comprising orally administering to said patient tablets or capsules containing about 10 mg of Cladribine each, wherein said tablets or capsules are administered during two treatment years comprising the following regimen:

(i) a first treatment course lasting 2 months, wherein Cladribine tablets or capsules are orally administered daily at a daily dose of 10 or 20 mg of Cladribine on 3 to up to 6 days each month;

(ii) followed by a first Cladribine-free period lasting 10 months, wherein no Cladribine is administered to said patient;

(iii) followed by a second treatment course lasting 2 months, wherein Cladribine tablets or capsules are orally administered daily at a daily dose of 10 or 20 mg of Cladribine on 3 to up to 6 days each month; and (iv) followed by a second Cladribine-free period lasting 10 months, wherein no Cladribine is administered to said patient, and wherein patients having a bodyweight
in the range of 40 to less than 50 kg are administered
1) 4 tablets or capsules (40 mg of Cladribine) in the 1st treatment week of both the 1st and the 2nd treatment course, respectively,
2) 4 tablets or capsules (40 mg of Cladribine) in the 2nd treatment week of both the 1st and the 2nd treatment course, respectively:

in the range of 50 to less than 60 kg are administered
1) 5 tablets or capsules (50 mg of Cladribine) in the 1st treatment week of both the 1st and the 2nd treatment course, respectively,
2) 5 tablets or capsules (50 mg of Cladribine) in the 2nd treatment week of both the 1st and the 2nd treatment course, respectively:

in the range of 60 to less than 70 kg are administered
1) 6 tablets or capsules (60 mg of Cladribine) in the 1st treatment week of both the 1st and the 2nd treatment course, respectively,
2) 6 tablets or capsules (60 mg of Cladribine) in the 2nd treatment week of both the 1st and the 2nd treatment course, respectively;

in the range of 70 to less than 80 kg are administered
1) 7 tablets or capsules (70 mg of Cladribine) in the 1st treatment week of both the 1st and the 2nd treatment course, respectively,
2) 7 tablets or capsules (70 mg of Cladribine) in the 2nd treatment week of both the 1st and the 2nd treatment course, respectively;

in the range of 80 to less than 90 kg are administered
1) 8 tablets or capsules (80 mg of Cladribine) in the 1st treatment week of both the 1st and the 2nd treatment course, respectively,
2) 7 tablets or capsules (70 mg of Cladribine) in the 2nd treatment week of both the 1st and the 2nd treatment course, respectively;

in the range of 90 to less than 100 kg are administered
1) 9 tablets or capsules (90 mg of Cladribine) in the 1st treatment week of both the 1st and the 2nd treatment course, respectively,
2) 8 tablets or capsules (80 mg of Cladribine) in the 2nd treatment week of both the 1st and the 2nd treatment course, respectively;

in the range of 100 to less than 110 kg are administered
1) 10 tablets or capsules (100 mg of Cladribine) in the 1st treatment week of both the 1st and the 2nd treatment course, respectively,
2) 9 tablets or capsules (90 mg of Cladribine) in the 2nd treatment week of both the 1st and the 2nd treatment course, respectively; or in the range of 110 kg and above are administered
1) 10 tablets or capsules (100 mg of Cladribine) in the 1st treatment week of both the 1st and the 2nd treatment course, respectively,
2) 10 tablets or capsules (100 mg of Cladribine) in the 2nd treatment week of both the 1st and the 2nd treatment course, respectively.

28. The method according to claim 27, wherein said 10 mg or 20 mg of Cladribine for oral administration are administered to the patient as a tablet or capsule comprising 10 mg of Cladribine in the form of a mixture of Cladribine, 2-hydroxypropyl-β-cyclodextrin and Cladribine-2-hydroxypropyl-β-cyclodextrin-complexes, wherein the weight ratio of Cladribine to 2-hydroxypropyl-β-cyclodextrin is between about 1:10 to about 1:16.

29. The method according to claim 27, wherein the progressive form of Multiple Sclerosis is Primary Progressive Multiple Sclerosis.

30. The method according to claim 27, wherein the progressive form of Multiple Sclerosis is Secondary Progressive Multiple Sclerosis.

31. The method according to claim 27, wherein the patient additionally receives at least one disease modifying drug other than Cladribine.

32. The method according to claim 31, wherein said at least one disease modifying drug other than Cladribine is an interferon selected from the group consisting of: Interferon beta-1a, Beta interferon-1a, Interferon beta-1b, Beta interferon-1b, and Peginterferon beta 1a.

33. The method according to claim 27, wherein to the patients having completed said 2 treatment courses of one year each, no further Cladribine treatment is administered to said patients in the subsequent years 3 and 4.

34. The method according to claim 27, wherein the progressive form of Multiple Sclerosis is selected from the group consisting of Primary Progressive Multiple Sclerosis and Secondary Progressive Multiple Sclerosis.

* * * * *

UNITED STATES PATENT AND TRADEMARK OFFICE
CERTIFICATE OF CORRECTION

PATENT NO. : 10,849,919 B2
APPLICATION NO. : 16/199119
DATED : December 1, 2020
INVENTOR(S) : Fernando Dangond Page 1 of 1

It is certified that error appears in the above-identified patent and that said Letters Patent is hereby corrected as shown below:

In the Specification

Column 1, Line 9:
"Nov. 24, 2018,"
Should read:
--Nov. 24, 2017,--; and

In the Claims

Column 65, Line 5, Claim 6:
"according to claim 4"
Should read:
--according to claim 5--.

Signed and Sealed this
Twenty-fifth Day of October, 2022

Katherine Kelly Vidal
*Director of the United States Patent and Trademark Office*